US011246793B2

United States Patent
George et al.

(10) Patent No.: US 11,246,793 B2
(45) Date of Patent: Feb. 15, 2022

(54) EAR PUMPS

(71) Applicant: NOCIRA, LLC, Tempe, AZ (US)

(72) Inventors: David Mager George, Tempe, AZ (US); James Clayton Peacock, III, Tempe, AZ (US)

(73) Assignee: NOCIRA, LLC, Tempe, AZ (US)

( * ) Notice: Subject to any disclaimer, the term of this patent is extended or adjusted under 35 U.S.C. 154(b) by 228 days.

(21) Appl. No.: 16/549,222

(22) Filed: Aug. 23, 2019

(65) Prior Publication Data

US 2020/0222272 A1 Jul. 16, 2020

Related U.S. Application Data

(63) Continuation of application No. PCT/US2018/019981, filed on Feb. 27, 2018.
(Continued)

(51) Int. Cl.
*A61H 21/00* (2006.01)
*A61F 11/00* (2006.01)
*A61H 9/00* (2006.01)

(52) U.S. Cl.
CPC .............. *A61H 21/00* (2013.01); *A61F 11/00* (2013.01); *A61H 9/0057* (2013.01);
(Continued)

(58) Field of Classification Search
CPC ........ H04R 1/1016; A61F 11/12; A61F 11/00; A61H 21/00; A61H 9/0057; A61H 2009/0064; A61H 2201/1253; A61H 2201/1645; A61H 9/00; A61H 9/0007; A61H 9/005; A61H 2201/0153; A61H 23/04; A61H 9/0071; A61H 23/02; A61H 2201/1207; A61H 2201/1607; A61H 2205/027
See application file for complete search history.

(56) References Cited

U.S. PATENT DOCUMENTS 787,443 A * 4/1905 Godman et al. ....... A61H 21/00
601/77
841,146 A 1/1907 Hasbrouck
(Continued)

FOREIGN PATENT DOCUMENTS

| AU | 2004/238090 | 11/2004 |
|----|---|---|
| CA | 1136751 | 11/1982 |

(Continued)

OTHER PUBLICATIONS

Akerman, et al. Pearls and pitfalls in experimental invivo models of migraine: Dural trigerninovascular nociception. Cephalagia, 2013, 33 (8), pp. 557-592.
(Continued)

*Primary Examiner* — Tu A Vo
(74) *Attorney, Agent, or Firm* — Knobbe Martens Olson & Bear, LLP

(57) ABSTRACT

A manual ear pump including one or more of a support element configured to releasably engage an external ear canal and having an interior chamber, a resilient element capable of being resiliently deformed coupled to a support element, and an aperture disposed on a support element bottom surface communicating with the external ear canal and interior chamber.

18 Claims, 32 Drawing Sheets

Related U.S. Application Data

(60) Provisional application No. 62/464,102, filed on Feb. 27, 2017.

(52) U.S. Cl.
CPC ............... *A61H 2009/0064* (2013.01); *A61H 2201/1253* (2013.01); *A61H 2201/1645* (2013.01)

(56) References Cited

U.S. PATENT DOCUMENTS

| | | | |
|---|---|---|---|
| 853,645 A * | 5/1907 | Meyer | A61F 11/00 601/77 |
| 2,176,366 A * | 10/1939 | Smith | A61H 9/005 604/212 |
| 2,437,490 A | 3/1948 | Watson et al. | |
| 2,652,048 A | 9/1953 | Joers | |
| 3,757,769 A | 9/1973 | Arguimbau et al. | |
| 3,872,559 A | 3/1975 | Leight | |
| 4,002,161 A | 1/1977 | Klar et al. | |
| 4,133,984 A | 1/1979 | Watson et al. | |
| 4,160,449 A | 7/1979 | Wade | |
| 4,206,756 A | 6/1980 | Grossan | |
| 4,244,377 A | 1/1981 | Grams | |
| 4,289,143 A | 9/1981 | Canavesio et al. | |
| 4,325,386 A | 4/1982 | Katz | |
| 4,349,083 A | 9/1982 | Bennett | |
| 4,472,342 A | 9/1984 | Carr | |
| 4,552,137 A | 11/1985 | Strauss | |
| 4,594,058 A | 6/1986 | Fischell | |
| 4,632,104 A | 12/1986 | Row | |
| 4,667,676 A | 5/1987 | Guinta | |
| 4,688,582 A | 8/1987 | Heller et al. | |
| 4,754,748 A | 7/1988 | Antowski | |
| 4,757,807 A | 7/1988 | Densert et al. | |
| 4,775,370 A | 10/1988 | Berry | |
| 4,809,708 A | 3/1989 | Geisler et al. | |
| 4,896,380 A | 1/1990 | Kamitani | |
| 4,896,679 A | 1/1990 | St. Pierre | |
| 4,964,769 A | 10/1990 | Hass | |
| 4,984,579 A | 1/1991 | Burgert et al. | |
| 5,024,612 A * | 6/1991 | van den Honert | A61F 11/00 604/36 |
| 5,105,822 A | 4/1992 | Stevens et al. | |
| 5,131,411 A | 7/1992 | Casali et al. | |
| 5,228,431 A | 7/1993 | Giarretto | |
| 5,241,967 A | 9/1993 | Yasushi et al. | |
| 5,421,818 A | 6/1995 | Arenberg | |
| 5,476,446 A | 12/1995 | Arenburg | |
| 5,483,027 A | 1/1996 | Krause | |
| 5,483,975 A | 1/1996 | Hirschebain | |
| 5,488,961 A | 2/1996 | Adams | |
| 5,631,965 A | 5/1997 | Chang et al. | |
| 5,699,809 A | 12/1997 | Combs et al. | |
| 5,740,258 A | 4/1998 | Goodwin-Johansson | |
| 5,746,725 A | 5/1998 | Shalon et al. | |
| 5,755,234 A | 5/1998 | Mobley et al. | |
| 5,769,891 A | 6/1998 | Clayton | |
| 5,776,179 A | 7/1998 | Ren et al. | |
| 5,819,745 A | 10/1998 | Mobley et al. | |
| 5,865,183 A | 2/1999 | Hirschebain | |
| 5,868,682 A | 2/1999 | Combe et al. | |
| 5,944,711 A | 8/1999 | Pender | |
| 6,004,274 A | 12/1999 | Nolan et al. | |
| 6,016,499 A | 1/2000 | Ferguson | |
| 6,024,726 A | 2/2000 | Hill | |
| 6,129,174 A | 10/2000 | Brown et al. | |
| 6,139,507 A | 10/2000 | Jeng | |
| 6,159,171 A | 12/2000 | Densert et al. | |
| 6,186,959 B1 | 2/2001 | Canfield et al. | |
| 6,258,067 B1 | 7/2001 | Hill | |
| 6,296,652 B1 | 10/2001 | Qingmin | |
| 6,359,993 B2 | 3/2002 | Birmhall | |
| 6,430,443 B1 | 8/2002 | Karell | |
| 6,511,437 B1 | 1/2003 | Nakamura et al. | |
| 6,592,512 B2 | 7/2003 | Stöckert et al. | |
| 6,629,938 B1 | 10/2003 | Engvall et al. | |
| 6,725,568 B2 | 4/2004 | Gronka | |
| 6,748,275 B2 | 6/2004 | Lattner et al. | |
| 6,800,062 B2 | 10/2004 | Epley | |
| 6,820,717 B2 | 11/2004 | Fleming et al. | |
| 6,878,128 B2 | 4/2005 | MacMahon et al. | |
| 6,958,043 B2 | 10/2005 | Hissong | |
| 6,981,569 B2 | 1/2006 | Stilp | |
| 7,022,090 B1 | 4/2006 | Engvall et al. | |
| 7,162,039 B1 | 1/2007 | Callahan | |
| 7,179,238 B2 | 2/2007 | Hissong | |
| 7,189,252 B2 | 3/2007 | Krueger | |
| 7,268,466 B2 | 9/2007 | Rasmussen | |
| 7,352,871 B1 | 4/2008 | Mozo | |
| D570,457 S | 6/2008 | Brown | |
| 7,613,519 B2 | 11/2009 | De Ridder | |
| 7,766,858 B2 | 8/2010 | Franz et al. | |
| 7,779,844 B2 | 8/2010 | Purcell et al. | |
| 7,785,346 B2 | 8/2010 | Blumberg | |
| 7,797,042 B2 | 9/2010 | Dietrich et al. | |
| 7,833,282 B2 | 11/2010 | Mandpe | |
| 7,892,180 B2 | 2/2011 | Epley | |
| 7,959,597 B2 | 6/2011 | Baker et al. | |
| 7,988,657 B2 | 8/2011 | Shapiro et al. | |
| 8,020,563 B2 | 9/2011 | Pfanstiehl | |
| 8,047,207 B2 | 11/2011 | Perez et al. | |
| 8,052,693 B2 | 11/2011 | Shahoian | |
| 8,122,892 B2 | 2/2012 | Johnson et al. | |
| 8,142,373 B1 | 3/2012 | Riles | |
| 8,199,919 B2 | 6/2012 | Goldstein et al. | |
| 8,241,224 B2 | 8/2012 | Keefe | |
| 8,249,285 B2 | 8/2012 | Killion et al. | |
| 8,251,925 B2 | 8/2012 | Keady et al. | |
| 8,262,717 B2 | 9/2012 | Rogers et al. | |
| 8,267,983 B2 | 9/2012 | Rogers et al. | |
| 8,267,984 B2 | 9/2012 | Rogers | |
| 8,328,830 B1 | 12/2012 | Pandit | |
| 8,398,562 B2 | 3/2013 | Keller | |
| 8,414,521 B2 | 4/2013 | Baker et al. | |
| 8,442,632 B2 | 5/2013 | Kullok et al. | |
| 8,460,356 B2 | 6/2013 | Rogers et al. | |
| 8,506,469 B2 | 8/2013 | Dietrich et al. | |
| 8,515,552 B2 | 8/2013 | Englehart | |
| 8,550,206 B2 | 10/2013 | Keady et al. | |
| 8,568,348 B2 | 10/2013 | Vlodaver | |
| 8,603,152 B2 | 12/2013 | Smith et al. | |
| 8,625,833 B1 | 1/2014 | Armwood | |
| 8,666,502 B2 | 3/2014 | Hartlep et al. | |
| 8,688,239 B2 | 4/2014 | Hartlep et al. | |
| 8,696,724 B2 | 4/2014 | Rogers | |
| 8,858,430 B2 | 10/2014 | Oyadiran et al. | |
| 8,963,914 B2 | 2/2015 | Rawat et al. | |
| 9,039,639 B2 | 5/2015 | George et al. | |
| 9,168,171 B2 | 10/2015 | Rogers | |
| 9,186,277 B2 | 11/2015 | George et al. | |
| 9,283,111 B2 | 3/2016 | Rogers et al. | |
| 9,526,653 B2 | 12/2016 | Rogers et al. | |
| 9,532,900 B2 | 1/2017 | Smith et al. | |
| 9,579,247 B2 | 2/2017 | Juto et al. | |
| 9,655,772 B2 | 5/2017 | Smith et al. | |
| 9,744,074 B2 | 8/2017 | Rogers | |
| 9,849,026 B2 | 12/2017 | Rogers et al. | |
| 10,076,464 B2 | 9/2018 | George et al. | |
| 10,251,790 B2 | 4/2019 | George et al. | |
| 10,271,992 B2 | 4/2019 | Hayahi et al. | |
| 10,278,868 B2 | 5/2019 | George et al. | |
| 10,376,695 B2 | 8/2019 | Ericco et al. | |
| 10,760,566 B2 | 9/2020 | George et al. | |
| 10,772,766 B2 | 9/2020 | Sullivan | |
| 11,065,444 B2 | 7/2021 | Ericco et al. | |
| 11,090,194 B2 | 8/2021 | George et al. | |
| 2002/0069883 A1 | 6/2002 | Hirchenbain | |
| 2003/0105450 A1 * | 6/2003 | Dimick | A61F 11/00 604/514 |
| 2003/0195588 A1 | 10/2003 | Fischell et al. | |
| 2003/0220536 A1 | 11/2003 | Hissong | |
| 2004/0097839 A1 | 5/2004 | Epley | |

(56) References Cited

U.S. PATENT DOCUMENTS

| | | |
|---|---|---|
| 2004/0163882 A1 | 8/2004 | Fleming et al. |
| 2005/0065585 A1 | 3/2005 | Salas |
| 2005/0165460 A1 | 7/2005 | Erfan |
| 2005/0209516 A1 | 9/2005 | Fraden |
| 2005/0267388 A1 | 12/2005 | Hanna |
| 2006/0100681 A1 | 5/2006 | Salas Carpizo |
| 2006/0197412 A1 | 9/2006 | Rasmussen |
| 2006/0253087 A1* | 11/2006 | Vlodaver ............... A61M 31/00 604/275 |
| 2006/0272650 A1 | 12/2006 | Hoogenakker et al. |
| 2007/0040454 A1 | 2/2007 | Freudenberger et al. |
| 2007/0112279 A1 | 5/2007 | Iseberg et al. |
| 2007/0250119 A1 | 10/2007 | Tyler et al. |
| 2007/0299362 A1 | 12/2007 | Epley et al. |
| 2008/0011308 A1 | 1/2008 | Fleming |
| 2008/0154183 A1 | 6/2008 | Baker et al. |
| 2008/0168775 A1 | 7/2008 | Windheim et al. |
| 2008/0208100 A1 | 8/2008 | Wolff |
| 2008/0212787 A1 | 9/2008 | Goldstein et al. |
| 2008/0220092 A1 | 9/2008 | Dipierro |
| 2008/0240942 A1 | 10/2008 | Heinrich et al. |
| 2008/0249439 A1 | 10/2008 | Tracey et al. |
| 2008/0264464 A1 | 10/2008 | Lee et al. |
| 2009/0012420 A1 | 1/2009 | Keller |
| 2009/0082831 A1 | 3/2009 | Paul et al. |
| 2009/0173353 A1 | 7/2009 | Pursell et al. |
| 2009/0182399 A1 | 7/2009 | Sylvestre |
| 2009/0228103 A1 | 9/2009 | Clayton |
| 2009/0293886 A1 | 12/2009 | Dedrick et al. |
| 2010/0002897 A1 | 1/2010 | Keady |
| 2010/0030131 A1 | 2/2010 | Morris et al. |
| 2010/0071707 A1 | 3/2010 | Wohl |
| 2010/0071708 A1* | 3/2010 | Lenhardt ............... A61F 11/08 128/868 |
| 2010/0113991 A1 | 5/2010 | Wu |
| 2010/0179490 A1 | 7/2010 | Connelly et al. |
| 2010/0198282 A1 | 8/2010 | Rogers |
| 2010/0211142 A1 | 8/2010 | Rogers |
| 2011/0079227 A1 | 4/2011 | Turcot et al. |
| 2011/0097141 A1 | 4/2011 | Browm |
| 2011/0098551 A1 | 4/2011 | Zhang |
| 2011/0130786 A1 | 6/2011 | Clayton et al. |
| 2011/0172739 A1 | 7/2011 | Mann et al. |
| 2011/0184341 A1 | 7/2011 | Baker et al. |
| 2011/0224493 A1 | 9/2011 | Oyadiran et al. |
| 2011/0245902 A1 | 10/2011 | Katz |
| 2011/0301572 A1* | 12/2011 | Vlodaver ............... A61M 31/00 604/514 |
| 2012/0046607 A1 | 2/2012 | Syk |
| 2012/0203309 A1 | 8/2012 | Englehart |
| 2012/0265093 A1 | 10/2012 | Allen et al. |
| 2012/0296268 A1 | 11/2012 | Vlodavaer et al. |
| 2012/0302859 A1 | 11/2012 | Keefe |
| 2012/0310077 A1 | 12/2012 | Rogers |
| 2012/0310313 A1 | 12/2012 | Rogers et al. |
| 2012/0318605 A1 | 12/2012 | Brown |
| 2013/0123889 A1 | 5/2013 | Katz et al. |
| 2013/0136285 A1* | 5/2013 | Naumann ............ H04R 1/1016 381/329 |
| 2013/0152949 A1 | 6/2013 | Simon |
| 2013/0177179 A1 | 7/2013 | Ambrose et al. |
| 2013/0183173 A1 | 7/2013 | Kohli et al. |
| 2013/0282070 A1 | 10/2013 | Cowan et al. |
| 2013/0303953 A1 | 11/2013 | Lattner |
| 2013/0304103 A1 | 11/2013 | Burres |
| 2013/0310907 A1 | 11/2013 | Rogers et al. |
| 2013/0324932 A1 | 12/2013 | Cogley |
| 2013/0331823 A1 | 12/2013 | Askem et al. |
| 2014/0069442 A1 | 3/2014 | Lewis et al. |
| 2014/0088671 A1 | 3/2014 | Rogers et al. |
| 2014/0243941 A1 | 8/2014 | Rogers et al. |
| 2014/0249608 A1 | 9/2014 | Rogers |
| 2014/0275827 A1 | 9/2014 | Gill et al. |
| 2014/0309718 A1 | 10/2014 | Smith et al. |
| 2014/0334652 A1 | 11/2014 | Gebert |
| 2015/0000678 A1* | 1/2015 | Buckler ............... A61H 21/00 128/867 |
| 2015/0003644 A1* | 1/2015 | George ............... A61F 11/12 381/165 |
| 2015/0005661 A1 | 1/2015 | Trammell |
| 2015/0141879 A1 | 5/2015 | Harper et al. |
| 2015/0320591 A1 | 11/2015 | Smith et al. |
| 2015/0320592 A1 | 11/2015 | Black et al. |
| 2015/0374538 A1 | 12/2015 | Rogers |
| 2016/0128897 A1 | 5/2016 | George et al. |
| 2016/0151206 A1* | 6/2016 | George ............... A61H 9/0071 128/866 |
| 2016/0166203 A1 | 6/2016 | Goldstein |
| 2016/0346117 A1 | 12/2016 | Rogers et al. |
| 2016/0378945 A1 | 12/2016 | Mian et al. |
| 2017/0105876 A1 | 4/2017 | O'Connell, Sr. et al. |
| 2017/0109988 A1 | 4/2017 | O'Connell, Sr. et al. |
| 2017/0135854 A1 | 5/2017 | Rogers et al. |
| 2017/0235889 A1 | 8/2017 | Main et al. |
| 2018/0008457 A1 | 1/2018 | Smith et al. |
| 2018/0023558 A1 | 1/2018 | George et al. |
| 2018/0106244 A1 | 4/2018 | Wang et al. |
| 2018/0125748 A1 | 5/2018 | Goldenberg et al. |
| 2019/0231597 A1 | 8/2019 | Sullivan |
| 2020/0121544 A1 | 4/2020 | George et al. |
| 2021/0222684 A1 | 7/2021 | George et al. |
| 2021/0228414 A1 | 7/2021 | George et al. |

FOREIGN PATENT DOCUMENTS

| | | |
|---|---|---|
| CA | 1222464 | 6/1987 |
| CA | 1241152 | 8/1988 |
| CA | 2003452 | 6/1990 |
| CA | 2275057 | 10/1999 |
| CA | 2 337 076 | 1/2000 |
| CA | 2429560 | 1/2004 |
| CN | 2075517 U | 4/1991 |
| CN | 2418864 | 2/2001 |
| CN | 1308513 A | 8/2001 |
| CN | 2530645 | 1/2003 |
| CN | 2721057 Y | 8/2005 |
| CN | 1791370 A | 6/2006 |
| CN | 2912525 | 6/2007 |
| CN | 200945215 Y | 9/2007 |
| CN | 201143258 | 11/2008 |
| CN | 201164541 | 12/2008 |
| CN | 101668497 | 3/2010 |
| CN | 201505220 U | 6/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |
| CN | 102892392 A | 1/2013 |
| CN | 102986250 | 3/2013 |
| DE | 102011008802 | 7/2012 |
| EP | 0 026 247 | 4/1981 |
| EP | 0 400 900 | 12/1990 |
| EP | 1 027 863 | 8/2000 |
| EP | 2 207 366 | 7/2010 |
| EP | 2 990 017 | 3/2016 |
| FR | 2 605 516 A1 | 4/1988 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | S 57-188245 | 11/1982 |
| JP | H 07-111987 | 5/1995 |
| JP | 2006-345903 | 12/2006 |
| JP | 2009-022699 | 2/2009 |

(56) References Cited

FOREIGN PATENT DOCUMENTS

| | | |
|---|---|---|
| JP | 2010-233643 | 10/2010 |
| JP | 2011-217986 | 11/2011 |
| JP | 2013-068448 | 4/2013 |
| JP | 2013-102784 | 5/2013 |
| KR | 10-1273296 | 6/2013 |
| MX | PA03005598 | 10/2004 |
| MX | 2010014470 | 2/2011 |
| MX | 2011006854 | 8/2011 |
| MX | 2012007726 | 8/2012 |
| WO | WO 1986/01399 | 3/1986 |
| WO | WO 1994/22372 | 10/1994 |
| WO | WO 1996/23293 | 8/1996 |
| WO | WO 1997/23178 | 7/1997 |
| WO | WO 2000/001331 | 1/2000 |
| WO | WO 2000/001346 | 1/2000 |
| WO | WO 2000/010484 | 3/2000 |
| WO | WO 2000/010627 | 3/2000 |
| WO | WO 2000/010848 | 3/2000 |
| WO | WO 2003/075761 | 9/2003 |
| WO | WO 2004/064672 | 8/2004 |
| WO | WO 2004/100844 | 11/2004 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2010/005899 | 1/2010 |
| WO | WO 2010/016925 | 2/2010 |
| WO | WO 2010/085196 | 7/2010 |
| WO | WO 2010/132359 | 11/2010 |
| WO | WO 2011/075573 | 6/2011 |
| WO | WO 2011/075574 | 6/2011 |
| WO | WO 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/175257 | 10/2014 |
| WO | WO 2014/210457 | 12/2014 |
| WO | WO 2015/009421 | 1/2015 |
| WO | WO 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| WO | WO 2017/197150 | 11/2017 |
| WO | WO 2018/106839 | 6/2018 |
| WO | WO 2018/157143 | 8/2018 |
| WO | WO 2019/246456 | 12/2019 |
| ZA | 200509787 | 1/2009 |

OTHER PUBLICATIONS

Baguley et al. Does caloric vestibular stimulation modulate tinnitus? Neuroscience Letters, Mar. 2011, 492(1), pp. 52-54.
Baier, et al.: "Vestibular-Evoked Myogenic Potentials In "Vestibular Migraine" and Meniere's Disease," Ann. N.Y. Acad. Sci., May 2009, 1164, pp. 324-327.
Becker: Weather and migraine: Can so many patients be wrong? Cephalalgia, Mar. 2011, 31(4), pp. 387-390.
Bolay et al.,: "Does Low Atmospheric Pressure Independently Trigger Migraine?" Headache, Oct. 2011, 51(9), pp. 1426-1430.
Breathometer. Breathometer—The World's First Smartphone Breathalyzer. Website, http://www.breathometer.co, originall downloaded Jun. 19, 2014, 8 total pages.
Cadwell. Sierra Wave. Website, http://www.cadwell.com, originally downloaded Feb. 27, 2014, 1 page.
Cathcart, et al., "Pain sensitivity mediates the relationship between stress and headache intensity in chronic tension-type headache", Nov. 2012 (Year: 2012) in 5 pages.
Cranial Nerves—Wikipedia, https://en.wikipedia.org/aiki/Cranial_nerves, printed Aug. 16, 2019 in 12 pages.
Croley, Christen, "Mechanicsburg doctor develops new migraine therapy," The Sentinel, Nov. 9, 2012.
DaSilva, et al.: "tdCS-Induced Analgesia and Electrical Fields in Pain-Related Neural Networks in Chronic Migraine," The Journal of Head and Face Pain, Sep. 2012, 52, pp. 1283-1295.
Dirckx et al. Human tympanic membrane deformation under static pressure. Hearing Research, Jan. 1991, 51(1), pp. 93-106.
Facebook. ZōK: The first migraine and headache solution, Webpage, https://www.facebook.com, originally downloaded May 18, 2017, 10 pages total.
Fasold et al. Human Vestibular Cortex as Identified with Caloric Stimulation in Functional Magnetic Resonance Imaging. Neuroimage, Nov. 2002, 17(3), pp. 1384-1393.
Ferrotec. Thermal Solutions. Website: http://thermal.ferrotec.com, originally downloaded Feb. 27, 2014, 1 page.
Ferrotec. Thermoelectric Technical Reference—Installation of Thermoelectric Modules. Website, http://thermal.ferrotec.com, originally downloaded May 21, 2014, 4 total pages.
Ferrotec. Thermoelectric Technical Reference—Introduction to Thermoelectric Cooling. Website, http://forrotec.com, originally downloaded Feb. 27, 2014, 2 total pages.
George et al. Safety and usability factors in development of a novel, automated treatment device for acute migraine. Biomedical sciences instrumentation. Biomedical sciences instrumentation, Jan. 2017, 53, pp. 398-403.
Hahn: "Let Me Blow in Your Ear, for Migraine Treatment, Of Course," Smile Columbia Dentistry, https://www.tmjtreatmentse.com, originally downloaded Apr. 25, 2016, 2 pages total.
Hu et al. Burden of migraine in the United States: disability and economic costs. Arch. Intern. Med., Apr. 1999, 159, pp. 813-818.
International Search Report and Written Opinion in co-pending application No. PCT/US2018/019981, dated Jun. 27, 2018 in 15 pages.
Janetta Neurovascular Compress in Cranial Nerve and Systemic Disease. Ann Surg, Oct. 1980, 192( 4), pp. 518-524.
Job et al. Cortical Representation of Tympanic Membrane Movements due to Pressure Variation: An ±MRI Study Human Brain Mapping, May 2011, 32(5), pp. 744-749.
Kickstarter. ZōK: The first headache product that solves migraines and headaches. Website, https://www.funded.today, originally downloaded May 18, 2017, 3 pages total.
Klingner et al.: "Components of vestibular cortical function," Behavioral Brain Research, Jan. 2013, 236(1 ), pp. 194-199.
Kolev. How caloric vestibular irrigation influences migraine attacks. Cephalgia. Aug. 1990, vol. 10 issue 4, pp. 167-169 (abstract only).
Lifting the Burden. The Global Campaign Against Headache. Website, http://www.l-t-b.org, originally downloaded Feb. 27, 2014, 1 page.
Liszewski: Ear Pressure Equalizer. Website, http://www.ohgizmo.com, originally downloaded Dec. 18, 2013, 1 page.
Long Island news12.com. Long Island Naturally: Migraines. Website video, http://longisland.news12.com/multimedia/long-island-naturally-migraines-1.6501113, Nov. 26, 2013, 3 total pages.
Mayr: The Origins of Feedback Control. M.I.T. Press, 1970.
McGeoch et al. Vestibular stimulation can relieve central pain of spinal origin. Spinal Cord, Nov. 2008, 46(11), pp. 756-757.
Medscape. Peripheral Nerve Stimulator—Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 total pages.

(56) References Cited

OTHER PUBLICATIONS

Medtronic. Restore Life's Balance with Meniett Therapy. The Meniett Device for Meniere's Disease. On-line article, http://www.medtronic.com, originally downloaded Mar. 13, 2015, 2 total pages.
Meng et al. Migraine Prevention with a Supraorbital Transcutaneous Stimulator: A Randomized Controlled Trial. Neurology, Sep. 2013, 81, pp. 1102-1103.
Minen. Tinnitus and Headache. American Migraine Foundation, website, downloaded Feb. 8, 2017, 3 pages total.
Mosqueria et al. Vagus Nerve Stimulation in Patients with Migraine. Rev Neurol, 2013, 57(2), English Abstract.
Nagai et al. Encapsulated nerve corpuscles in the human tympanic membrane. Archives of Otorhinolaryngology, 1989, 246(3), pp. 169-172.
New York Health Soultions. Migraine Headaches. Website, http://www.nyhealthsolutions.com, originally downloaded May 23, 2014, 2 pages.
Nihashi et al. Representation of the ear in human primary somatosensory cortex. Neuroimage, Feb. 2001, 13(2), pp. 295-304 (abstract only).
Olesen et al. Emerging Migraine treatments and drug targets. Trends in Pharmacological Sciences, 2011, 32( 6), pp. 352-359.
Pederson et al. Neurostimulation in cluster headache: A review of current progress. Cephalagia, 2013, 33(14 ), pp. 1179-1193.
Pietrobon, Migraine: new molecular mechanism. Neuroscientist. Aug. 2005, vol. 11, Issue 4, pp. 373-386 (abstract only).
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.
Saunders, Tympanic membrane sensation. Brain. Jun. 1985, vol. 108, Issue 6,pp. 378-404 (abstract only) in 1 page.
Schoenen et al. Migraine prevention with a supraorbital transcutaneous stimulator. Neurology, 2013, 80(8), pp. 697-704.
Schulman. Breath-Holding, Head Pressure, and Hot Water: An Effective Treatment for Migraine Headache. Headache, Nov.-Dec. 2002, 42(10), pp. 1048-1050.
Scion Neurostim. Therapeutic Neuromodulation via Caloric Vestibular Stimulation. Thermoneuromodulation (TNM). Slides for presentation, dated Sep. 2015, 12 pages total.
Sheftell, F, Steiner, TJ, Thhomas, H. Harry Potter and the Curse of Headache. Headache: The Journal of Head and Face Pain. Jun. 2007, vol. 47, Issue 6, pp. 911-916 (abstract only) in 1 page.
Shevel, "Headaches and tinnitus: correlation found", May 2008 (Year: 2006).
Silberstein et al.: "Botulinum Toxin Type A as a Migraine Preventive Treatment," The Journal of Head and Face Pain, Jun. 2000, 40, pp. 445-450.
Smartproducts. Series 100—Cartridge Specialty Check Valves and Pressure Relief Valves. Online catalog, www.smartproducts,com, originally downloaded Mar. 28, 2014, 2 total.
Stender, Dr., "Easing Migraine Symptoms with a Simple Puff of Air into the Ear," Pasadena Pain Management, http://www.pasadenapainmanagement.com, downloaded Apr. 25, 2016, 5 pages total.
Stovnver, LJ, et al. The global burden of headache: a documentation of headache prevalence and disability worldwide. Cephalagia, 2007. vol. 27, pp. 193-210.
Sullivan: "Ear Insufflation As A Novel Therapy Which Produces Rapid Relief Of Migraine Headache—a Case Study," Funct Neurol Rehabil Egon 2013; vol. 3, Issue 1, pp. 93-107. Published on Jun. 7, 2013. Revised Jan. 28, 2013. Accepted Feb. 15, 2013.
Sullivan: "Ear Insufflation Produces Rapid and Significant Relief of Trigeminal Neuraliga," Funct Neurol Rehabil Egon 2013; vol. 3, Issue 4, pp. 1-6. Published on May 26, 2014. Revised Dec. 24, 2013. Accepted Jan. 12, 2014.
Transcript of News Story, Aug. 22, 2013, video available at: https://www.facebook.com/178787878873891/videos/10201196245541704/.
"New Migraine Therapy," Aug. 22, 2013, video available at https://www.facebook.com/178787878873891/videos/10201196245541704/.
Transcript of News Story, Nov. 13, 2013, video available at: https://www.facebook.com/178787878873891/videos/treatment-for-migraines-and-trigeminal-neuralgia/10201781732138503/.
"Revolutionary Pain Therapy," Nov. 13, 2013, video available at https://www.facebook.com/178787878873891/videos/treatment-for-migraines-and-trigeminal-neuralgia/10201781732138503/.
Transcript of News Story, Jul. 7, 2014, video available at: https://www.facebook.com/178787878873891/videos/681870651898942/.
"New Therapy for Migraines," Jul. 7, 2014, video available at https://www.facebook.com/178787878873891/videos/treatment-for-migraines-and-trigeminal-neuralgia/10201781732138503/.
Transcript of Webinar, Apr. 10, 2013, video available at: https://www.anymeeting.com/WebConference/RecordingDefault.aspx?c_psrid=ED57DC868548.
"A novel application to resolve migraine headaches—A Functional Neurology forum," Apr. 10, 2013, video available at: https://www.anymeeting.com/WebConference/RecordingDefault.aspx?c_psrid=ED57DC868548.
Ultimate Ears. Ultimate Ears Custom In-Ear Monitors. Website, http://pro.ultimatears.com, originally downloaded Feb. 27, 2014, 3 total pages.
Von Korff, et al., "Assessing headaches severity. New Directions", Jul. 1994 (Year: 1994).
Westone. Occupational Earpieces. Website, http://www.westone.com, originally downloaded Feb. 27, 2014, 2 total pages.
Wikipedia. Microcurrent electrical neuromuscular stimulator. Website, http://en.wikipedia.org, originally downloaded Feb. 27, 2014, 3 total pages.
Wikipedia. Somatosensory evoked potential. Website, http://en.wikipedia.org, originally downloaded Feb. 27, 2014, 5 pages total.
Wikipedia. Transcutaneous electrical nerve stimulation. Website, http://en.wikipedia.org, originally downloaded Feb. 27, 2014, 5 pages total.
World Health Organization. Headache disorders. Website, http://www.who.int, originally downloaded Feb. 27, 2014, 4 total pages.
Berthold Langguth, Verena Hund, Volker Busch, et al., "Tinnitus and Headache," BioMed Research International, vol. 2015, Article ID 797416, 7 pages, 2015. https://doi.org/10.115/2015/797416 (Year: 2015) in 7 pages.
Doherty, Colleen. "The Link Between Migraines and Tinnitus". Verywell Health, Nov. 23, 2019, https://www.verywellhealth.com/link-between-migraines-and-tinnitus-4077631#citation-10 (Year: 2019) in 4 pages.
Frangos E, Ellrich J, Komisaruk B. Non-invasive access to the vagus nerve central projections via electrical stimulation of the external ear: fMRI evidence in humans. Brain Stimul. Dec. 6, 2014. 8(3), 624-636 in 13 pages.
Kanzara T, Hall A, Virk J, Leung B, Singh A. Clinical anatomy of the tympanic nerve: A review. World J Otorhinolaryngol. Nov. 2014; 4(4), 17-22 in 8 pages.
Kiyokawa J., Yamaguchi K, Okada R, Maehara T, Akita K. Origin, course and distribution of the nerves to the posterosuperior wall of the external acoustic meatus. Anat Sci Int. Mar. 2014; 89(4), 238-245.
Saunders R, Tympanic membrane sensation. Brain. 1985, 108, 378-404 in 18 pages.
Tekdemir I, Aslan A, Elhan A., A clinico-anatomic study of the auricular branch of the vagus nerve and Arnold's ear-cough reflex. Surg Raiol Anat. 1998. 20(4), 253-257 in 5 pages.
Tekdemir I, Aslan A, Tuccar E, He C, Elhan A, Deda H. An anatomical study of the tympanic branch of the glossopharyngeal nerve (nerve of Jacobson). Ann Anat. Aug. 1998; 180(4): 349-52 in 4 pages.

(56) References Cited

OTHER PUBLICATIONS

Widemar L, Hellstrom S, Schultzberg M, Stenfors LE. Autonomic innervation of the tympanic membrane. An immunocytochemical and histofluorescence study. Acta Otolaryngol. Jul.-Aug. 1985;100(1-2):58:65 in 9 pages.

* cited by examiner

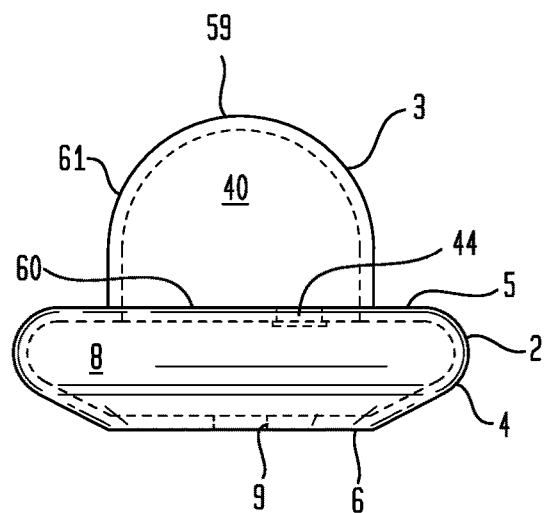
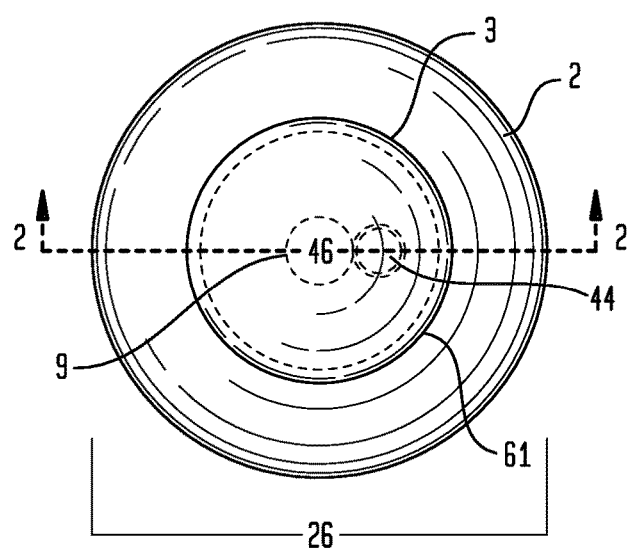
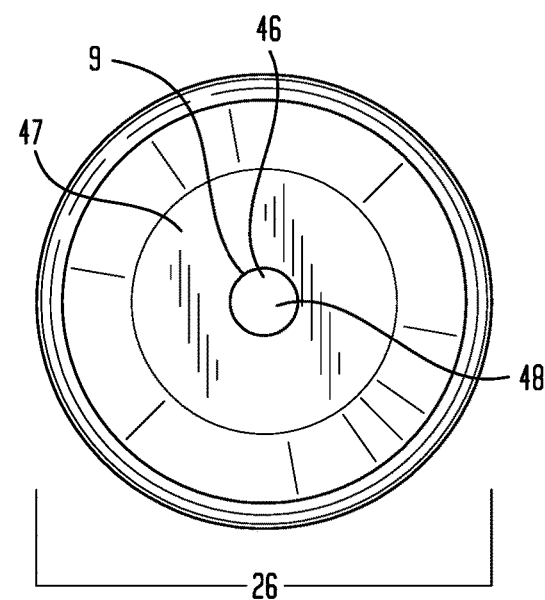

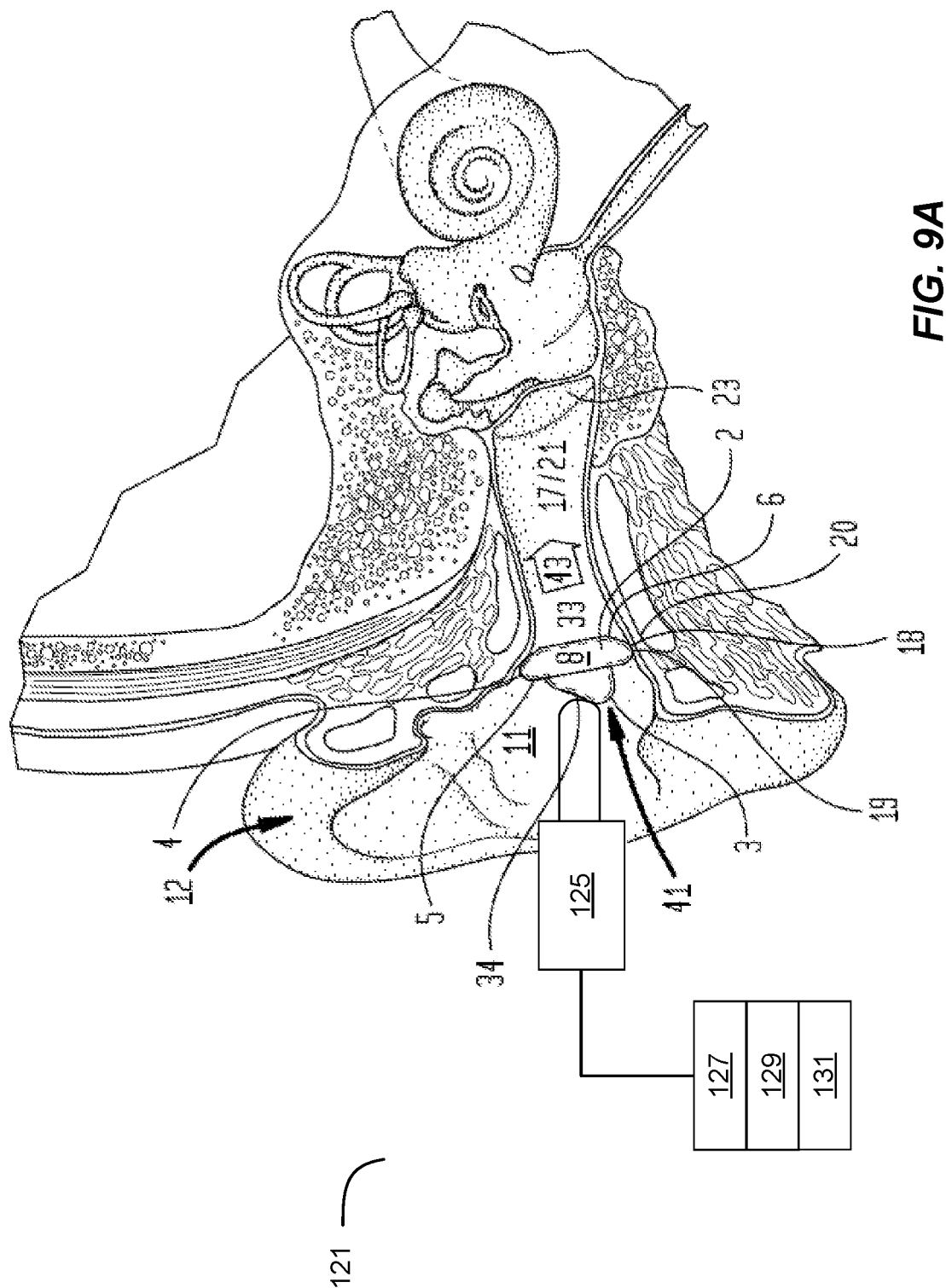

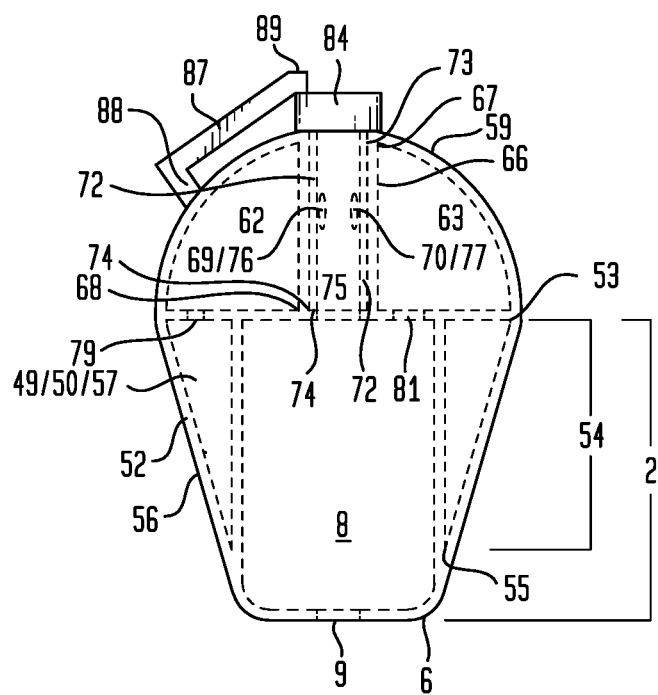
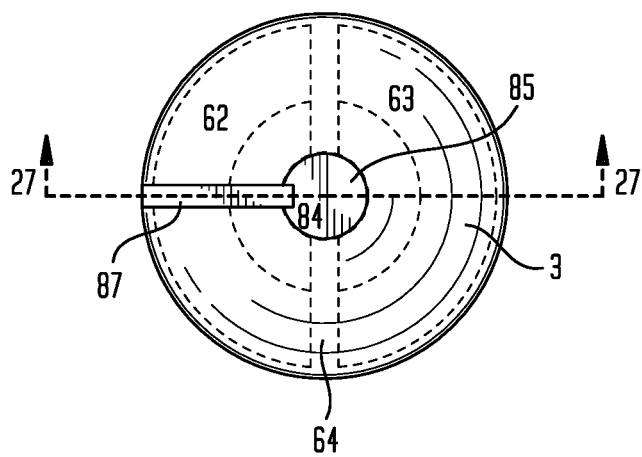
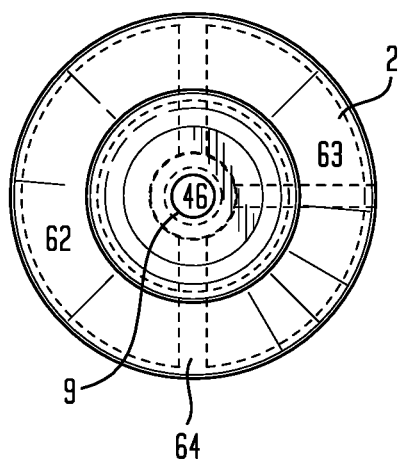

EAR PUMPS

CROSS-REFERENCE TO RELATED APPLICATIONS

This application is a continuation of International Application No. PCT/US2018/019981 designating the United States, with an international filing date of Feb. 27, 2018, and titled EAR PUMPS, which claims priority to and the benefit under 35 U.S.C. § 119(e) of U.S. Provisional Patent Application No. 62/464,102, filed Feb. 27, 2017, and titled MANUAL EAR-PUMP, the entirety of each of which is incorporated by reference herein and should be considered a part of this specification.

INCORPORATION BY REFERENCE

The following references are incorporated by reference in their entirety and made a part of this specification for all that they disclose:

U.S. Patent Application Publication No. 2015/0000678, published Jan. 1, 2015, and titled METHOD FOR EXTERNAL EAR CANAL PRESSURE REGULATION TO ALLEVIATE DISORDER SYMPTOMS; U.S. Patent Application Publication No. 2016/0151206, published Jun. 2, 2016, and titled EXTERNAL EAR CANAL PRESSURE REGULATION DEVICE; U.S. Pat. No. 9,039,639, issued May 26, 2015, and titled EXTERNAL EAR CANAL PRESSURE REGULATION SYSTEM; PCT Patent Application No. PCT/US2017/064964, filed Dec. 6, 2017, and titled SYSTEMS AND METHODS FOR TREATING NEUROLOGICAL DISORDERS; U.S. Patent Application Publication No. 2018/0023558, published Jan. 25, 2018, and titled MAGNETICALLY DRIVEN PRESSURE GENERATOR. Any of the embodiments and features disclosed herein can be provided or used in connection with any of the embodiments and features disclosed in any of the documents that are incorporated by reference herein.

BACKGROUND

Field of the Disclosure

Some embodiments disclosed herein relate to ear pumps, such as manual or automated ear pumps including one or more of a support element configured to releasably engage an auricle of an ear, a resilient element capable of being resiliently deformed coupled to a support element, and an aperture disposed on a support element bottom surface which aligns with an external ear canal upon disposing the support element in the auricle of the ear.

Description of the Related Art

Pain or discomfort associated with a disorder, including neurologically-mediated disorders such as craniofacial pain syndromes or headache syndromes, may negatively impact the quality of life of the sufferer. In addition to the burden upon the individual, chronic neurological conditions may be a significant strain upon family members, employers, and the healthcare system.

Regarding migraine headaches, concomitant symptoms such as pain, nausea, aura, photophobia, dysesthesias, dizziness, vertigo, and dysequilibrium may represent a significant burden to the population. Epidemiological studies indicate that, in the United States, approximately 18% of women and 6% of men experience frequent migraine headaches and 2% of the general population suffer from chronic migraine headaches. Additionally, persons suffering with chronic migraine headaches or other headaches of similar severity and disability may be at a significantly greater risk for depression and attempted suicide. Thus, it is prudent for clinicians and researchers to continue searching for effective devices and methods to alleviate the symptoms associated with these disorders or to treat the disorders.

Standard pharmaceutical therapies for migraine headaches may generally be prescribed to prevent pain or to relieve pain. The various agents which fall under these two broad categories may exhibit a wide range of effectiveness and also incur varying degrees of side effects. From the perspective of economics, the expense of these medications may be a major source of financial burden on the consumer. Moreover, advanced interventions such as botulinum toxin injections, nerve blockades, neurosurgical alterations, and implanted electrical stimulators may significantly increase costs associated with treatment, while subjecting patients to potential changes in their anatomy and physiology, with no guarantee of complete or permanent symptomatic relief or disorder resolution.

SUMMARY

Certain example embodiments are summarized below for illustrative purposes. The embodiments are not limited to the specific implementations recited herein. Embodiments may include several novel features, no single one of which is solely responsible for its desirable attributes or which is essential to the embodiments.

There is a burgeoning field of understanding and applications within the neurosciences which seek to affect positive physiological changes in the nervous system through non-pharmaceutical and non-surgical applications. This field of 'functional neurology' views the human nervous system as a receptor driven system, which may be activated and stimulated in specific ways to produce adaptive, long-term changes through the process of neuroplasticity. This approach to neurorehabilitation utilizes, but not necessarily exclusively includes, various forms and patterns of receptor activation or deactivation to promote positive neurophysiological adaptations within the central nervous system, including the brain, brainstem, and spinal cord, which may promote physiological function of associated tissues, organs, and systems.

There would be a substantial advantage in providing a device or methods which can generate one or more stimuli which can alleviate one or more symptoms associated with a disorder, such as craniofacial pain syndromes or headache syndromes, or treat one or more disorders.

Particular embodiments of the subject matter described in this specification can be implemented so as to realize one or more of the following advantages. A treatment device is described that can treat neurological disorders, such as to safely eliminate, or reduce an intensity or frequency of, pain associated with headaches, which can include pain of the head or neck, and can optionally include pain not caused by underlying diseases or structural problems, such as primary headaches (e.g., migraines, cluster headaches, tension-type headaches, and so on). As will be described, the treatment device can manipulate pressure associated with one or more ears of a patient, such as manipulating pressure in an external ear canal of an ear (e.g., moving the tympanic membrane). The treatment device can utilize pressure profiles, for instance specific patterns of pressure applied to an ear (e.g., time series of pressure values), that are determined to reduce headache pain of individual users.

Accordingly, a broad object of the disclosure can be to provide an ear pump, such as a manual ear pump, including one or more of a support element configured to releasably engage to an external ear canal, a resilient element coupled to a support element and capable of being deformed, an interior space defined by the resilient element and the support element, and an aperture disposed on the support element bottom.

Another broad object of the disclosure can be to provide a method of making an ear pump, such as a manual ear pump, including configuring a support element to releasably engage an external ear canal, coupling a resilient element capable of being deformed to a support element defining an interior space by the resilient element and the support element, and disposing an aperture on the support element bottom.

Another broad object of the disclosure can be to provide a method of using an ear pump, such as a manual ear pump, including one or more of obtaining an ear pump, such as a manual ear pump, including one or more of a support element configured to releasably engage to an external ear canal, a resilient element coupled to a support element and capable of being resiliently deformed, an interior space defined by the resilient element and the support element, and an aperture disposed on the support element bottom, forcibly urging a resilient element to cause a fluid to flow from the interior space to the external ear canal, and removing the forcible urging to cause a fluid to flow from the external ear canal to the interior space.

Various embodiments can relate to an ear pump, which can include a resilient element capable of being resiliently deformed. The resilient element can have a compressed state and an uncompressed state. The ear pump can include a support element configured for insertion into the external ear canal, and the support element can include a fluid flow pathway, an opening for fluid to flow between the fluid flow pathway and the external ear canal, and one or more vesicle cavities. The ear pump can include a valve having a first state to permit fluid flow between the resilient element and the one or more vesicle cavities while impeding fluid flow between the resilient element and the fluid flow pathway, and a second state to permit fluid flow between the resilient element and the fluid flow pathway while impeding fluid flow between the resilient element and the one or more vesicle cavities.

The valve can have a third state to permit fluid flow between the resilient element and the fluid flow pathway and to also permit fluid flow between the resilient element and the one or more vesicle cavities. The valve can have a fourth state to impede fluid flow between the resilient element and the fluid flow pathway and to also impede fluid flow between the resilient element and the one or more vesicle cavities. The valve can include a rotation element, and rotation of the rotation element can change the valve between the first state and the second state. The valve can include a tubular conduit having a first tubular conduit aperture and a second tubular conduit aperture, and a tubular member having a first tubular member and a second tubular conduit aperture. The tubular member can be rotatable relative to the tubular conduit. The tubular member can be positioned to align the first tubular member aperture with the first tubular conduit aperture and to not align the second tubular member aperture with the second tubular conduit aperture when the valve is in the first state. The tubular member can be positioned to align the second tubular member aperture with the second tubular conduit aperture and to not align the first tubular member aperture with the first tubular conduit aperture when the valve is in the second state. The tubular member can be positionable to align the first tubular member aperture with the first tubular conduit aperture and to also align the second tubular member aperture with the second tubular conduit aperture to permit fluid flow between the resilient member and both the fluid flow pathway and the one or more vesicle cavities. The tubular member can be positionable to not align the first tubular member aperture with the first tubular conduit aperture and to also not align the second tubular member aperture with the second tubular conduit aperture to impede fluid flow between the resilient member and both the fluid flow pathway and the one or more vesicle cavities.

The one or more vesicle cavities can be expandable, which in some embodiments can facilitate sealing of the support element with the external ear canal. When the valve is in the first state, compression of the resilient member to the compressed state can cause fluid to flow into the one or more vesicle cavities to expand the one or more vesicle cavities and/or decompression of the resilient member to the uncompressed state causes fluid to flow out of the one or more vesicle cavities. The ear pump can be a manual ear pump. The ear pump can be configured to not extend beyond the auricle of the ear and the external ear canal. The ear pump can be contained within the auricle of the ear and/or the external ear canal. The resilient element and the support element can be made of the same material. The resilient element and the support element can be integrally formed as single piece. A wall can separate the resilient element from the support element. The wall can include a first aperture that provides fluid communication through the wall to the one or more vesicle cavities, and the wall can include a second aperture that provides fluid communication through the wall to the fluid flow pathway.

The ear pump can include an actuator for pressing the resilient element and a controller for operating the actuator. The ear pump can include an actuator for changing the valve between the first state and the second state and a controller for operating the actuator. The controller can include one or more computer processors. The controller can execute instructions stored on computer-readable memory.

Various embodiments disclosed herein can relate to an ear pump, which can include a support element that is configured to engage an ear of a subject without extending into the external ear canal of the ear. The ear pump can include a resilient element in fluid communication with the support element.

Compression of the resilient element can drive fluid out of the ear pump. The support element can be configured to engage a concha bowl of the ear. The ear pump can include a piston.

Various embodiments disclosed herein can relate to an ear pump, which can include a support element configured to be inserted into the external ear canal, and a piston configured to slidably move relative to the support element. At least a portion of the piston can enter the external ear canal. The ear pump can include an actuator for moving the piston and a controller for operating the actuator.

Various embodiments disclosed herein can relate to a method of treating a neurological disorder. The method can include inserting an ear pump into the ear of a subject experiencing the neurological disorder. The ear pump can include a fluid flow generator positioned in the ear. The method can include operating the fluid flow generator to produce a pressure differential between an external ear canal pressure and the ambient pressure. The pressure differential can be effective to treat the neurological disorder.

The neurological disorder can include a migraine headache. The neurological disorder can include facial or cranial pain. Operating the fluid flow generator can include manually pressing a resilient element with a finger. Operating the fluid flow generator can include sending a command to a computer controlled actuator. The fluid flow generator can include a resilient element having a compressed state and an uncompressed state. The fluid flow generator can include a piston. The ear pump can include one or more check valves. In some cases, the ear pump does not extend into the external ear canal. The ear pump can engage a concha bowl of the ear. The ear pump can include an attachment feature configured to wrap around the ear. The ear pump can include a headband to provide support to the ear pump. The ear pump can be contained within the external ear canal and auricle of the ear. The ear pump can be contained within the ear canal and concha bowl of the ear. In some embodiments, the ear pump does not include a flexible tube.

The method can include heating the ear pump before inserting the ear pump into the ear. The method can include cooling the ear pump before inserting the ear pump into the ear.

Various embodiments disclosed herein can relate to an ear pump. The ear pump can include a support element having a support element peripheral wall which joins a support element top in opposed spaced apart relation to a support element bottom. The support element can have a support element internal surface defining a support element interior chamber and a support element external surface which releasably engages an auricle of an ear. The ear pump can include a resilient element coupled to said support element. The resilient element can be capable of being resiliently deformed. The ear pump can include a support element bottom aperture element disposed in said support element bottom. The aperture element can be aligned with an external ear canal opening upon disposing said support element in said auricle of said ear. The ear pump can be a manual ear pump.

Various embodiments disclosed herein can relate to a method of making an ear pump. The method can include configuring a support element peripheral wall to join a support element top in opposed spaced apart relation to support element bottom. The support element can have a support element internal surface defining a support element interior chamber and a support element external surface which can releasably engage an auricle of an ear. The method can include coupling a resilient member to said support element. The resilient element can be capable of being resiliently deformed. The method can include disposing an aperture on a support element bottom. The aperture element can be aligned with an external ear canal opening upon disposing said support element in said auricle of said ear. The ear pump can be a manual ear pump.

Various embodiments disclosed herein can relate to a method of using an ear pump. The method can include obtaining an ear pump, which can include a support element having a support element having a support element peripheral wall which joins a support element top in opposed spaced apart relation to support element bottom. The support element can have a support element internal surface defining a support element interior chamber and a support element external surface releasably engagable in an auricle of an ear. The ear pump can have a resilient element coupled to said support element. The resilient element can be capable of being resiliently deformed. The ear pump can include a support element bottom aperture element disposed in said support element bottom. The method can include sealably engaging said support element external surface with said auricle of said ear with said support element bottom aperture element adjacent an external ear canal opening. The method can include forcibly urging said resilient element to generate a flow of fluid in said interior chamber of said support element and through said support element bottom aperture toward said external ear canal. The method can include removing said forcible urging to generate a flow of fluid in said external ear canal toward said interior chamber of said support element.

Various embodiments can relate to an ear pressure regulation system, which can include a fluid flow generator, an earpiece for insertion into the external ear canal, where the earpiece has a fluid flow pathway through the earpiece for providing fluid flow to or from the external ear canal. The system can have an expandable vesicle and a valve having a first state and a second state. The first state can permit fluid flow between the fluid flow generator and the expandable vesicle. The second state can permits fluid flow between the fluid flow generator and the fluid flow pathway to provide fluid flow to or from the external ear canal.

Naturally, further objects of the embodiments are disclosed throughout other areas of the specification, drawings, photographs, and/or claims. The details of one or more embodiments of the subject matter of this specification are set forth in the accompanying drawings and the description below. Other features, aspects, and advantages of the subject matter will become apparent from the description, the drawings, and from the claims.

BRIEF DESCRIPTION OF THE DRAWINGS

Certain embodiments will be discussed in detail with reference to the following figures, wherein like reference numerals refer to similar features throughout. These figures are provided for illustrative purposes and the embodiments are not limited to the specific implementations illustrated in the figures.

FIG. 3 is a side elevation view of a particular embodiment of the ear pump.

FIG. 4 is a top plan view of a particular embodiment of the ear pump.

FIG. 5 is a bottom plan view of a particular embodiment of the ear pump.

FIG. 9A is a cross-sectional view showing an example embodiment of an actuator operating an ear pump.

FIG. 28 is a side elevation view of the particular embodiment of the ear pump.

FIG. 29 is a top plan view of the particular embodiment of the ear pump.

FIG. 30 is a bottom plan view of the particular embodiment of the ear pump.

DETAILED DESCRIPTION OF CERTAIN EMBODIMENTS

Figure 1:
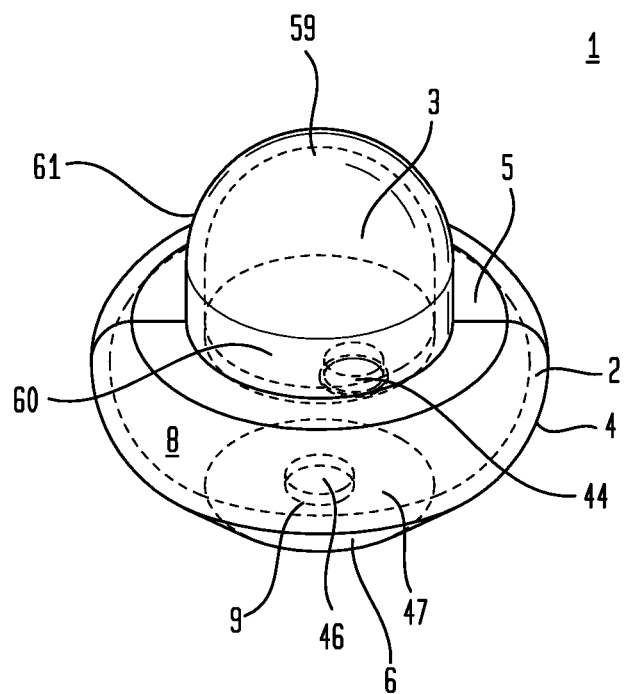
FIG. 1 is a perspective view of a particular embodiment of an ear pump, which can be a manual ear pump.

Aspects of this disclosure relate to embodiments of systems and methods that can be used for treating medical conditions, such as neurological disorders and/or symptoms thereof (e.g., migraine headaches, other types of headaches, facial pain, pain in other body portions, dizziness, nausea, seizures, etc.). A treatment system may be used to reduce or alleviate symptoms of one or more conditions or symptoms experienced by a user (e.g., pain). For instance, an example treatment device can be configured to provide a fluid flow to or from the ear of a patient and/or to apply pressure to an external ear canal of a patient. In some embodiments, a portion of the treatment device (e.g. an ear pump) can be placed inside an ear cavity (e.g., in the external ear canal) of a user. Various treatment devices and methods discussed in this application should be understood to use any suitable type of fluid flow generator that accomplishes or facilitates storage or transfer of fluid to an ear cavity of a user. The present application includes a number of embodiments of earpieces (e.g., ear pumps), which can be used for treatment of medical conditions. Though one or more figures may show an earpiece of a particular embodiment, it should be understood that other suitable earpieces can be used, even though not specifically discussed in each case for sake of brevity. Additional details regarding the medical conditions that can be treated and the procedures that can be performed using the ear pumps (1) disclosed herein are provided in the documents that are incorporated by references, including at least PCT Patent Application No. PCT/US2017/064964.

Referring generally to FIGS. 1 through 9, particular embodiments of a manual ear pump (1) can include one or more of a support element (2) and a resilient element (3). The support element (2) can include a support element peripheral wall (4) which joins a support element top (5) in opposed spaced relation to a support element bottom (6). The support element (2) can have a support element internal surface (7) which defines a support element interior chamber (8). A support element bottom aperture element (9) can be disposed in the support element bottom (6) communicating between the support element external surface (10) and the support element internal surface (7). The support element external surface (10) bounded by the support element peripheral walls (4) can be reconfigured to be disposed and releasably retained in the concha bowl (11) of an ear (12).

The concha bowl (11) can refer to the anatomical area of an ear (12) defined by the antihelix (13), tragus (14), antitragus (15), and concha (16). In particular embodiments, the support element peripheral wall (4) can outwardly taper approaching the support element bottom (6) to allow the support element bottom (6) to be positioned adjacent the external ear canal (17) upon disposing the support element (2) in the concha bowl (11) of the ear (12). The support element (2) when disposed in the concha bowl (11) can deform to reconfigure the support element external surface (10) and the volume of the interior chamber (8) to achieve a substantially impermeable seal (18) between the support element bottom peripheral margin (19) and the concha bowl (11) proximate the external ear canal opening peripheral margin (20).

The external ear canal (17) can refer to the portion of the ear canal (21) (or auditory canal) communicating between the auricle (22) of the ear (12) and the tympanic membrane (23). The term impermeable seal (18) can refer to a seal between the support element bottom peripheral margin (19) and the external ear canal opening peripheral margin (20) sufficiently leak tight to allow operation of the manual ear pump (1) to generate and maintain a pressure differential between the ambient atmosphere outside the external ear canal (17) and the volume defined by the external ear canal (17) during normal use of the manual ear pump (1).

While the embodiment of the support element (2) shown in FIGS. 1 through 9 has a substantially flat support element top (5) radially extending outward to join a curved support element peripheral wall (4) which outwardly tapers approaching a substantially flat support element bottom(6), this example is not intended to preclude other configurations of the support element (2), which can be disposed in and reconfigured to generate the substantially impermeable seal (18) with external ear canal opening peripheral margin (20).

Now referring primarily to FIGS. 10 through 17, particular embodiments of the manual ear pump (1) can include a support element (2) having an elongate tubular wall (24) disposed between the support element peripheral wall (4) and the support element bottom (6). The elongate tubular wall (24) can have a length (25) which disposes the support element bottom (6) inside of the external ear canal (17) when the support element peripheral wall (4) engages the concha bowl (11).

Again, referring primarily to FIGS. 10 through 14, the support element (2) can have a support element peripheral wall (4) of greater diameter (26) than the diameter (27) of the external ear canal opening (28) or than the elongate tubular wall (24). The diameter (26) of the support element (2) can be greater than the diameter of the resilient element (3). The elongate tubular wall (24) can have a diameter which allows insertion into the external ear canal (17) and having a length (25) less than the length (29) of the external ear canal (17). The diameter of the elongate tubular wall (24) can engage surfaces of the external ear canal (17) to assist in achieving a substantially impermeable seal (18). As to particular embodiments the elongate tubular wall (24) can taper approaching the support element bottom (6). While the Figures illustrate a generally cylindrical elongate tubular element (30), this illustrative configuration is not intended to preclude other cross-sectional configurations of the elongate tubular wall (24), such as: hexagonal, pentagonal, octagonal, or other polygonal cross-sectional area, an ovoid or elliptical cross-sectional area, or other like configuration.

Figure 19:
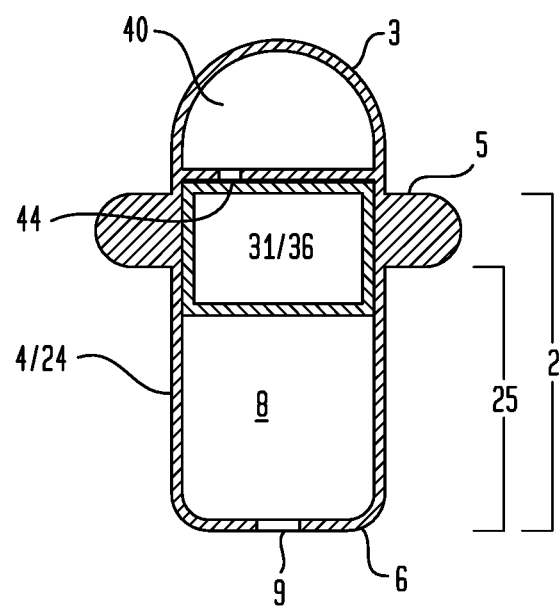
FIG. 19 is a cross-sectional view 19-19 of the particular embodiment of the ear pump releasably retained in an ear.

Now referring primarily to FIGS. 18 through 25, particular embodiments of the manual ear pump (1) can further include a piston (31) disposed in the interior chamber (8) of the support element (2) slidingly engaged to the internal surface (32) of the elongate tubular wall (24). The piston (31) can be reciprocally oscillated within the interior chamber (8) of the support element (2) in response to the movement of a fluid (33) generated by the deformation (34) and reformation (35) of the resilient element (3). FIG. 19 illustrates an embodiment having a piston (31) configured as a cylinder (36) which slidingly engages the internal surface (32) of the elongate tubular wall (24). As to these embodiments, the elongate tubular wall (24) has sufficient rigidity to allow the piston (31) to travel from a first location inside the interior chamber (8) proximate the support element top (5) toward the support element bottom (6).

Again, referring primarily to FIGS. 1 through 25, particular embodiments of a manual ear pump (1) can include a resilient element (3) coupled to the support element top (5). The resilient element (3) includes a resiliently flexible wall (37) having a wall external surface (38) and a wall internal surface (39). The wall external surface (38) can be configured in any manner which allows deformation (34) of the resiliently flexible wall (37) (as shown in the examples of FIGS. 8, 16, 24 and 32). The wall internal surface (39) can define a resilient element internal space (40). The resiliently flexible wall (37) in a deformed condition (41) (as shown in the examples of FIGS. 8, 16, 24 and 32) can decrease the internal space (40), and in return toward a non-deformed condition (42) (as shown in the example of FIGS. 9, 17, 25, and 33), can increase the volume of the internal space (40). The change in the volume of the internal space (40) can generate a fluid flow (43) between the resilient element (3) and the support element bottom aperture element (9). As to other embodiments, configurations of the wall external surface (38) and the corresponding wall internal surface (39) of the resilient element (3) can, but need not necessarily, include a generally hemispherical configuration as shown in the examples of FIGS. 1, 10, 18 and 25; however, this is not intended to preclude configurations of the wall external surface (38) which are irregular in configuration such as bladder, or other regular configurations such as a cylinder, accordion shape, etc.

Now referring primarily to FIGS. 10 through 14 and 18 through 22, in particular embodiments, the fluid flow (43) generated by deformation (34) and reformation (35) of the resilient element (3) can pass directly from the resilient element (3) through the support element bottom aperture element (9) in the support element bottom (6), although the embodiments of FIGS. 1 to 5 can be modified to include this feature. As to other embodiments, as shown in FIGS. 1 through 5 and 18 through 22, the support element top (5) can be disposed between the resilient element (3) and the support element bottom (6), although the embodiments of FIGS. 10 to 14 can be modified to include this feature. As to these embodiments, the support element top (5) can further include a support element top aperture element (44) communicating between the interior space (40) of the resilient element (3) and the resilient element interior space (40) which allows the fluid flow (43) generated by deformation (34) and reformation (35) of the resilient element (3) to pass through the support element top aperture element (44) and the support element bottom aperture element (9). In particular embodiments the support element top aperture element (44) can further include an aperture valve (45) which allows the fluid flow (43) to egress from the support element bottom aperture element (9) but restricts or prohibits ingress of a fluid flow (43) through the support element bottom aperture element (9) toward the resilient element (3). Many other valve configurations are possible, as discussed herein.

The resilient element (3), in some embodiments, may comprise a conduit to in fluid communication with the atmosphere. The conduit can comprise a one-way valve that permits fluid flow ingress into the interior space (40) but prevents fluid flow egress through the one-way valve from the interior space (40). In this manner, the ear-pump (1) may be configured to apply fluid flow and, consequently, positive pressure to an external ear canal of a user when the resilient element (3) undergoes deformation and/or is actuated. As the resilient element (3) is disengaged and/or underdoes reformation, the interior space (40) may receive air from the external atmosphere to apply additional fluid flow and positive pressure to the ear canal.

Alternatively, the configurations of the aperture valve (45) and the one-way valve may be reversed to provide for fluid flow away from the external ear canal. In this manner, the ear-pump (1) may be configured to apply negative pressure the external ear canal of the user. For example, the aperture valve (45) the support element top aperture element (44) may allow the fluid flow to ingress from the support element bottom aperture element (9) towards the interior space (40) but restricts or prohibits egress of a fluid flow through the support element bottom aperture element (9) from the resilient element (3). The conduit of the resilient element (3), in some instances, may be in fluid communication with the atmosphere and the interior space (40). The conduit can comprise a one-way valve that permits fluid flow egress from the interior space (40) towards the atmosphere but prevents fluid flow ingress through the one-way valve towards the interior space (40). In this manner, the ear-pump (1) may be configured to permit fluid flow away from an external ear canal and, consequently, apply negative pressure to the external ear canal when the resilient element (3) undergoes reformation and/or is disengaged. As the resilient element (3) is engaged and/or underdoes deformation, the interior space (40) may expel air to the external atmosphere. Furthermore, as the resilient element (3) is disengaged and/or underdoes reformation, the interior space (40) may receive air from the external ear canal to apply negative pressure to the ear canal.

In some cases, the ear pump (1) can be a single use item. Pressing the resilient element (3), as shown for example in FIG. 8, can cause the resilient element (3) to deform and transition to a compressed state. The resilient element internal space (40) in the compressed state can have a smaller volume than in the uncompressed state. Pressing the resilient element (3) can cause fluid (e.g., air) to flow out of the resilient element internal space (40) through the aperture (44) and the valve (45). Pressing the resilient element (3) can cause fluid (e.g., air) to flow out of the bottom aperture (9), and into the external ear canal, which can increase a pressure differential between the external ear canal pressure and ambient pressure. The ear pump (1) can be used to produce a positive pressure differential, with the pressure in the external ear canal being higher than the ambient pressure outside the ear. The valve (45) can be a one-way valve or check valve. When the resilient element (3) is released, the valve (45) can impede fluid from flowing into the resilient element internal space (40). The resilient element (3) can remain in the compressed state when released. Accordingly, the pressure differential between the external ear canal pressure and ambient pressure can be maintained when the resilient element (3) is no longer being pressed. The pressure differential can eventually be released by removing the ear pump (1) from the ear.

Figure 8:
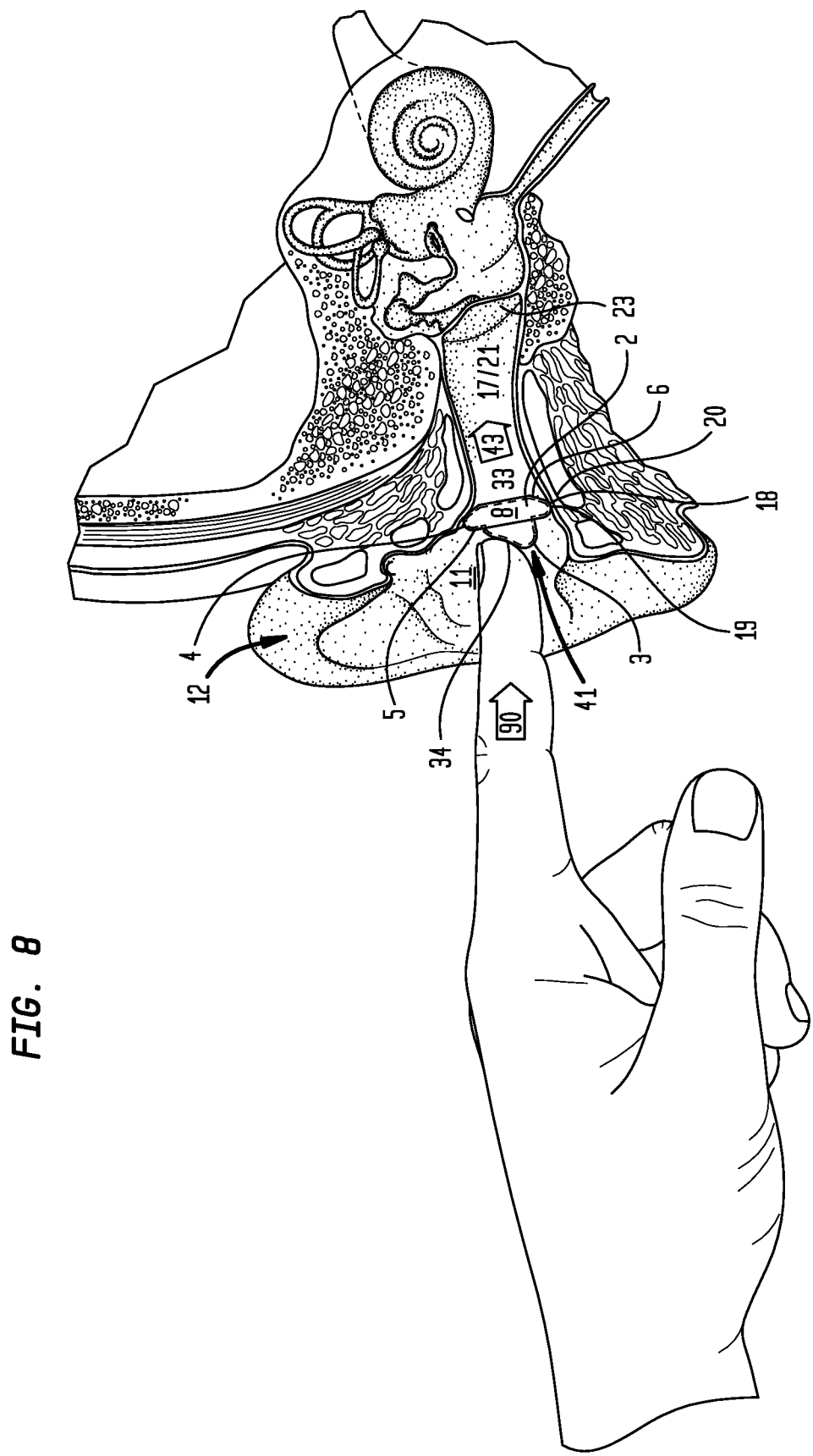
FIG. 8 is a cross-sectional view through the anatomy of the ear showing a method of using the particular embodiment of the ear pump shown in FIG. 1 releasably retained in the auricle of the ear.
Figure 9:
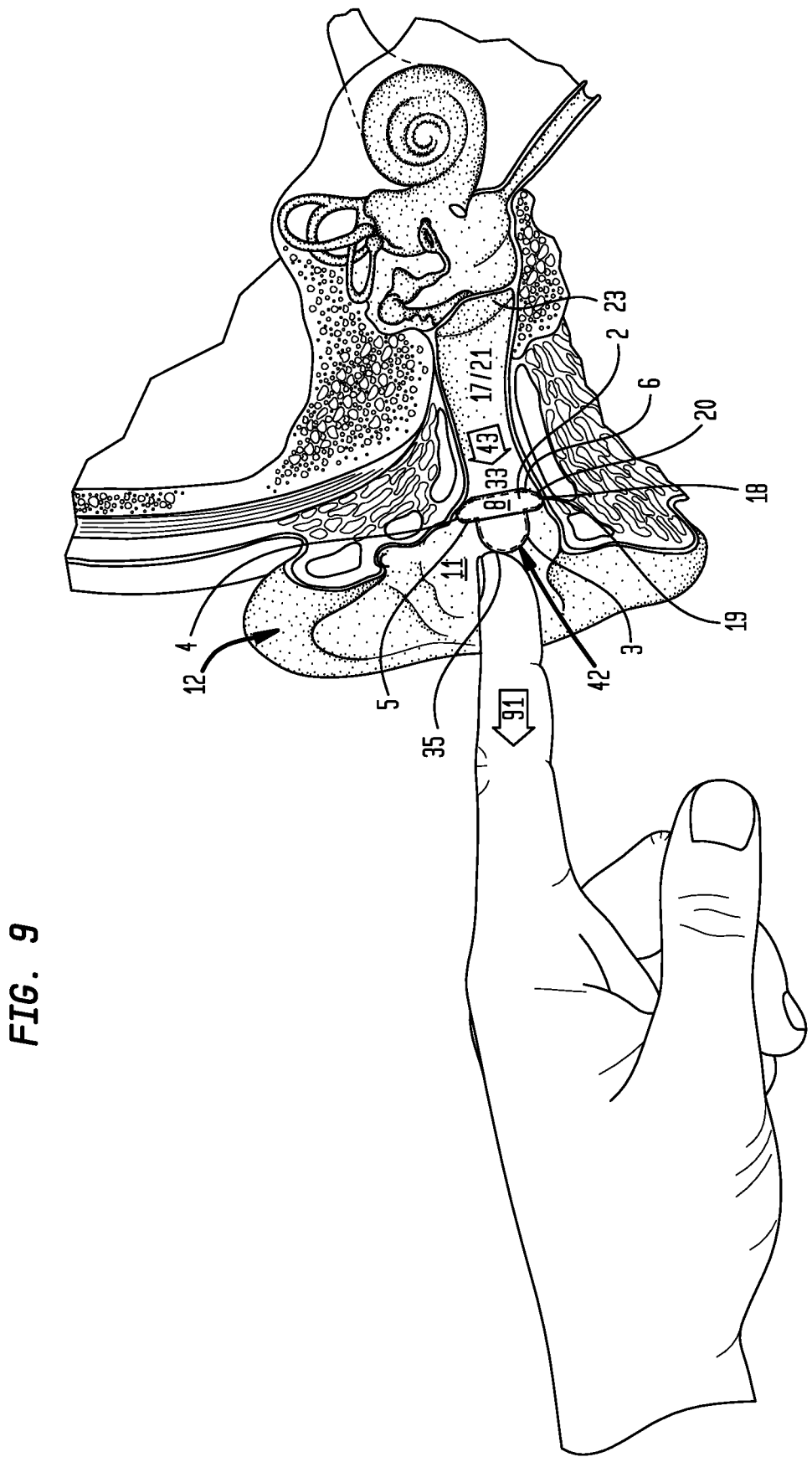
FIG. 9 is a cross-sectional view through the anatomy of the ear showing a method of using the particular embodiment of the ear pump shown in FIG. 1 releasably retain in the auricle of the ear.
Figure 10:
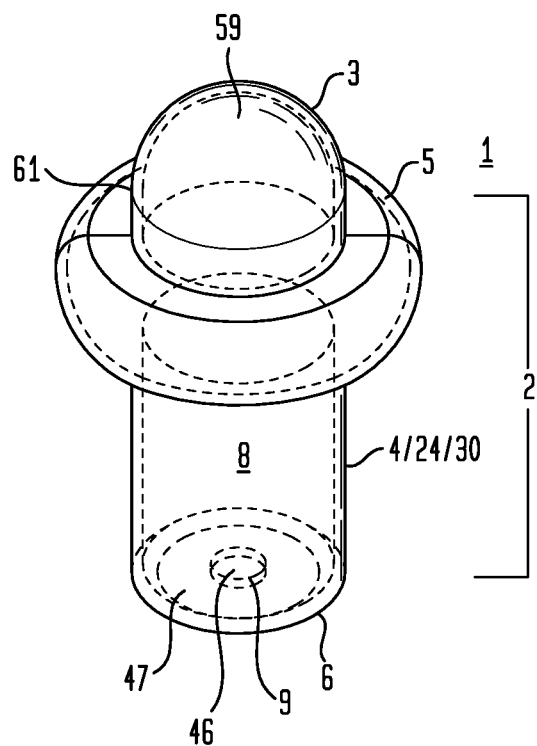
FIG. 10 is a perspective view of another particular embodiment of an ear pump.
Figure 11:
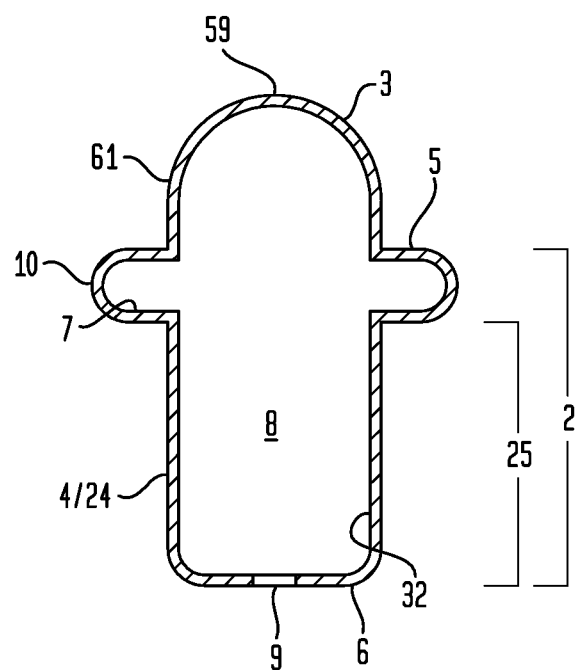
FIG. 11 is cross-sectional view 11-11 of the particular embodiment of the ear pump shown in FIG. 10.
Figure 12:
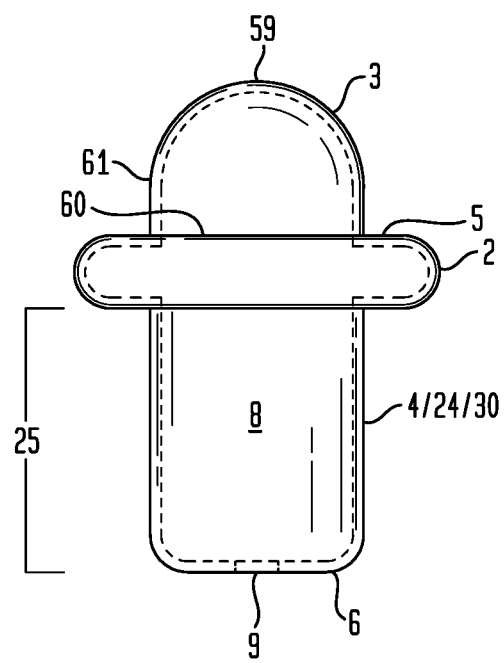
FIG. 12 is a side elevation view of the particular embodiment of the ear pump.
Figure 13:
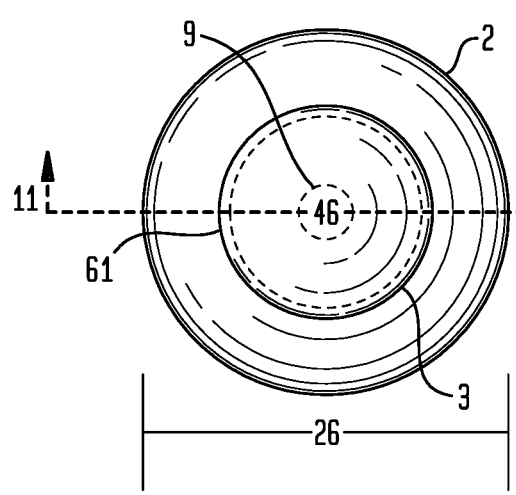
FIG. 13 is a top plan view of the particular embodiment of the ear pump.
Figure 14:
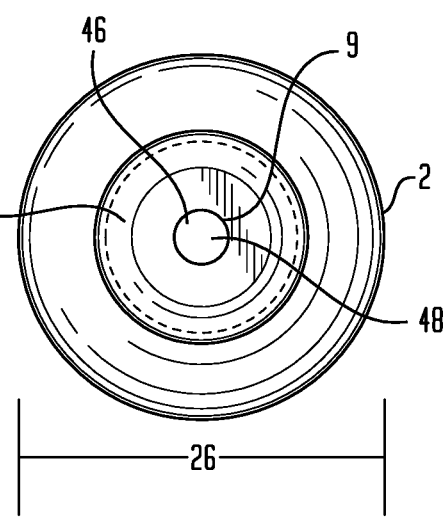
FIG. 14 is a bottom plan view of the particular embodiment of an ear pump.
Figure 16:
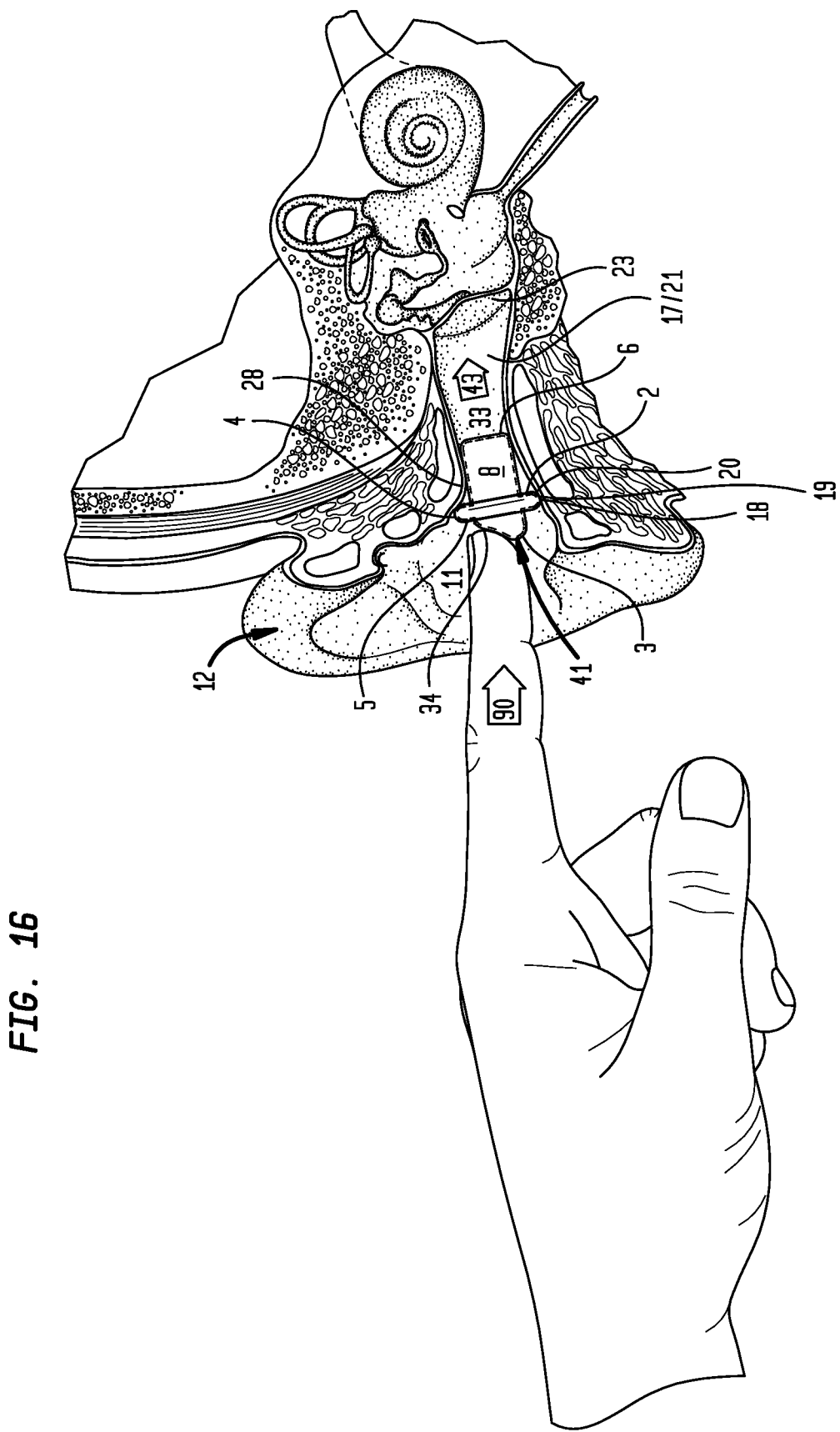
FIG. 16 is a cross-sectional view of the anatomy of the ear showing a method of using the particular embodiment of the ear pump releasably retained in the auricle of the ear.
Figure 17:
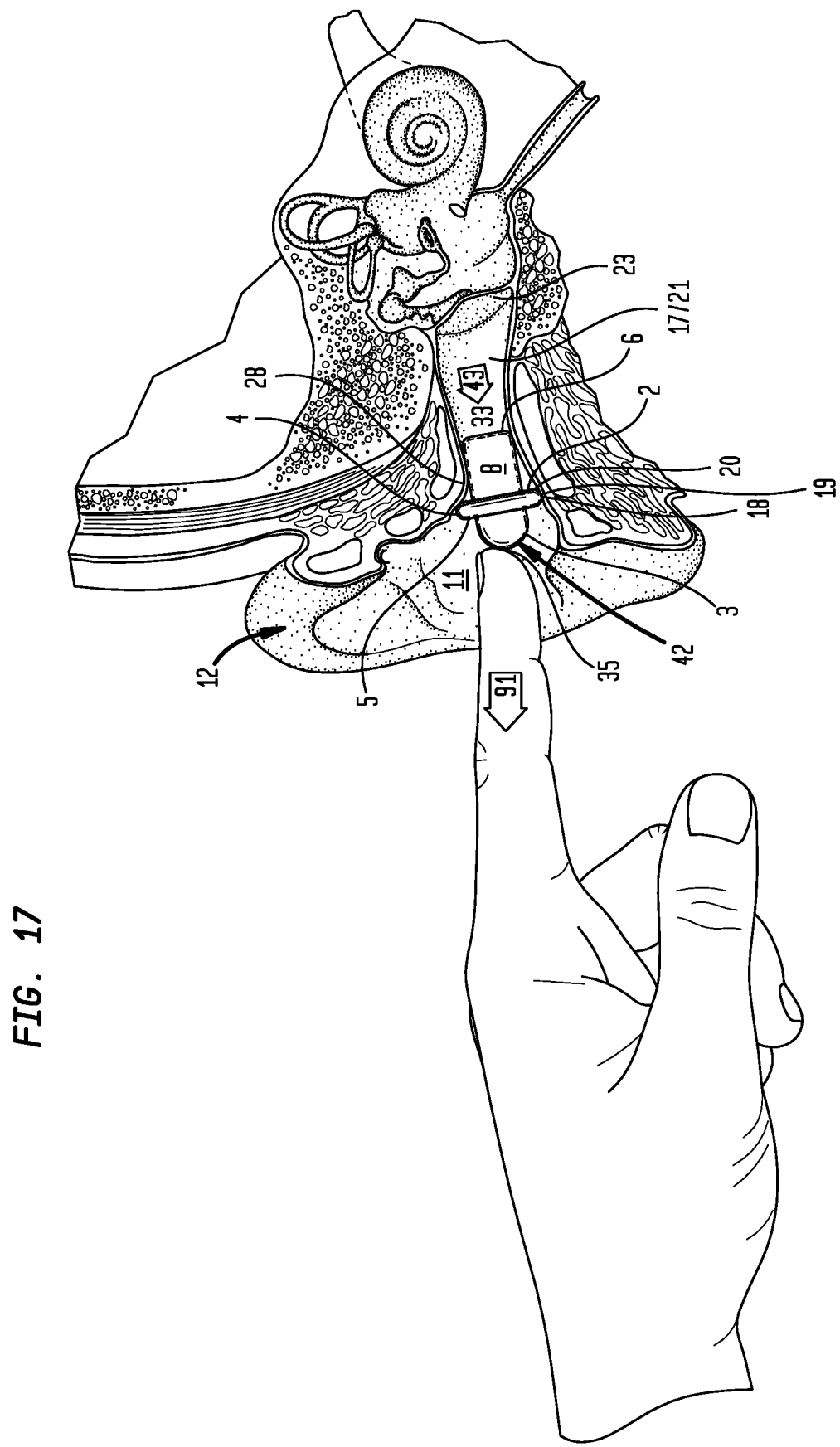
FIG. 17 is a cross-sectional view of the anatomy of the ear showing a method of using the particular embodiment of the ear pump.
Figure 18:
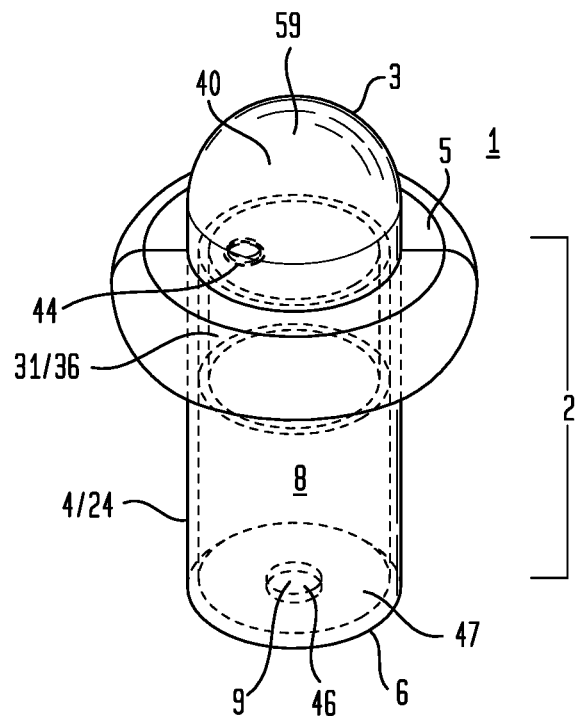
FIG. 18 is a perspective view of another particular embodiment of an ear pump.

In some embodiments, the valve (45) can be omitted. Pressing the resilient element (3), as shown in FIGS. 8 and 16, can cause fluid to flow out of the aperture (9) and into the external ear canal. Releasing the resilient element (3), as shown in FIGS. 9 and 17, can cause fluid to flow in through the aperture (9) and into the resilient element internal space (40) as the resilient element (3) resiliently transitions from the compressed state to the uncompressed state. The ear pump (1) can be used to modulate a pressure differential between the external ear canal pressure and ambient pressure. For example, the ear pump (1) can be used to modulate a positive pressure differential. The ear pump (1) can be placed in the ear with the resilient element (3) in the uncompressed state. With the ear pump (1) in the ear, pressing and compressing the resilient element (3) can increase the pressure in the external ear canal, to produce a positive pressure differential relative to ambient pressure. Releasing the resilient element (3) can cause reduce the pressure in the external ear canal back towards ambient pressure. Accordingly, the ear pump (1) can be used to produce pulses of positive pressure in the external ear canal (17), such as by repeatedly pressing and releasing the resilient element (3). A sustained positive pressure differential can be produced by pressing and holding the resilient element (3) in the compressed state for a sustained period of time.

The ear pump (1) can be used to produce and/or modulate a negative pressure differential between the external ear canal (17) and ambient pressure. The resilient element (3) of the ear pump (1) can be pressed to the compressed state before insertion into the ear. Upon release of the resilient element (3) fluid can be drawn from the external ear canal (17) into the air pump (1) as the resilient element (3) resiliently returns towards the uncompressed state, as shown for example in FIGS. 17 and 25. This can produce a negative pressure differential with a reduced pressure in the external ear canal as compared to ambient pressure. Pressing the resilient element (3) again can reduce the negative pressure differential by pushing air back into the ear canal. Accordingly, the ear pump (1) can be used to produce pulses of negative pressure in the external ear canal (17), such as by preloading the resilient element (3) before insertion into the ear and by repeatedly pressing and releasing the resilient element (3) after insertion. A sustained negative pressure differential can be produced by preloading the resilient element (3) before insertion into the ear and by then releasing the resilient element (3) for a sustained period of time.

The ear pump (1) can be used to produce changes in the pressure differential between the external ear canal (17) and the ambient pressure that transition between a positive pressure differential and a negative pressure differential. The resilient element (3) of the ear pump (1) can be pressed to a partially compressed state before insertion into the ear. Upon release of the resilient element (3) fluid can be drawn from the external ear canal (17) into the air pump (1) as the resilient element (3) resiliently returns towards the uncompressed state to produce a negative pressure differential between the external ear canal and ambient pressure. Pressing the resilient element (3) past the partially preloaded state (e.g., to the fully compressed state) can drive fluid (e.g., air) out of the ear pump (1) (e.g., through the aperture (9)), which can produce a positive pressure differential between the external ear canal and ambient pressure. Pressing and releasing the resilient element (3) can create pressure pulses that transition between positive pressure differentials and negative pressure differentials. A sustained positive pressure differential can be produced by pressing and holding the resilient element (3) for a sustained period of time. A sustained negative pressure can be produced by releasing the resilient element (3) for a sustained period of time.

Figure 2:
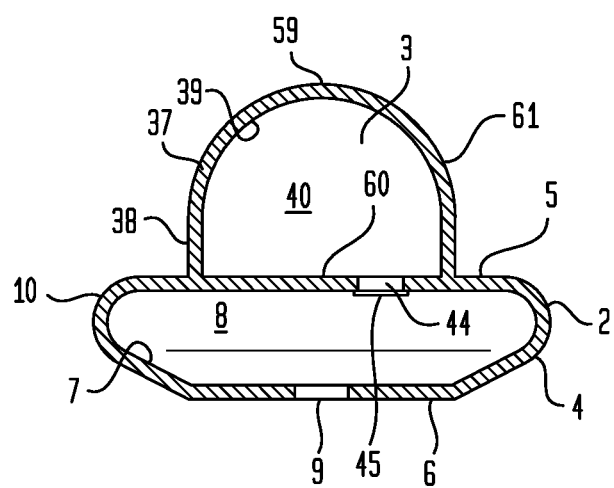
FIG. 2 is cross-sectional view 2-2 of the particular embodiment of the ear pump shown in FIG. 1.
Figure 2A:
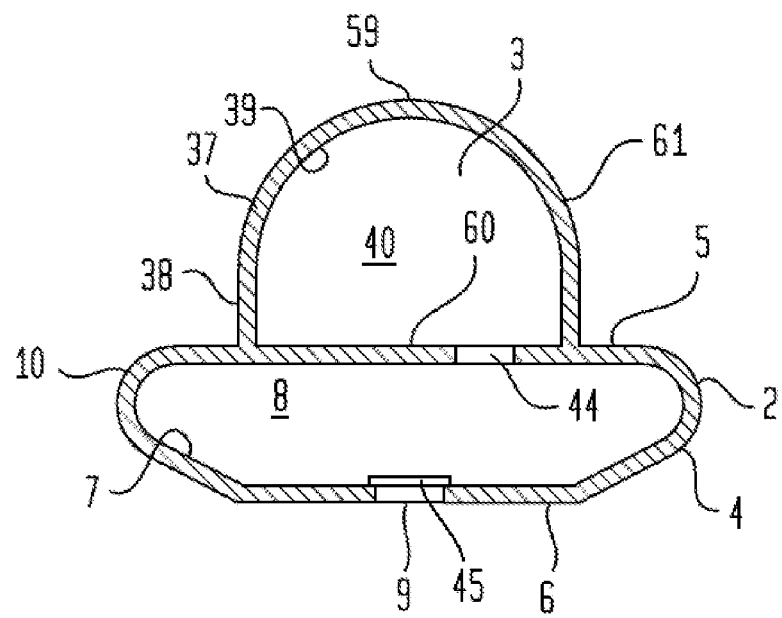
FIG. 2A is an example embodiment of an ear pump.
Figure 2B:
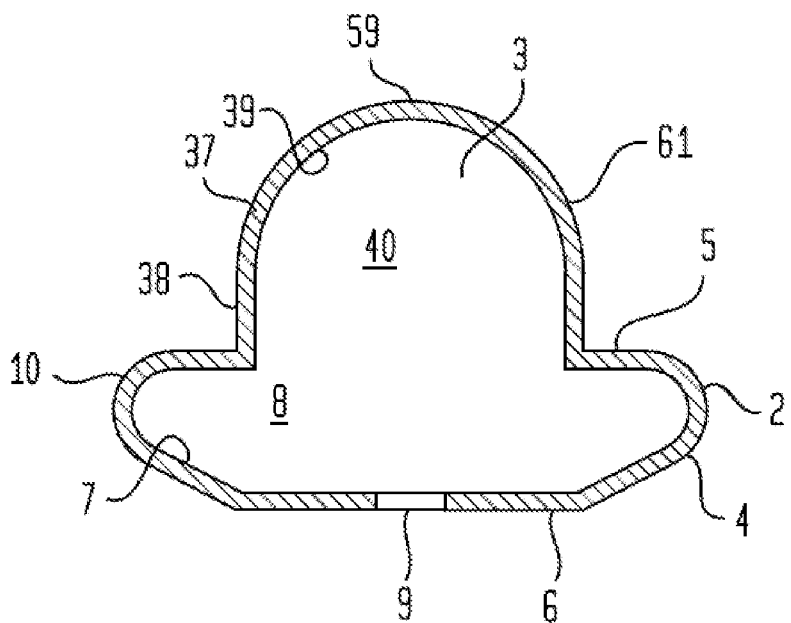
FIG. 2B is another example embodiment of an ear pump.

In some embodiments, the valve (45) can be at the aperture (9) rather than at the aperture (44), as shown in FIG. 2A. In some cases, the wall between the resilient element (3) and the support element (2) can be omitted, as shown in FIG. 2B. The embodiment illustrated by FIG. 2B does not include the valve (45), although in some embodiments, the valve (45) can be included, such as at aperture (9), and any of the other valve configurations disclosed herein can be applied to FIG. 2B.

Figure 2C:
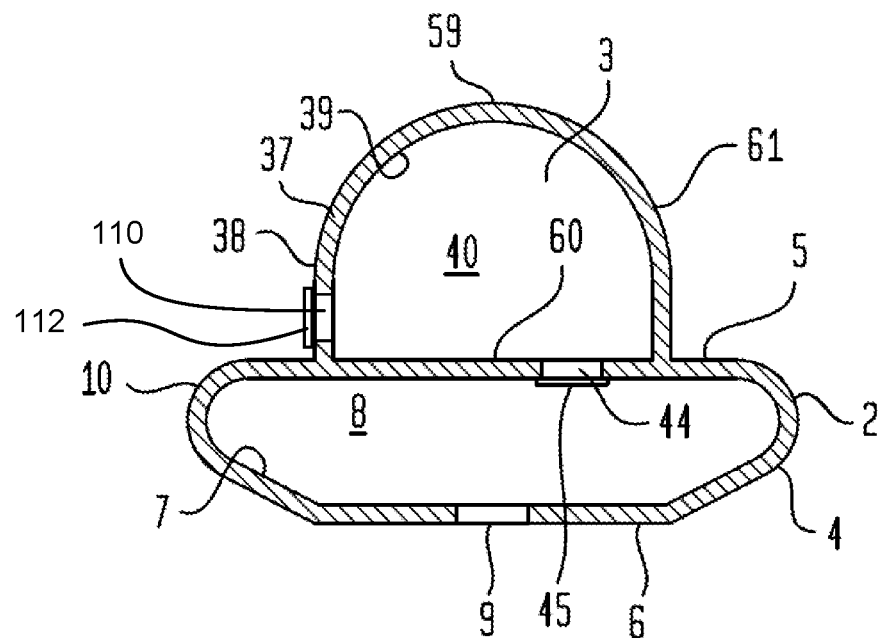
FIG. 2C is another example embodiment of an ear pump.
Figure 2D:
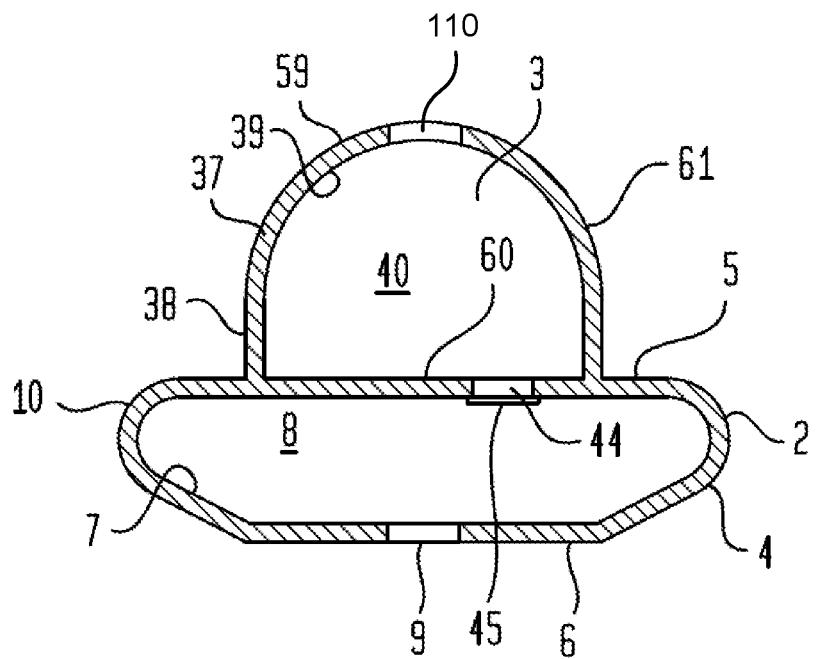
FIG. 2D is another example embodiment of an ear pump.

With reference to FIG. 2C, the ear pump (1) can include a resilient element aperture (110), which can permit fluid flow between the resilient element interior space (40) and the ambient environment outside the ear. The resilient element aperture (110) can be formed in a side wall of the resilient element (3), as shown in FIG. 2C, on a top side of the resilient element (3), as shown in FIG. 2D, or any other suitable location so that fluid can flow through the resilient element aperture (110) between the ambient area outside the ear pump (1) and the resilient element interior space (40). In some embodiments, a valve (112) can control fluid flow through the resilient element aperture (110). The valve (112) can be a one-way valve or check valve. The valve (112) can be configured to permit fluid (e.g., air) to flow from the ambient area, through the resilient element aperture (110), and into the resilient element interior space (40), and can impede fluid from flowing out of the resilient element interior space (4) to the ambient are outside the ear pump (1). The valve (112) can be configured to permit fluid to ingress into the resilient element interior space (40), while impeding fluid from egres sing out of the resilient element interior space (40) through the aperture (110).

The resilient element aperture (110) can be used to return the resilient element (3) from the compressed state to the uncompressed state while the ear pump (1) is sealably engaged with the ear. Pressing the resilient element (3) to the compressed state can cause fluid (e.g., air) to flow out of the ear pump (1) (e.g., through the aperture 9) and into the external ear canal (17). The valve (112) can impede fluid from flowing out through the resilient element aperture (110) when the resilient element (3) is pressed. When the resilient element (3) is released, the valve (45) can impede fluid from flowing from the external ear canal (17) back into the ear pump (1). The valve (45) can be positioned at aperture (44) or aperture (9). When the resilient element (3) is released, fluid (e.g., air) can flow through the resilient element aperture (110) to refill the resilient element interior space (40) as the resilient element (3) returns to the uncompressed state. The resilient element (3) can be pressed multiple times to incrementally increase the positive pressure differential between the external ear canal pressure and the ambient pressure.

In some embodiments, the flow direction of the valves (45) and (112) can be reversed, to provide an ear pump (1) configured to produce a negative pressure differential between the external ear canal pressure and the ambient pressure. The valve (45) can be configured to permit fluid flow from the support element interior chamber (8) into the resilient element interior space (40) (e.g., through the aperture 44), while impeding fluid flow from the resilient element interior space (40) to the support element interior chamber (8). Accordingly, the valve (45) can impede fluid (e.g., air) from flowing out of the ear pump (1), such as through the opening (9). The valve (45) can prevent fluid from flowing from the ear pump (1) to the external ear canal, when the ear pump (1) is engaged with the ear. The valve (45) can be positioned at the aperture (9), in some embodiments. The valve (112) can be configured to permit fluid flow from the resilient element interior space (40) to the ambient environment outside the ear pump (1), such as through the resilient element aperture (110). The valve (112) can impede fluid flow from the ambient environment to the resilient element interior space (40), such as through the resilient element aperture (110). When the resilient element (3) is pressed to the compressed state, fluid (e.g., air) can be driven out of the resilient element interior space (40), and can exit the ear pump (1) through the resilient element aperture (110), such as through the valve (112). When the resilient element (3) is released, the resilient element (3) can move towards the uncompressed state, which can draw fluid (e.g., air) into the resilient element interior space (40). The valve (112) can impede fluid from flowing in from the ambient area to refill the resilient element interior space (40). The valve (45) can permit fluid from the external ear canal (17) to flow into the ear pump (1), such as through the aperture (9). The resilient element (3) can be pressed multiple times to incrementally increase a negative pressure differential between the external ear canal pressure and the ambient pressure.

With reference to FIG. 2D, in some embodiments, the resilient element aperture (110) does not include a valve (112). The resilient element aperture (110) can be covered, such as with a finger of a user or an actuator, to close the resilient element aperture (110) to impede fluid from flowing through the resilient element aperture (110). The resilient element aperture (110) can be uncovered, such as by removal of the user's finger or actuator, to permit fluid to flow through the resilient element aperture (110). The valve (45) can be configured to permit fluid to flow out of the ear pump (1) into the external ear canal (17), while impeding fluid from flowing from the external ear canal (17) into the ear pump (1). The resilient element aperture (110) can be covered and the resilient element (3) can be pressed to the compressed state to drive fluid out of the ear pump (1) and into the external ear canal (17), to produce a positive pressure differential, as discussed herein. The resilient element aperture (110) can then be uncovered to permit fluid to flow through the resilient element aperture (110) and into the resilient element interior space (40), as the resilient element (3) returns towards the uncompressed state. The resilient element (3) can be pressed and released multiple time, while covering the resilient element aperture (110) during compression and uncovering the resilient element aperture (110) during decompression, to incrementally increase the positive pressure differential between the external ear canal pressure and ambient pressure. Alternatively, the valve (45) can be configured to impede fluid from flowing out of the ear pump (1) into the external ear canal (17), while permitting fluid to flow from the external ear canal (17) into the ear pump (1). The resilient element aperture (110) can be pressed to the compressed state while the resilient element aperture (110) is uncovered, such as by pressing on the resilient element (3) at a location other than where the resilient element aperture (110) is located. Pressing the resilient element (3) to the compressed state can drive fluid out of the resilient element interior space (40) through the resilient element aperture (110) to the ambient area outside the ear pump (1). The resilient element aperture (110) can then be covered and permitted to return towards the uncompressed state (e.g., by pulling back the finger or actuator). This can cause fluid to flow from the external ear canal (17) and into the ear pump (1), which can produce a negative pressure differential between the external ear canal pressure and the ambient pressure. The resilient element (3) can be pressed and released multiple time, while uncovering the resilient element aperture (110) during compression and covering the resilient element aperture (110) during decompression, to incrementally increase the negative pressure differential between the external ear canal pressure and ambient pressure.

Figure 6:
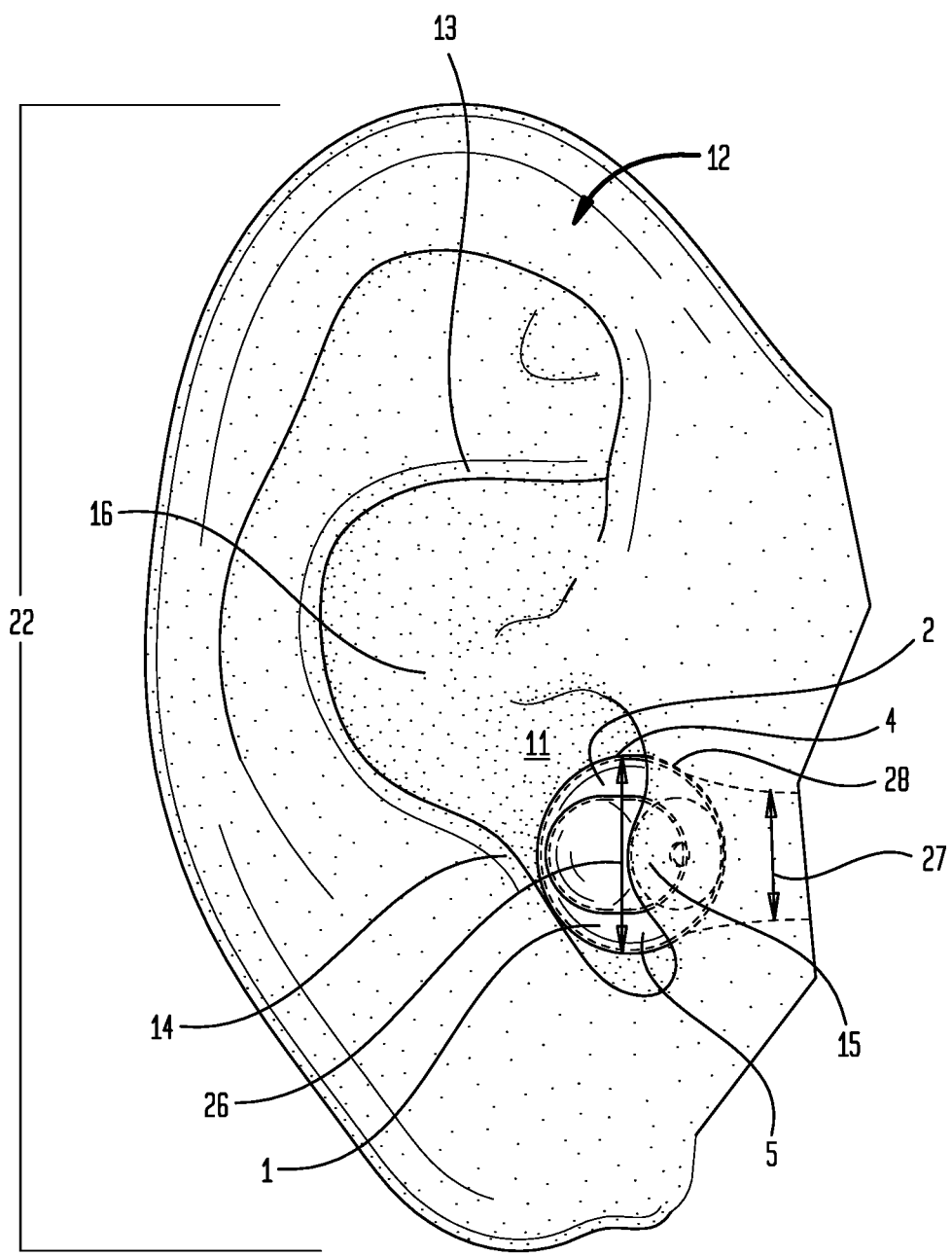
FIG. 6 is an illustration of the particular embodiment of the ear pump releasably retained in the auricle of the ear.
Figure 6A:
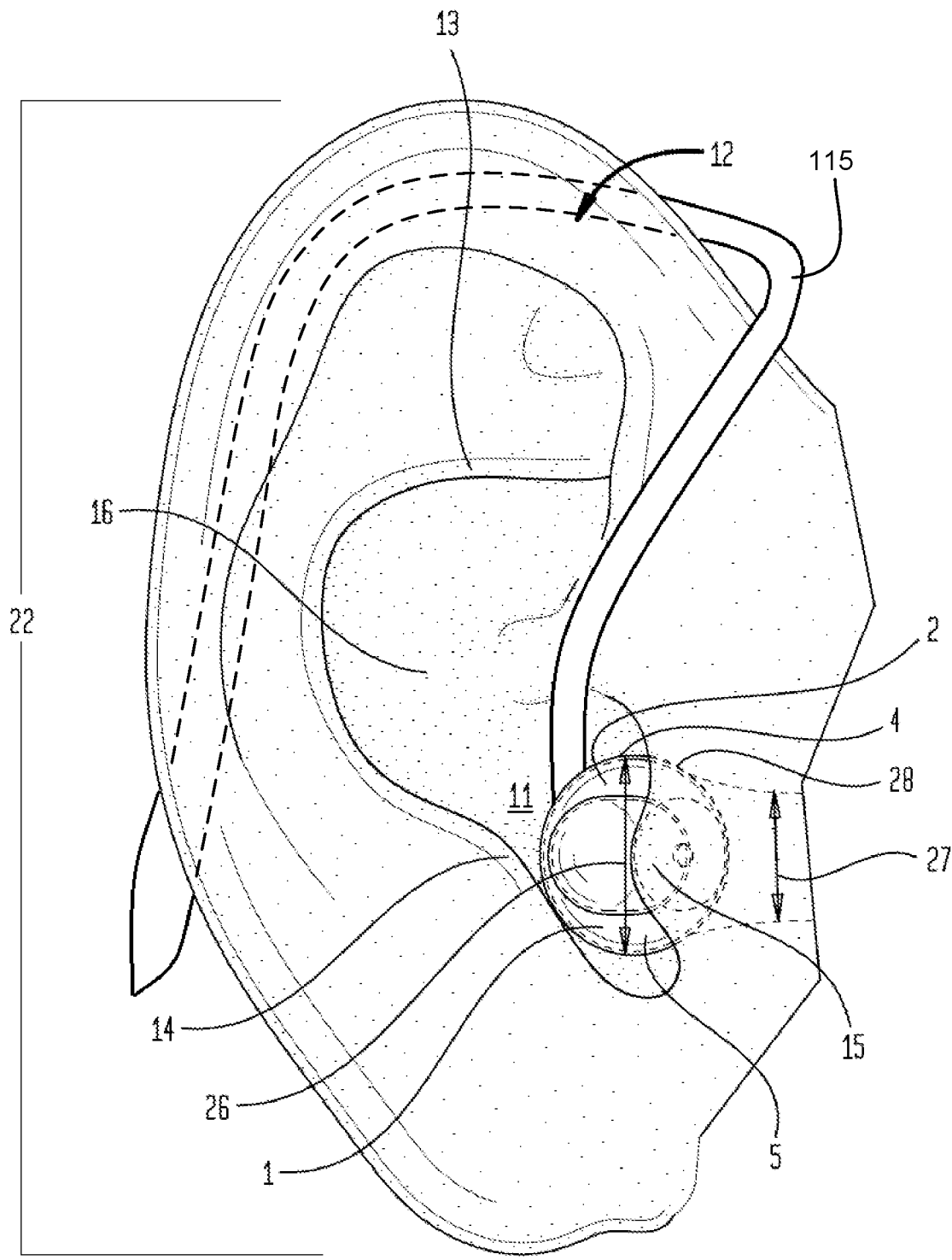
FIG. 6A is an illustration of an example embodiment of an ear pump attached to an ear by an attachment element.

With reference to FIG. 6A, the ear pump (1) can include an attachment feature, which can be configured to temporarily attach the ear pump (1) to the subject. The attachment feature can be configured to releasably engage an anatomical structure on the subject. For example, the attachment feature, as shown in this present illustrated embodiment, can include an arm (115) that is configured to extend from the ear pump (1) (e.g., from a side of the support element (2)), up along a front side of the auricle to an upper portion of the ear, and to extend downward along a back side of the auricle (e.g., the between the auricle and the head). The arm (115) can wrap around the auricle of the ear. The arm (115) can engage the auricle of the ear to help position the ear pump (1) and to support and hold the ear pump (1) substantially in place sufficient to maintain a seal, especially when a pressure differential is applied.

Figure 6B:
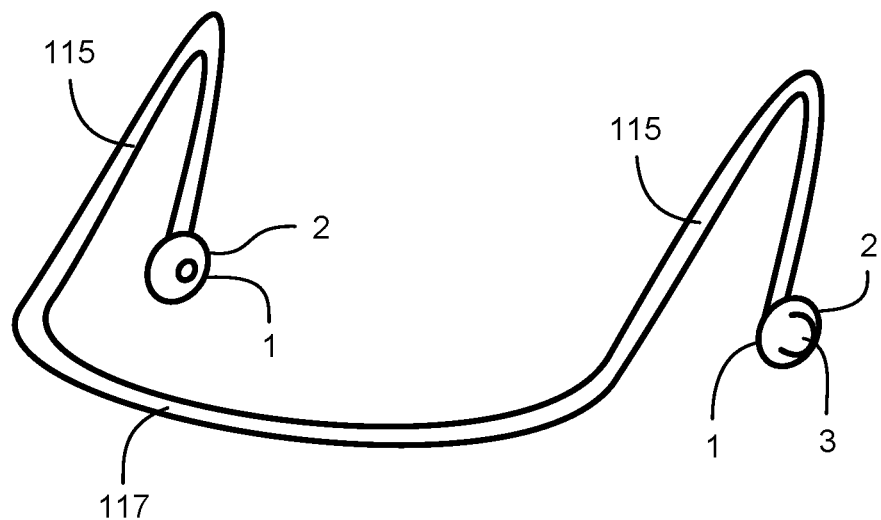
FIG. 6B shows an example embodiment of a pair of ear pumps on an attachment element.

It is appreciated, however, that various other types of attachment features can be used, either individually or in various combinations. For example, FIG. 6B shows can example embodiment having two ear pumps (1), one for each ear. An arm (115), which for example (but without limitation) can be similar to the arm (115) discussed in connection with FIG. 6A, can extend from each of the two ear pumps (1). The arms (115) can be joined by a joining element (117), which can be configured to be worn in a manner that extends behind the subject's head. Many other alternatives may also be employed, without departing from the broad scope of this disclosure. According to certain such further examples, the joining element can be configured to be worn in a manner that extends over the top of the subject's head, or behind the patient's neck, or in front of the patient's neck (e.g., under the jaw). It is also appreciated that such joining elements may be configured to further engage such facial-cranial or neck structures when worn, such as to provide additional support to the ear pieces themselves, but in other embodiments such additional engagement or support may not be necessary. In one aspect of certain such other embodiments, the joining element provides a beneficial purpose in tying the two separate earpieces into a connected overall structure. In still further modes, the joining element may provide sufficient support between these two earpieces to hold them inward toward the ear canals. Such joining elements may be constructed of appropriate materials and design to provide sufficient flexibility to facilitate releasably engaging the ear pieces in place in the respective outer ear canals, but while then having sufficient rigidity to provide support against disengagement of those ear pieces (e.g. similar to a stethoscope). In other modes, the joining element may be adjustable between a first condition, allowing for positioning of the ear pieces for desired therapy, and a second condition, which provides more support against dislodgement. In still further modes, the joining element may be a single structure, or may comprise an assembly of multiple attached or cooperating structures, and may again be rigid, appropriately flexible, or adjustable, to achieve the overall objectives and purpose for a more specific use consistent with this disclosure. In yet further more detailed embodiments, the joining element may be formed integrally with a housing for the ear piece (and/or controller or actuator mechanism for the ear piece pressure differential therapy), or may be separate components that are attached together. It is also appreciated that these various further modes and embodiments of the present illustrated embodiment of FIG. 6B are similarly applicable to other embodiments shown or otherwise disclosed herein.

In still further embodiments, it is also appreciated that the ear piece housing, or one or more structures of such joining element(s), may also be suitably configured to house, at least in part, an actuator for pressure modulation that is fluidly coupled to the ear piece to deliver such pressure changes, and/or to house such a fluid conduit otherwise coupled to such an actuator provided separately. the ear piece housing, or one or more structures of such joining element(s), can also house the controller (127), memory (129), and/or power source (131), which can be used to operate an actuator (125).

Figure 6C:
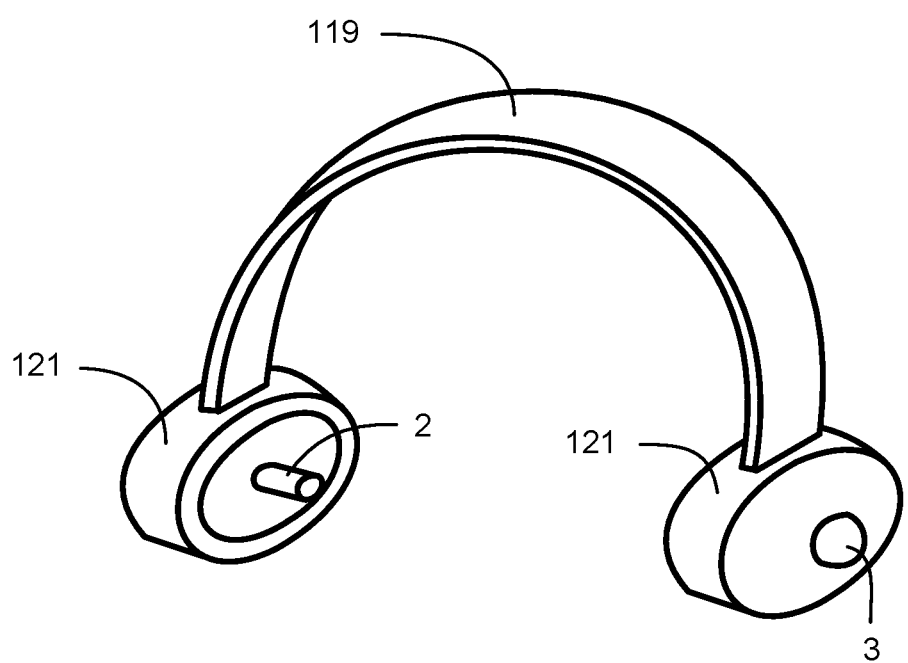
FIG. 6C shows another example embodiment of a pair of ear pumps on an attachment element.
Figure 7:
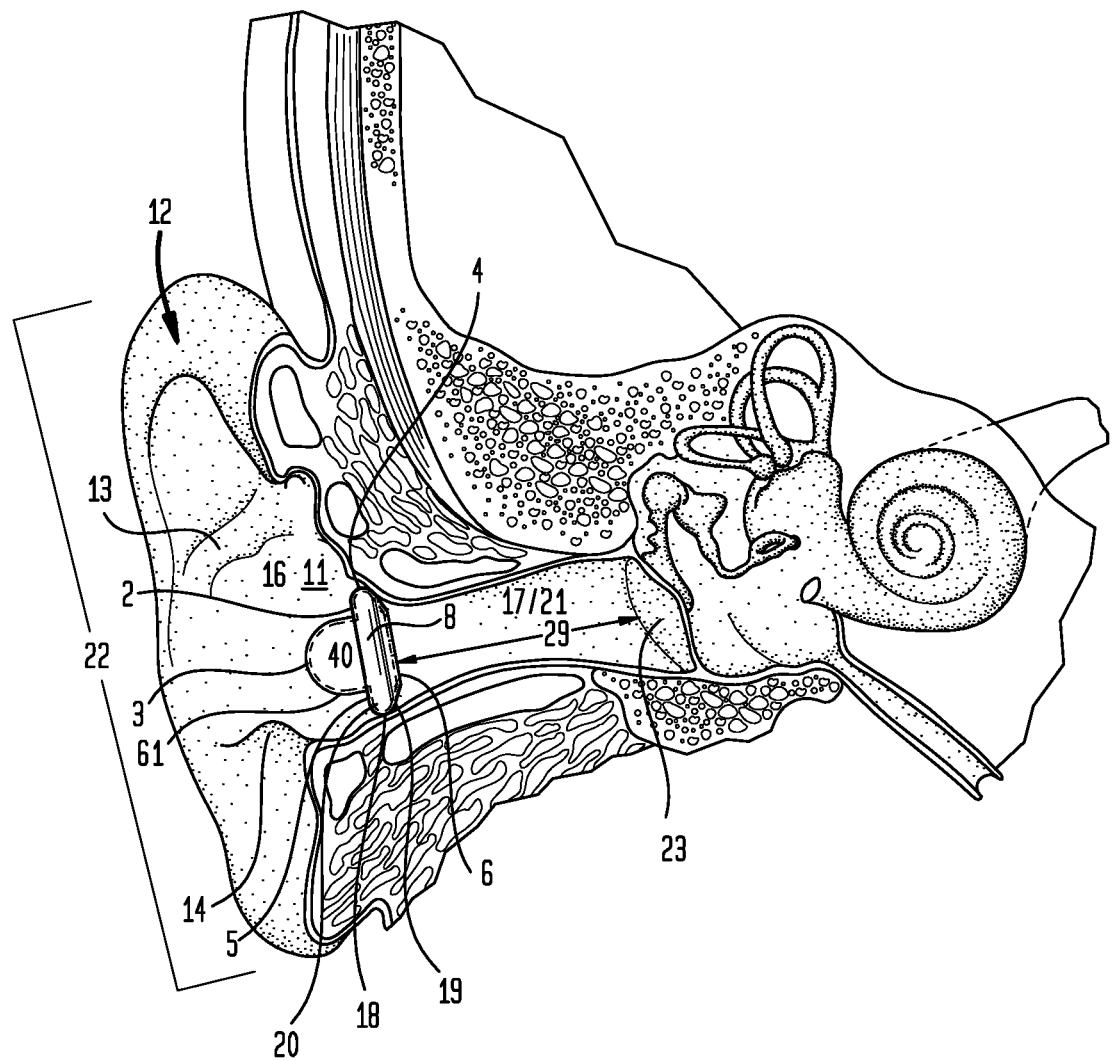
FIG. 7 is a cross-sectional view through the anatomy of the ear showing the particular embodiment of the ear pump shown in FIG. 1 releasably retained in the auricle of the ear.

FIG. 6C shows an example embodiment of an attachment feature that includes a headband (119) and ear cups (121), with the ear pumps (1) incorporated into the ear cups (121). In FIG. 6C, the ear pump (1) is shown having a support element (2) that extends into the external ear canal (17) (e.g., which can be similar to the embodiments of FIGS. 10 to 25), although any ear pump (1) disclosed herein can be used with the attachment feature of FIG. 6C.

In some embodiments, the ear pump (1) can be a manual ear pump. The resilient element (3) can be pressed, for example, manually by a finger of the subject or by the finger of a medical practitioner, or by another form of pressing implement that is operated manually. In some embodiments, the ear pump (1) can be operated automatically or can be automated or partially automated. For example, with reference to FIG. 9A, the ear pump (1) can be used with an actuator (125) for actuating the ear pump (1), such as for example (but without limitation) for pressing the resilient element (3). The ear pump (1) can be actuated by something other than a human finger or hand. According to on example, the actuator (125) can include an arm that can be driven forward to compress the resilient element (3) and can be retracted to decompress the resilient element (3). The actuator (125) can include a solenoid motor, a voice coil motor, or any suitable mechanism for driving the actuator (125). The actuator (125) can be driven hydraulically, pneumatically, electromechanically (e.g., an electrically deformable material), or by any other suitable technique. The actuator (125) can include a piston, lever, plunger, cam, or any other suitable structure. In some embodiments, the actuator (125) can include a bar or other structure that can be actuated to move laterally along the resilient element (3) to compress the resilient element (3). The bar can be rotated, such as to have a "rolling pin" effect. As the bar is rotated in a first direction, it can move to laterally compress more of the resilient element (3), and when the bar is rotted in a second direction, it can move laterally to compress less of the resilient element 93). The system can include one or more cogs, pinions, gears, etc. to rotate and/or move the bar.

In some embodiments, the resilient element (3) can be coupled to the actuator (125) so that the actuator (125) can pull the resilient element (3) back to the uncompressed position. In some cases, the resilient element (3) is not attached to the actuator (125), so that the resilient element (3) can return towards the uncompressed state because of the resilience of the resilient element material. In some cases, if the actuator (125) is retracted far enough, the actuator (125) can be brought out of contact with the resilient element (3).

In some embodiments, an attachment element can support both the actuator (125) and the ear pump (1). For example, an ear cup (121) similar to FIG. 6C can include the ear pump (1) at a location configured to insert the ear pump (1) into the ear when the ear cup (121) is worn. The ear cup (121) can also include the actuator (125) positioned to actuate the ear pump (1). In some embodiments, the ear pump (1) can be a separate from the actuator (125). For example, the ear pump (1) can be inserted into the ear. Then a separate component that includes the actuator (125) can be coupled to the subject (e.g., by placing a headband (119) or other attachment element) onto the subject. Or the subject can sit or lie while a component that includes the actuator is brought into proximity of the subject so that it can operate the ear pump (1), such as without contacting the subject.

A controller (127) can be coupled to the actuator (125). The controller (127) can be implemented using one or more hardware processors. In some cases a processor can execute instructions that are stored on non-transitory machine-readable memory (129). The instructions can cause the controller (127) to operate the actuator (125) to implement the various different processes and procedures discussed herein. In some cases, a plurality of pressure treatment profiles can be stored in the machine-readable memory (129). The controller (129) can implement various pressure profiles, as discussed at least in U.S. Pat. No. 9,039,639 and PCT Patent Application No. PCT/US2017/064964, which are incorporated herein by reference. In some cases, a user device, such as a mobile device, smart phone, tablet, wearable device, smart watch, or similar device can be used to control the ear pump (1). Various additional details regarding control of the ear pump (1) are disclosed in U.S. Pat. No. 9,039,639 and PCT Patent Application No. PCT/US2017/064964, which are incorporated herein by reference. In some embodiments, the ear pump (1) can include a material that deforms in response to electrical current applied thereto. The controller (127) can provide electrical current to the deformable material to cause it to contract and/or expand in order to produce flow of fluid (e.g., air), as discussed herein. The system can include a power source (131), such as a battery. The power source (131) can provide power to the processor (127) and/or to the computer-readable memory (129). The power source (131) can supply power for operating the actuator (125) and other features discussed herein. In some embodiments, the piston (31) can comprise a magnetic material. The actuator (125) can drive the piston (31) using magnetism. In some cases the actuator (125) can include an electromagnet.

Figure 19A:
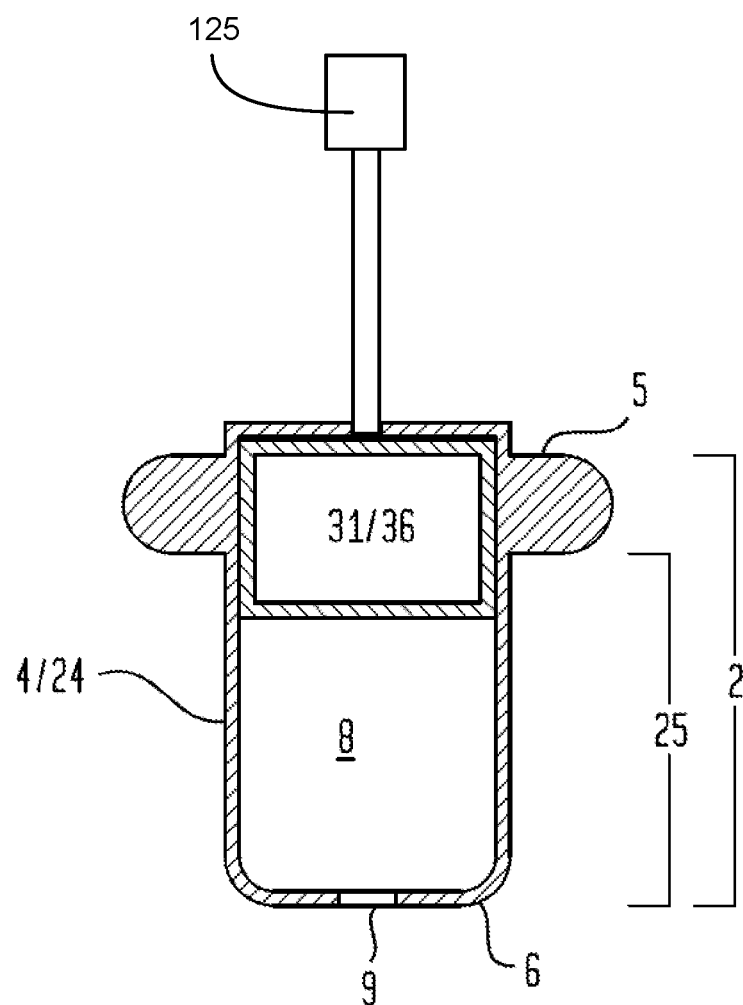
FIG. 19A shows another example embodiment of an ear pump with an actuator.
Figure 19B:
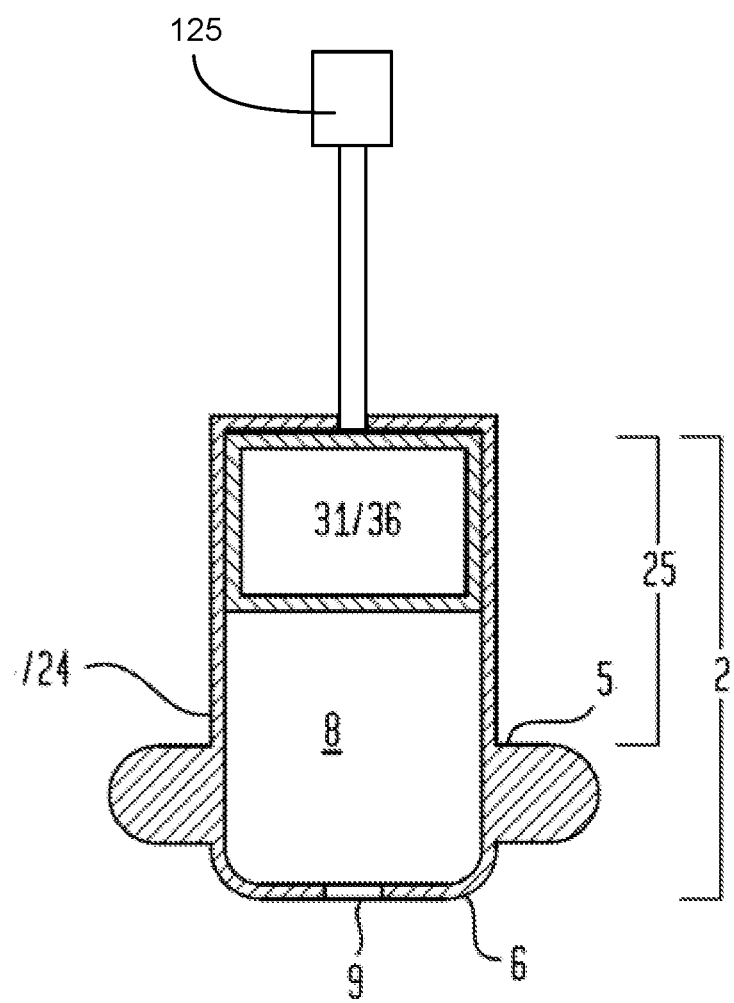
FIG. 19B shows another example embodiment of an ear pump with an actuator.

FIG. 19A shows an example embodiment of an ear pump (1), which can be similar to the ear pump (1) embodiments of FIGS. 18 to 25. In some embodiments, the resilient element (3) can be omitted. An actuator (125) can be coupled to the piston (31). The actuator (125) can drive the piston (31) forward to push fluid (e.g., air) out of the ear pump (1), such as through the aperture (9). The actuator (125) can draw the piston (31) back to pull fluid (e.g., air) into the air pump (1), such as through the aperture (9). In FIG. 19A, the piston (31) can be driven forward into the external ear canal (17). In FIG. 19B, the ear pump (1) can be configured so that the piston (31) remains outside the external ear canal (17) when it is driven forward. The support element (2) can include an enlarged portion, which can be wider than the external ear canal, and in some cases can engage a concha bowl of the ear. The elongate tubular wall (24) can be positioned distally of the enlarged portion, so that the elongate tubular wall (24) does not insert into the external ear canal (17) when the ear pump (1) is engaged with the ear.

Figure 19C:
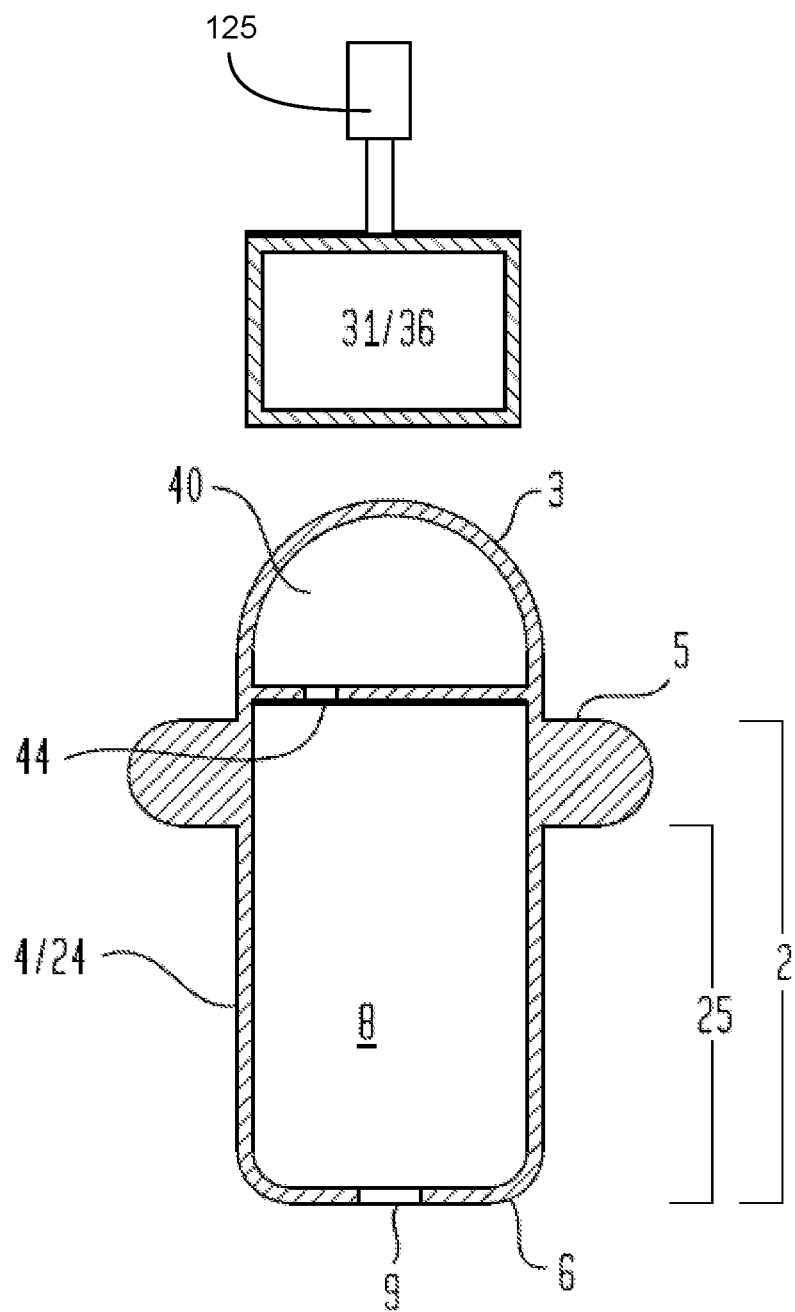
FIG. 19C shows another example embodiment of an ear pump with an actuator.
Figure 20:
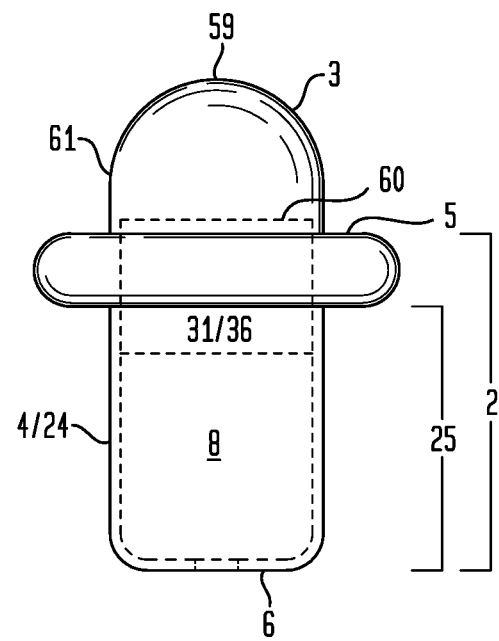
FIG. 20 is a side elevation view of the particular embodiment of the ear pump.
Figure 21:
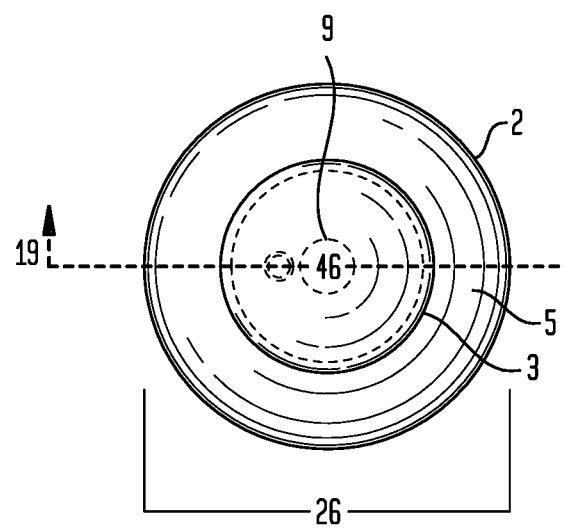
FIG. 21 is a top plan view of the particular embodiment of the ear pump.
Figure 22:
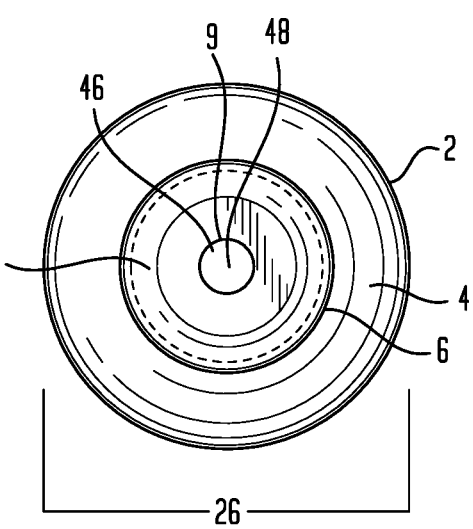
FIG. 22 is a bottom plan view of the particular embodiment of the ear pump.
Figure 23:
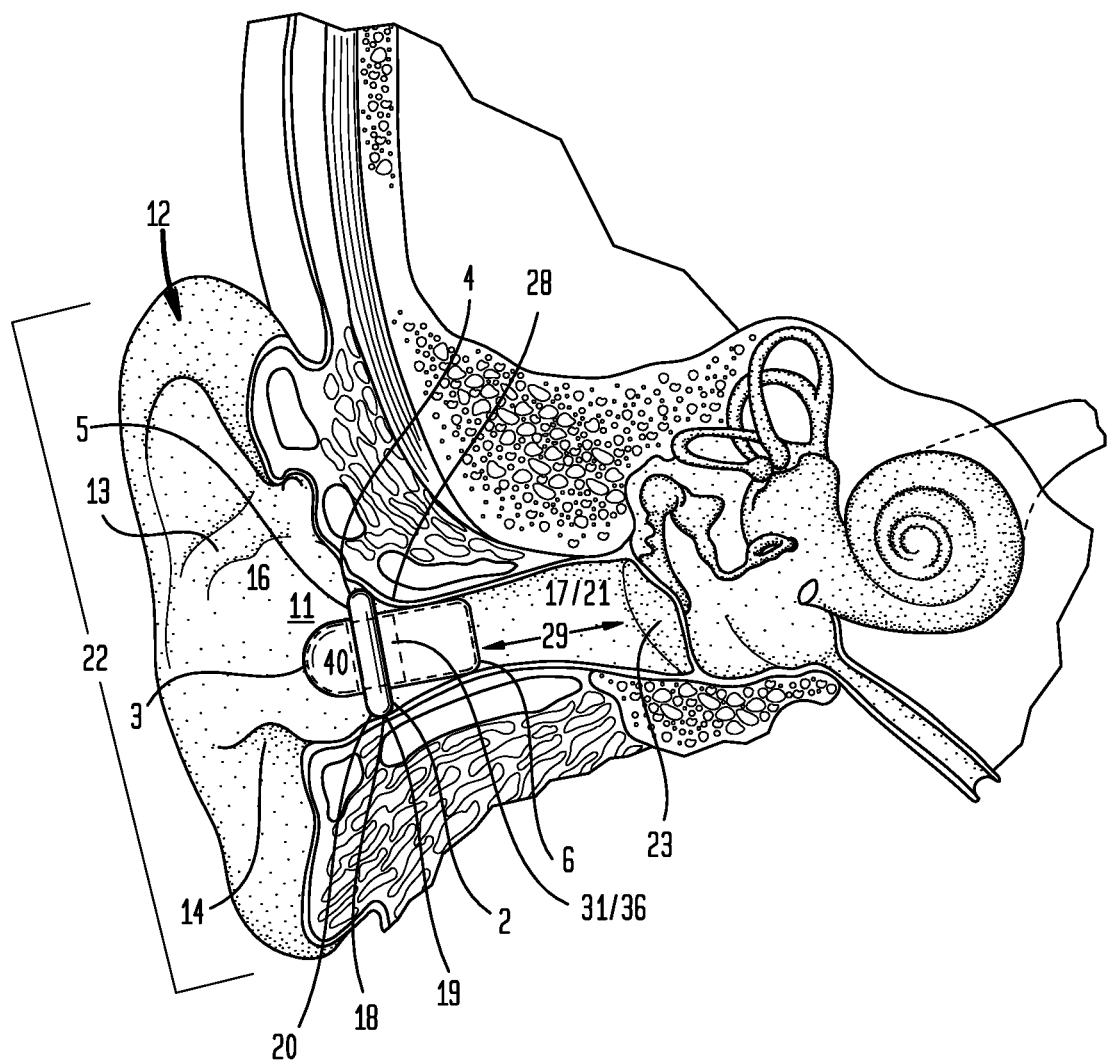
FIG. 23 is a cross-sectional view of the anatomy of the ear showing the particular embodiment of the manual ear pump releasably retained in the auricle of the ear.
Figure 24:
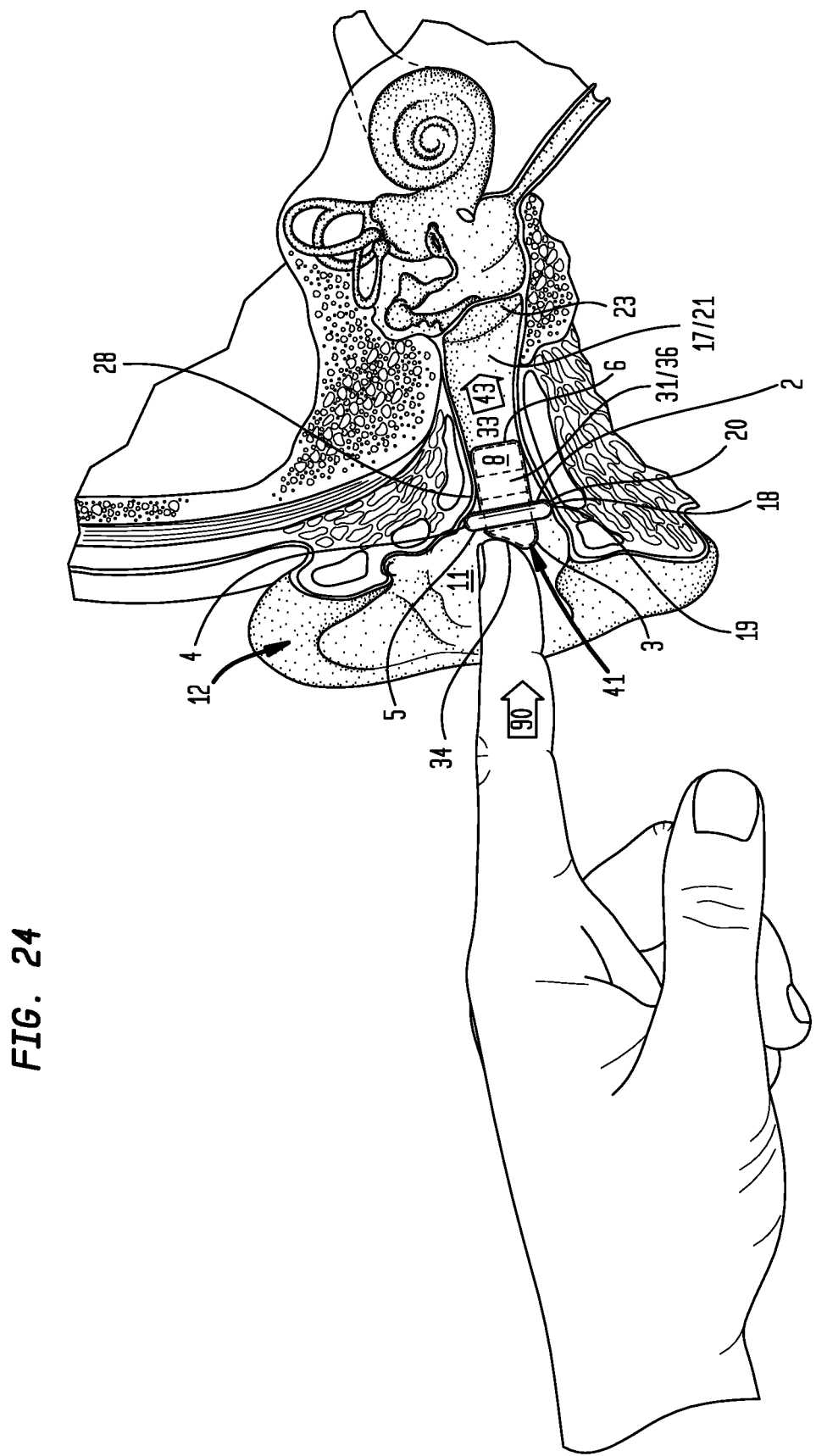
FIG. 24 is a cross-sectional view of the anatomy of the ear showing a method of using the particular embodiment of the ear pump releasably retained in the auricle of the ear.
Figure 25:
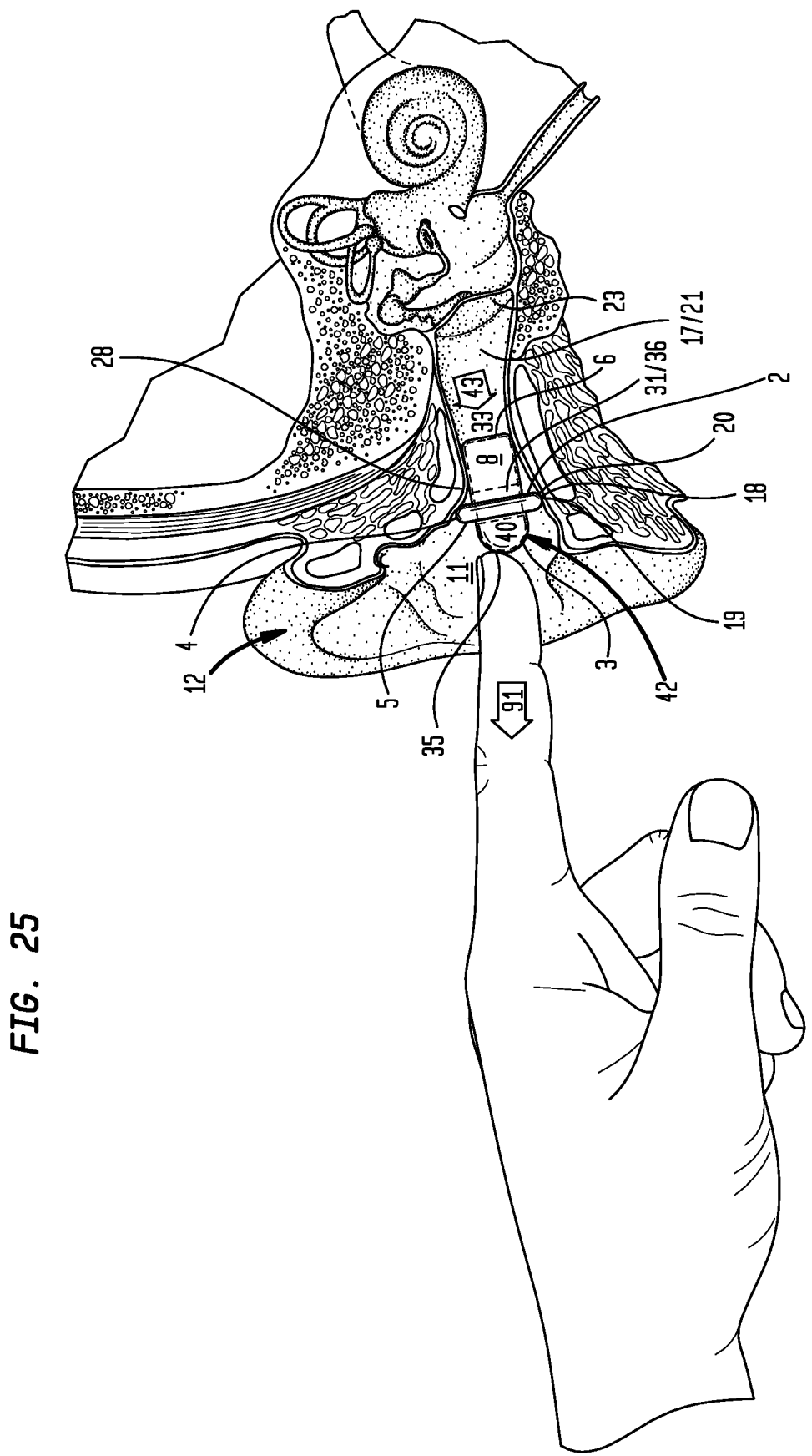
FIG. 25 is a cross-sectional view the anatomy of the ear showing a method of using the particular embodiment of the ear pump releasably retained in the auricle of the ear.
Figure 26:
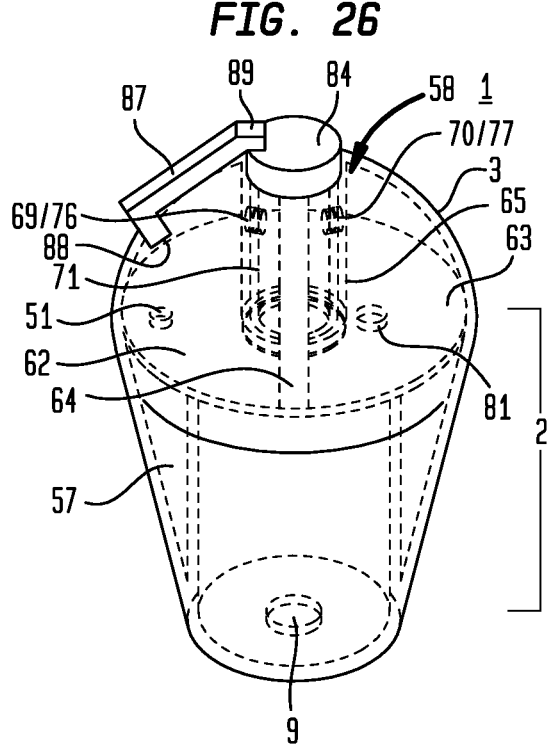
FIG. 26 is a perspective view of another particular embodiment of an ear pump, which can be a manual ear pump.
Figure 27:
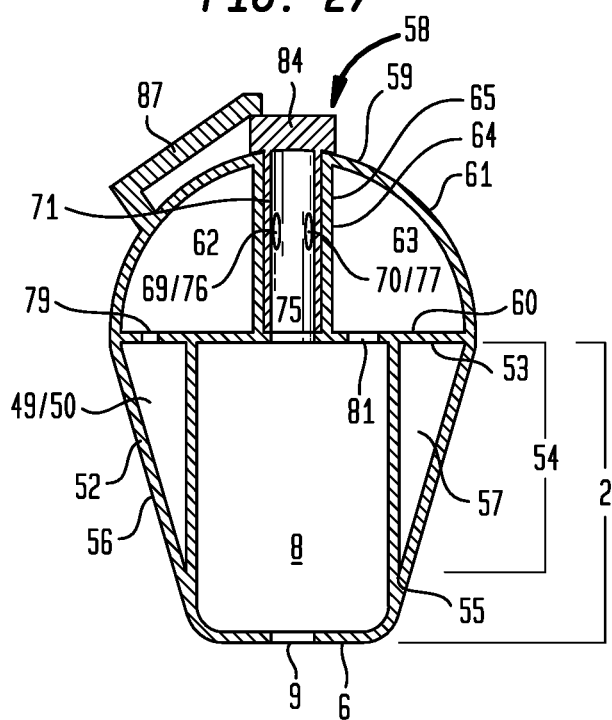
FIG. 27 is a cross-sectional view 27-27 of the particular embodiment of the ear pump shown in FIG. 26.
Figure 31:
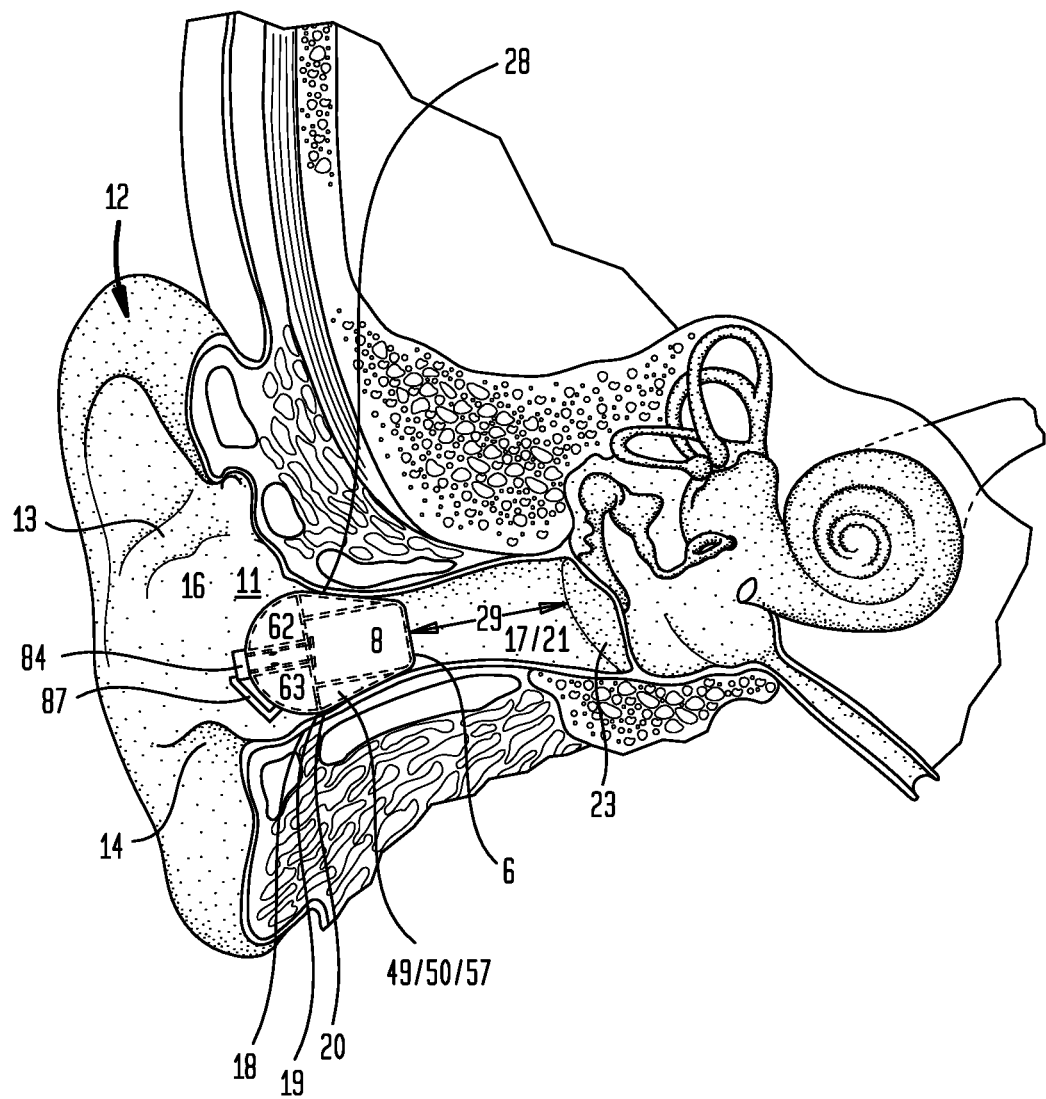
FIG. 31 is a cross-sectional view of the anatomy of the ear showing a method of using the particular embodiment of the ear pump releasably retained in the auricle of the ear.
Figure 32:
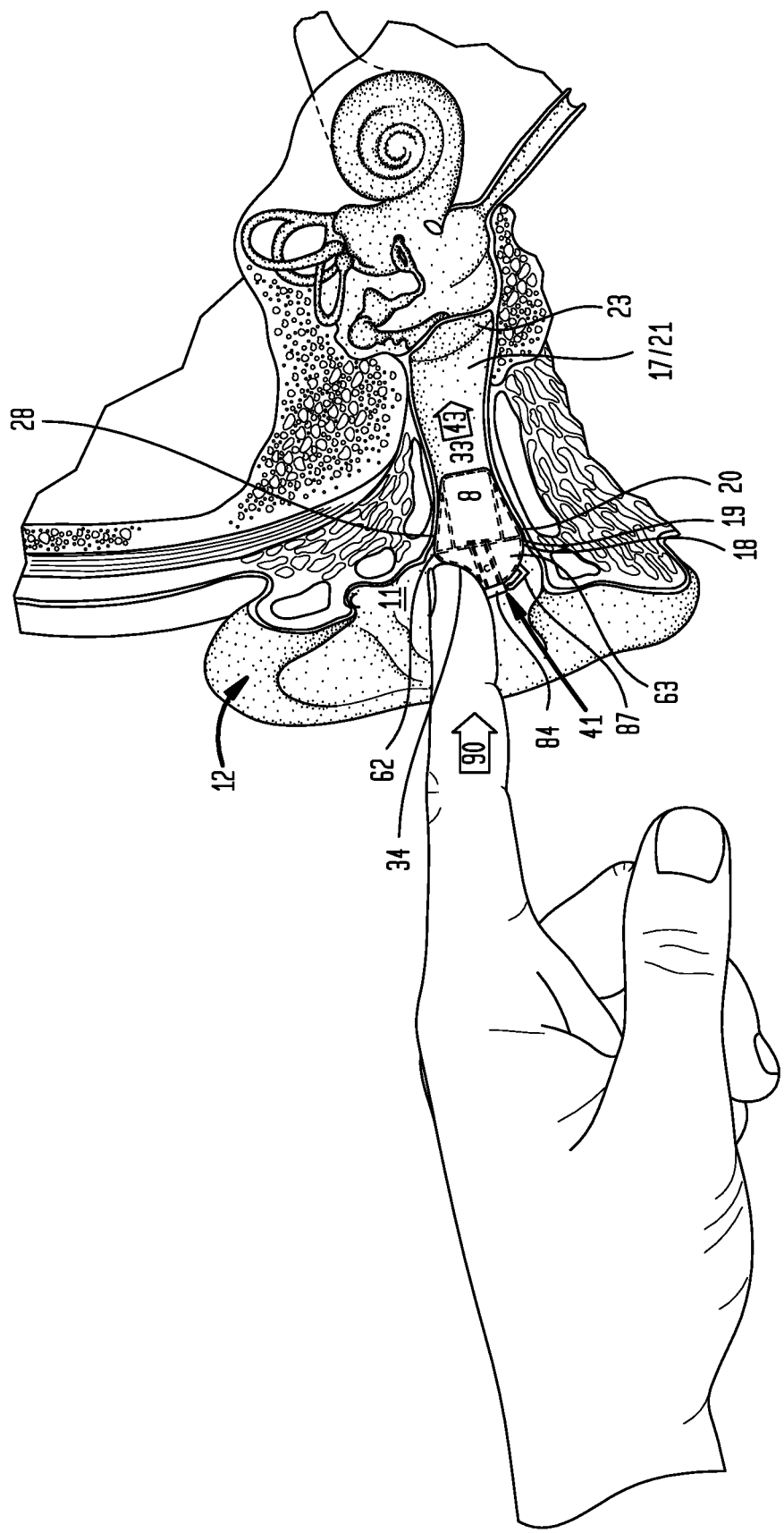
FIG. 32 is a cross-sectional view of the anatomy of the ear showing the particular embodiment of the ear pump releasably retained in the auricle of the ear.
Figure 33:
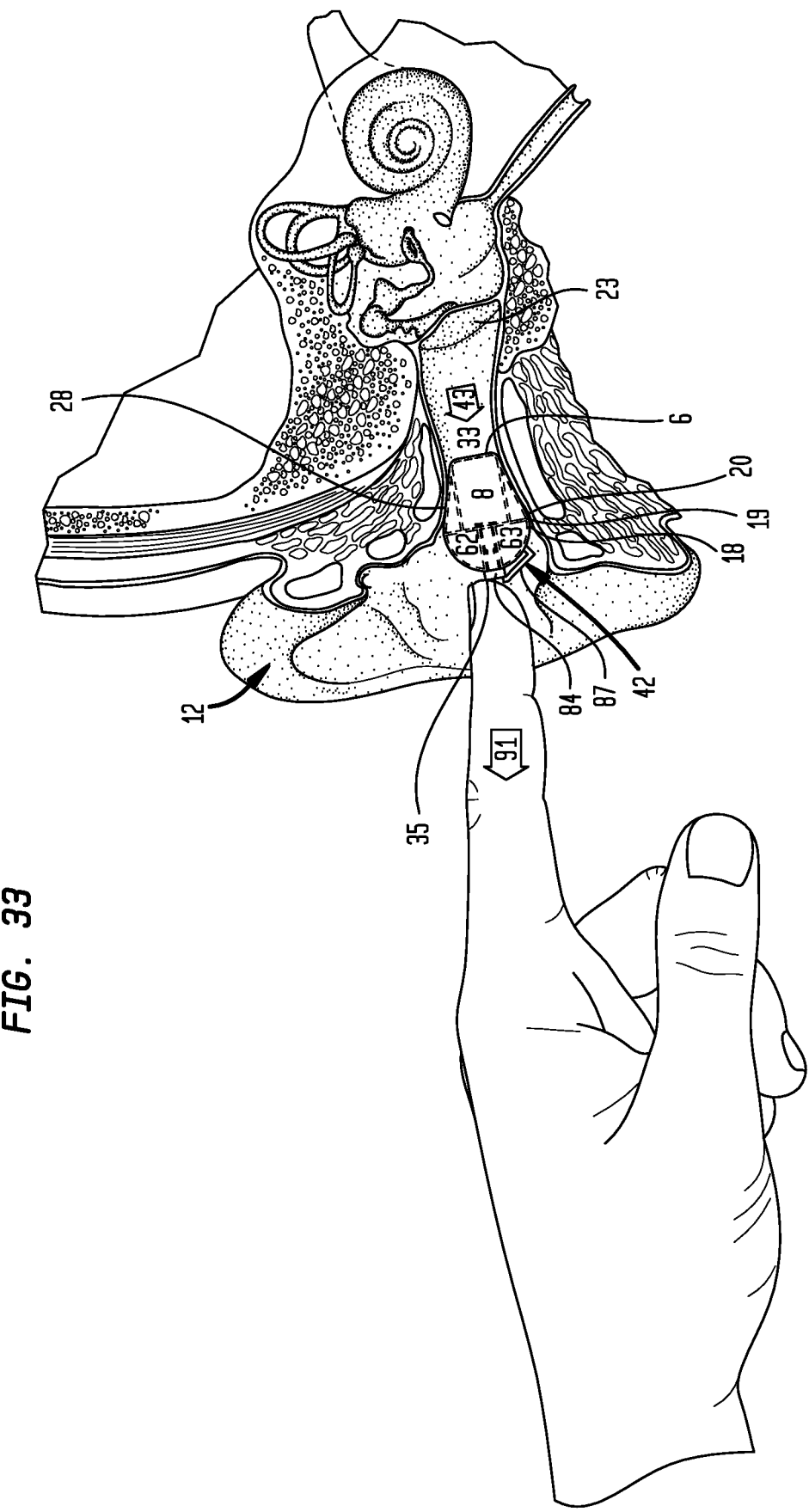
FIG. 33 is a cross-sectional view of the anatomy of the ear showing a method of using the particular embodiment of the ear pump releasably retained in the auricle of the ear.
Figure 34:
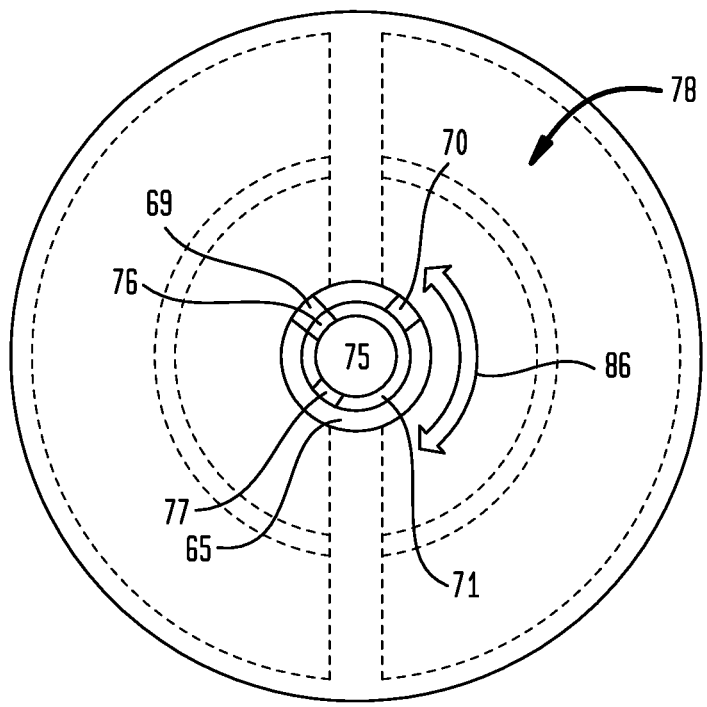
FIG. 34 is a top plan view of the particular embodiment of the ear pump showing a method of disposing a valve assembly in a first position.
Figure 35:
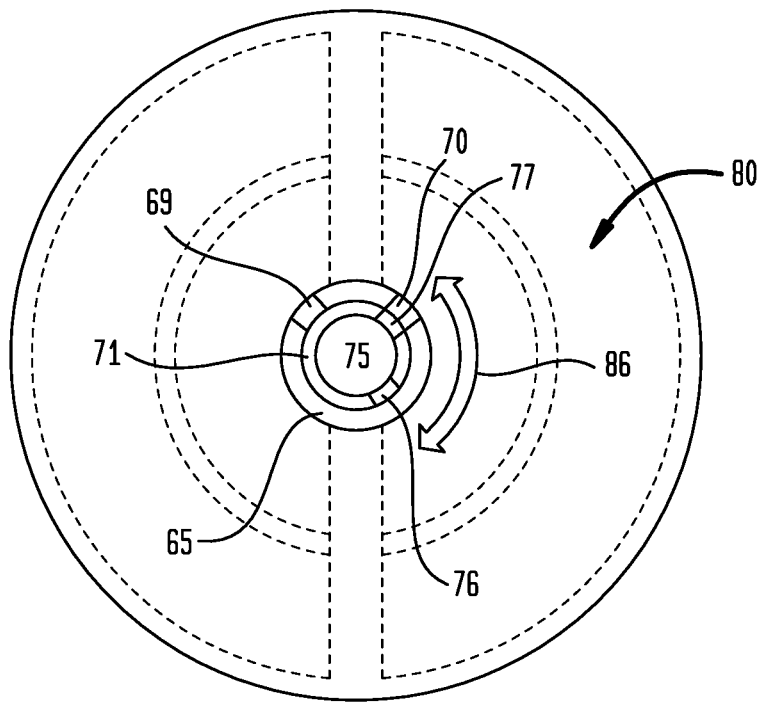
FIG. 35 is a top plan view of the particular embodiment of the ear pump showing a method of disposing a valve assembly in a second position.
Figure 36:
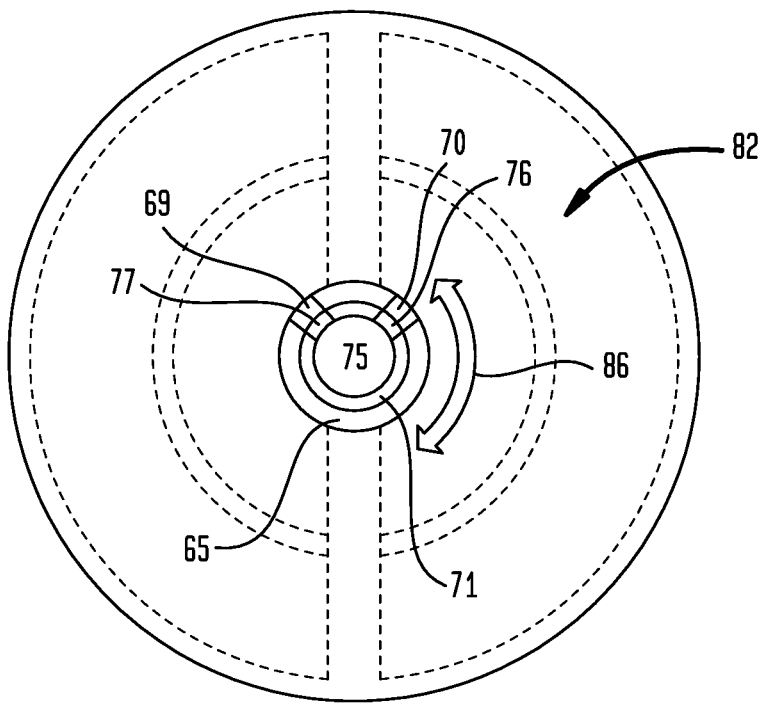
FIG. 36 is a top plan view of the particular embodiment of the manual ear pump showing a method of disposing a valve assembly in a third position.
Figure 37:
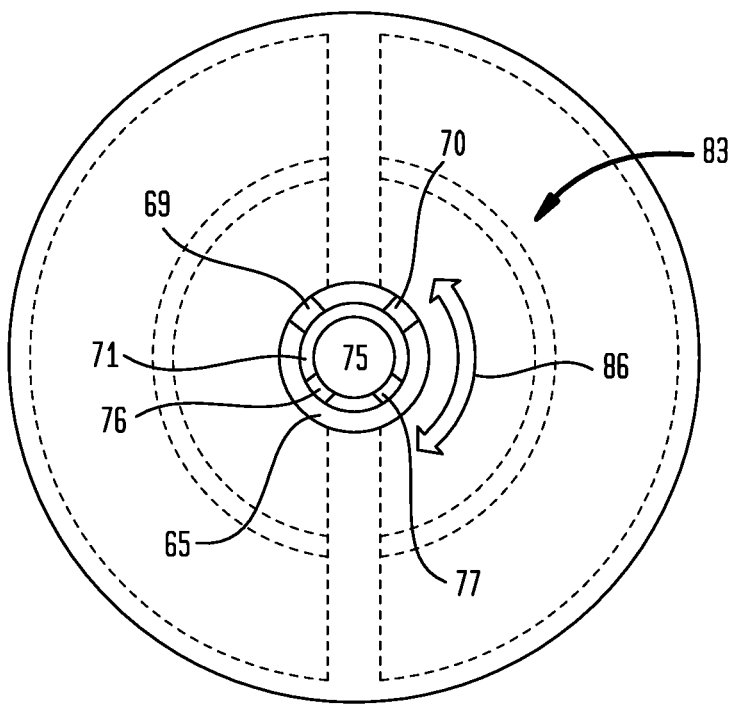
FIG. 37 is a top plan view of the particular embodiment of the ear pump showing a method of disposing a valve assembly in a fourth position.

FIG. 19C shows an example embodiment of an ear pump (1), which can be similar to the ear pump (1) embodiments of FIGS. 18 to 25. The piston (31) can be driven by an actuator (125) to press on the resilient element (3). Driving the piston (31) forward using the actuator (125) can compress the resilient element (3) can drive fluid out of the air pump (1), such as through the aperture (9). The piston (31) can be retracted using the actuator (125), which can permit the resilient element (3) to resiliently return towards the uncompressed state, which can cause fluid to be drawn into the ear pump (1), such as through the aperture (9).

Again referring primarily to FIGS. 1 through 37, the bottom aperture element (9) disposed in the support element bottom (6) and communicating between the interior chamber (8) of the support element (2) and the external ear canal (17) can, but need not necessarily, have a periphery configured as a circle, a slit, a slot, a square, or other geometric configuration. The bottom aperture element (9) can have an area (46) less than or generally equal to the area (47) of the support element bottom (6). The bottom aperture element (9) can, but need not necessarily, be disposed generally at the center (48) of the support element bottom (6), as shown in FIGS. 5, 14, 22, and 30; however, this is not intended to preclude other embodiments in which the bottom aperture element (9) has a location proximate the support element bottom peripheral margin (19) or between the support element bottom peripheral margin (19) and center (48) of the support element bottom (6).

Now referring primarily to FIGS. 26 through 37, particular embodiments of a manual ear pump (1) can further include a vesicle element (49). The vesicle element (49) can comprise one or more vesicle cavities (50) disposed in the support element peripheral wall(s) (4) and having a vesicle aperture (51) correspondingly communicating with the resilient element interior space (40). In other particular embodiments, the vesicle element (49) can comprise a material layer (52) overlaying all or a portion of the elongate tubular wall(s) (24) defining the one or more vesicle cavities (50). In particular embodiments, the vesicle element (49) can have a vesicle element top (53) configured to circumferentially couple about the support element peripheral wall(s) (4). The vesicle element (49) can have a length (54) that tapers along substantially the entire length (25) of the elongate tubular wall(s)) (24) and having the vesicle element bottom (55) being circumferentially coupled about the elongate tubular wall(s) (24) proximate or adjacent the support element bottom (6). In further particular embodiments, the vesicle element (49) can have a length (54) of less than the length (25) of the elongate tubular wall(s) (24) with the vesicle element bottom (55) medially circumferentially coupled about the elongate tubular wall(s) (24). In yet further particular embodiments, the vesicle element (49) can have two vesicle sides (56), and the vesicle element top (53) can be coupled to a portion of the support element peripheral wall(s) (4) and the vesicle element bottom (55) can be coupled to a portion of the elongate tubular wall(s) (24) or support element bottom (6), and the vesicle sides (56) can be coupled to the elongate tubular wall(s) (24).

Now referring primarily to FIGS. 26 through 30, particular embodiments of the manual ear pump (1) can operate to selectably permit a fluid (33) to flow into the vesicle element chamber (57), to permit a fluid (33) to flow into the support element interior chamber (8), to permit a fluid (33) to flow out of the support element interior chamber (8) and the vesicle element chamber (57), and to prevent a fluid (33) from flowing into or out of the vesicle element chamber (57) or support element interior chamber (8). To accomplish the multi-directional flow into the vesicle element chamber (57) and the support element interior chamber (8), the resilient element (3) can be configured to further include a valve assembly (58). The resilient element (3) can have a resilient element interior space (40) defined by the resilient element top (59), resilient element bottom (60), and resilient element peripheral wall(s) (61). The interior space (40) of the resilient element (3) can be partitioned into a pair of discrete resilient element chambers (62)(63) by an interior wall (64) extending between the resilient element top (59) to the resilient element bottom (50). A tubular conduit (65) can be centrally disposed in the interior wall (64) having a tubular conduit wall (66) disposed between a tubular conduit top (67) and a tubular conduit bottom (68). The tubular conduit (65) can further include a tubular conduit first aperture (69) and a tubular conduit second aperture (70) disposed in the tubular conduit wall (66). A tubular member (71) can be disposed within the tubular conduit (65). The tubular member (71) can have a tubular member wall (72) disposed between a tubular member top (73) and a tubular member bottom (74) defining a tubular member interior space (75). The tubular member wall (72) can be rotatingly engaged with the tubular conduit wall (66). The tubular member (71) can further include a tubular member first aperture (76) and a tubular member second aperture (77) disposed in the tubular member wall (72).

The tubular member (71) can be rotatably disposed in a first position (78) which aligns the tubular member first aperture (76) with a tubular conduit first aperture (69), where the tubular member first aperture (76) aligned with the tubular conduit first aperture (69) communicates between the tubular member interior space (75) and the first resilient element chamber (62) of the resilient element (3). A fluid (33) can flow into the tubular member (71), to the first resilient element chamber (62), and into the vesicle element (49) through a resilient element bottom first aperture (79) communicating between the vesicle element chamber (57) and the first resilient element chamber (62) upon deforming (34) the resilient element (3). The fluid (33) can flow out of the vesicle element chamber (57), to the first resilient element chamber (62), and into the tubular member (71) upon reformation (35) of the resilient element (3). The tubular member (71) can further be rotatably disposed in a second position (80) which aligns a tubular member second aperture (77) with a tubular conduit second aperture (70), where the tubular member second aperture (77) aligned with the tubular conduit second aperture (70) communicates between the tubular member interior space (75) and the second resilient element chamber (63) of the resilient element (3). A fluid (33) can flow into the tubular member (71), to the second resilient element chamber (63), and into the support element interior chamber (8) and through a resilient element bottom second aperture (81) communicating between the second resilient element chamber (63) and the support element interior chamber (8) upon deforming (34) the resilient element (3). A fluid (33) can flow from the support member interior chamber (8) and external ear canal (17), toward the second resilient element chamber (63), to the tubular member (71) upon reformation (35) of the resilient element (3). The tubular member (71) can be rotatably disposed in a third position (82) where the tubular member first aperture (76) aligns with the tubular conduit first aperture (69) and the tubular member second aperture (77) aligns with the tubular conduit second aperture (70), permitting a fluid (33) to flow into both the first and second resilient element chambers (62)(63) and into the vesicle element chamber (57) and the support element interior chamber (8) through the respective resilient element bottom first and second apertures (79)(81) upon deforming (34) the resilient element (3). The fluid (33) can flow from the vesicle element chamber (57) and the support element interior chamber (8) toward the first and second resilient element chambers (62)(63), and into the tubular conduit (65) upon reformation (35) of the resilient element (3). The tubular member (71) can be rotatably disposed in a fourth position (83) where neither the tubular member first aperture (76), tubular member second aperture (77), tubular conduit first aperture (69), nor tubular conduit second aperture (70) align, preventing fluid (33) flow into or out of the first and second resilient element chambers (62)(63).

In further particular embodiments, a rotation element (84) can, but need not necessarily, be coupled to the tubular member (71). The rotation element (84) can, but need not necessarily, be configured to have a first end (85) coupled to the tubular member top (73). The rotation element (84) can be rotated to correspondingly achieve rotatable movement (86) of the tubular member (71) to each of the first through fourth positions (78)(80)(82)(83).

In further particular embodiments, a retention element (87) can have a retention element first end (88) coupled on the resiliently flexible wall external surface (38) and a retention element second end (89) disposed to engage the rotation element (84). The retention element second end (89) engaged with the rotation element (84) prevents the resilient element (3) from being deformed (34) or reformed (35).

The material comprising the resilient element (3), support element (2), and vesicle element (49), can be a resilient material capable of elastic deformation and reformation, such as silicone-based polymers, plastics, and like materials. The material comprising the tubular member (71) and tubular conduit (65) can be a rigid plastic, metal, or other material capable of resisting deformation, or combination thereof.

Now referring primarily to FIGS. 6 through 9 and 15 through 17 and 23 through 25 and 31 through 33, particular methods of using a manual ear pump (1) can include one or more of obtaining a manual ear pump (1) including a support element (2), a resilient element (3), as those elements are described above, disposing the manual ear pump (1) in the auricle (22) (concha bowl (11)), forcibly urging (90) the resilient element (3) to deform have a deformed condition (41) to generate a fluid flow (43) from the support element interior chamber (8) through the support element bottom aperture element (9) into the external ear canal (17), and removing forcible urging (91) of the resilient element (3) allowing the resilient element (3) to return toward the non-deformed condition (42) to generate a fluid flow (43) from the external ear canal (17) toward the support element interior chamber (8) of the manual ear pump (1).

Now referring primarily to FIGS. 34 through 37, in particular embodiments including a rotation element (84), as described above, particular methods of using a manual ear pump (1) can further include rotatably disposing a rotation element (84) in a first position (78), second position (80), third position (82), or a fourth position (83), forcibly urging (90) the resilient element (3), and removing the forcible urging (91) of the resilient element (3). In some embodiments, the resilient element (3) can be held in the compressed state. For example, the ear pump (1) can have a clip or ratchet mechanism that can be engaged to hold the resilient element (3) in the compressed state, such as even after a user stops pressing the resilient element (3). This can hold a positive pressure differential in the ear. In some cases, a positive pressure differential can be applied, and the ear pump (1) can be transitioned to a state that impedes release of the positive pressure differential.

The ear pump (1) can be placed in the ear. The support element (2) can be inserted into the external ear canal. The ear pump (1) can be in the first state. For example, the rotation element (84) can be rotated to the first state. In the first state the resilient element (3) can be in fluid communication with the vesicle element (49). The resilient element (3) can be pressed to the compressed state to push fluid (e.g., air) into the vesicle element (49). The vesicle element (49) can expand, which can facilitate sealing of the ear pump (1) with the ear (e.g., with the external ear canal). Expansion of the vesicle element (49) can press against the external ear canal, which can stimulate the vagus nerve, for example. While the ear pump (1) is in the first state, releasing the resilient element (3) can cause fluid to flow out of the vesicle element (49), and into the resilient element (3) as is expands back to the uncompressed state, which can cause the vesicle element (49) to contract. By repeatedly pressing and releasing the resilient element (3), with the ear pump (1) in the first state, the vesicle element (49) can repeatedly expand and contract, which can repeatedly press against the external ear canal, which can stimulate the vagus nerve for therapeutic results. The resilient element (3) can be pressed and held in the compressed state to use the vesicle element (49) to press against the external ear canal for an extended period of time.

In some cases, the ear pump (1) can be transitioned to a different state while the vesicle element (49) is expanded, to trap the fluid in the vesicle element (49) to maintain the vesicle element (49) in the expanded state. For example, the resilient element (3) can be pressed to expand the vesicle element (49), and the ear pump (1) can then be transitioned to the fourth state, such as by rotating the rotation element (84). The fourth state can impede fluid flow between the vesicle element (49) and the resilient element (3). The fluid can remain in the vesicle element (49), with the vesicle element (49) expanded. The resilient element (3) can remain in the compressed state, even if it is no longer being pressed.

By way of another example, the resilient element (3) can be pressed to expand the vesicle element (49), and the ear pump (1) can then be transitioned to the second state, such as by rotating the rotation element (84). The second state can impede fluid flow between the vesicle element (49) and the resilient element (3), but can permit fluid to flow between the resilient element (3) and the aperture (9). Once the ear pump (1) is in the second state, the resilient element (3) can be released, which can draw fluid from the external ear canal through the aperture as the resilient element (3) expands back to the uncompressed state. This can produce a negative pressure differential with the external ear canal pressure being lower than the ambient pressure outside the ear. The negative pressure differential can further assist in sealing the ear pump (1) in the ear, as the reduced pressure in the external ear canal can draw the ear pump into the external ear canal. A sustained negative pressure differential can be maintained by releasing the resilient element (3) and by not pressing it during the time of the desired sustained negative pressure differential.

The ear pump (1) in the second state can be used similar to the discussion relating to the use of the embodiments of FIGS. 1 to 25. In the second state, fluid flow is permitted between the resilient element (3) and the external ear canal (17), and fluid flow is impeded between the resilient element (3) and the vesicle element (49). Accordingly, the ear pump (1) of FIGS. 26 to 37 can operate similar to the ear pumps (1) of FIGS. 1 to 25, as discussed herein.

In the third state, the ear pump (1) can be used to stimulate multiple areas of the ear simultaneously. The ear pump (1) can be placed into the ear, such as with the support element (2) inserted into the external ear canal. The ear pump (1) can be in the third state, which can provide fluid communication between the resilient element (3) and both the vesicle element (49) and the external ear canal (17) (e.g., via aperture (9)). Pressing the resilient element (3) can simultaneously cause the vesicle element (49) to expand, as discussed herein, which can stimulate the vagus nerve, and increase the pressure in the external ear canal (17) to produce a positive pressure differential between the external ear canal (17) and ambient pressure. The pressure differential can move the tympanic membrane, which can stimulate the trigeminal system. Movement of the tympanic membrane can trigger mechanoreceptors to produce neurological signals, which can have therapeutic effects for treating medical conditions such as migraine headaches and other neurological disorders. With the ear pump (1) in the third state, the resilient element (3) can be pressed and released repeatedly, which can create pulses of pressure differentials and vesicle element (49) expansions. The resilient element (3) can be pressed and held to produce a sustained pressure differential and simultaneous vesicle element (49) expansion.

Figure 38:
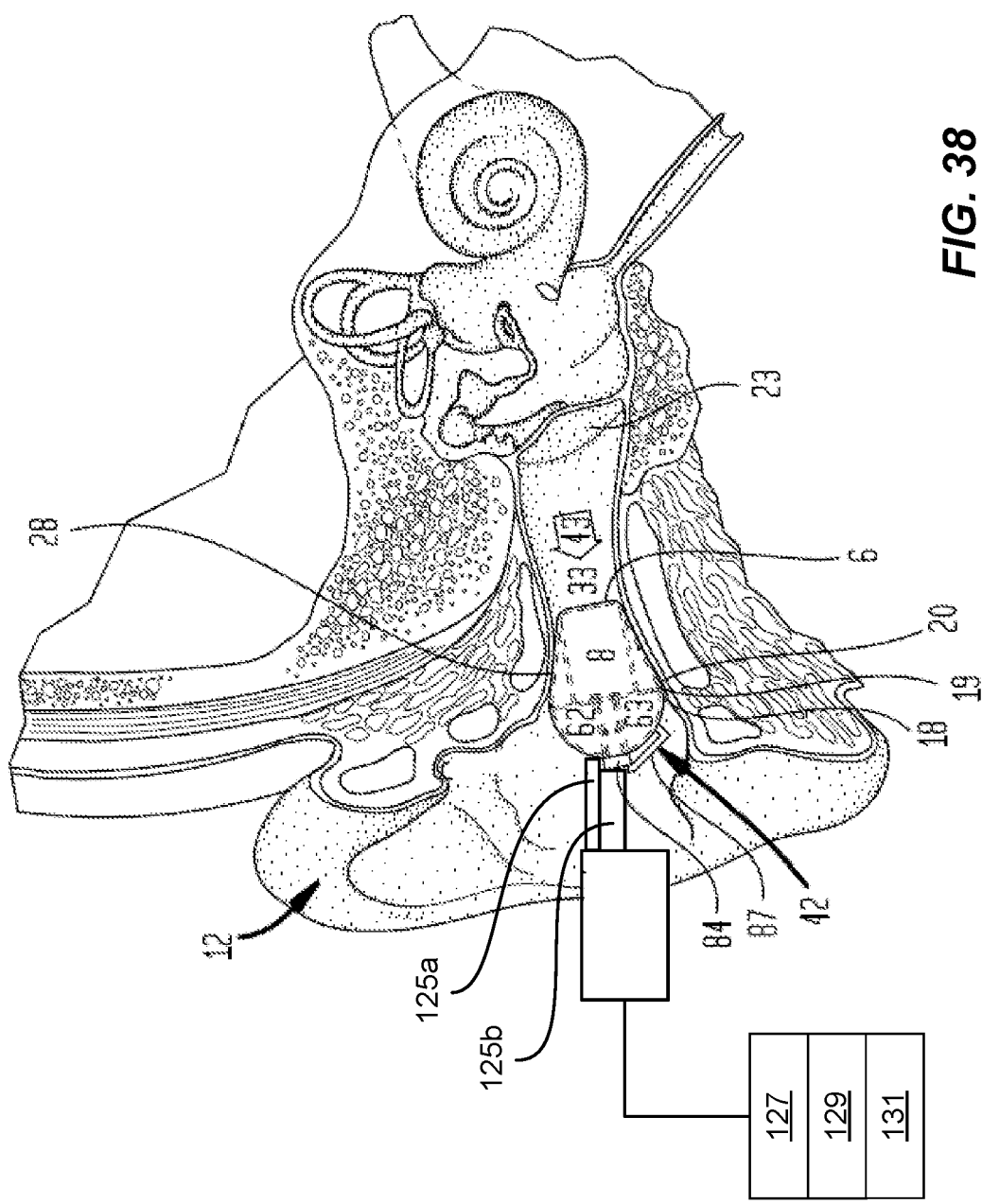
FIG. 38 is a cross-sectional view showing an example embodiment of an actuator operating an ear pump.

FIG. 38 shows an example embodiment of an actuator 125 for use with the ear pump (1) of FIGS. 26 to 37. The actuator 125 can have a fluid flow actuator portion 125*a*, which can be used to press the resilient element (3), similar to the discussion herein relating to other embodiments. The actuator 125 can include a valve actuator portion 125*b*, which can be configured to change the valve between states (such as between the four states discussed herein). The valve actuator portion 125*b* can engage the rotation element (84). Rotation of the valve actuator portion 125*b* can cause the rotation element (84) to rotate, which can change the state of the valve of the ear pump (1). The controller (127) can operate the valve actuator (125*b*) and the fluid flow actuator (125*a*) to implement the procedures and methods described herein, in some cases in automated fashion. Although various embodiments here are discussed in connection with manual ear pumps, any of the embodiments disclosed herein can be used with an automated system, such as including one or more actuators, which can be computer controlled (e.g., operated by a controller).

In some embodiments, the ear pump (1) can be heated or cooled before being engaged with the ear. This can cause heating or cooling of the ear, which can stimulate neurological responses that can be therapeutic. Heating the ear can also increase the intensity of neurological responses provided by the ear pump (1). For example, heating the tympanic membrane can result in stronger neurological signals from movement of the tympanic membrane produced the pressure differentials discussed herein.

The support element (2) can have a diameter (26) that is larger than the diameter (27) of the external ear canal opening (28). The support element (2) can have a diameter (26) that is larger than the diameter of the resilient element (3). In some embodiments, the ear pump (1) can be contained in the ear. For example, the ear pump (1) can be contained within the footprint of the auricle of the ear. In some cases, no component of the ear pump (1) extends beyond the ear. In some embodiments, the ear pump (1) does not extend into the external ear canal (17), while in other embodiments, a portion of the ear pump (1) can extend into the external ear canal (17). In some embodiments, the fluid flow generator (e.g., the resilient element (3) can be directly coupled to the support element (2) that engages the ear. In some cases, the ear pump (1) does not include any flexible tube or conduit that connects the fluid flow generator to the earpiece. In some cases, the fluid flow generator (e.g., the resilient element (3)) can be positioned in the concha bowl of the ear. In some cases, a line extending axially outward of the external ear canal can intersect the fluid flow generator (e.g., the resilient element (3)).

The ear pump (1), in some embodiments, may comprise a pressure-regulating conduit configured to decrease a pressure differential between the external ear canal and an atmospheric pressure, when the ear-pump (1) is in use. The pressure-regulating conduit may permit the ear-pump to undergo a controlled pressure leak. For example, the ear-pump (1) may be able to apply positive and/or negative pressure up to a desired treatment pressure level. The pressure-regulating conduit may then permit fluid flow egress from and/or ingress towards the external ear canal to equalize the pressure within the external ear canal with atmospheric pressure. It will be understood by one having skill in the art that any of the embodiments described and/or contemplated herein, or any components or features thereof, can be modified to include the pressure-regulating conduit, as described herein.

In some embodiments, the pressure-regulating conduit may comprise a controlled-leak valve that permits fluid flow into and/or out of the external ear canal. For example, the controlled-leak valve may comprise a vent and/or porous material that is configured to permit fluid flow through the controlled-leak valve at a decreased rate of change. The type of valve and/or material may be selected depending on the desired rate of pressure change. In some embodiments, a particular material may be selected that allows the application of positive and/or pressure to effectively treat a user's condition while also decreasing the amount of pressure applied to the user's external ear canal.

The pressure-regulating conduit may be located at any location on the ear-pump (1) that is in fluid communication with the external ear canal. In some embodiments, the pressure-regulating conduit may be located at least at the resilient element (3) or the support element (2). For example, the pressure-relief conduit may comprise bore extending through an external surface (e.g. external surface (38) or external surface (10)) to permit controlled fluid flow to and/or from the aperture (9). The pressure-regulating conduit, in some instance, may be located along the external surface (10) of the support element (2) when the resilient element (3) comprises a one-way valved conduit to control the application of positive and/or negative pressure, as described herein.

In some embodiments, the pressure-regulating conduit may include features similar to the valve assembly (58) described in connection with FIGS. 26-37. The valve assembly (58), in some instances, may be configured to open and/or close the pressure-regulating conduit to selectively control the equalization of the external ear canal pressure with atmospheric pressure.

Any earpiece (1) disclosed herein, in some embodiments, may be configured to interact with one or more audio generators. The one or more audio generators may be configured to signal one or more audio commands or information to a user. The one or more audio generators may provide an indication to the user regarding the application of treatment, such as when and/or how to apply additional pressure the earpiece (1), when to remove the earpiece (1), when to switch the earpiece (1) to the other ear, and/or any other treatment parameter. The one or more audio generators can provide therapeutic audio signals (e.g., tones) to the user.

The one or more audio generators may be located within a housing separate from the earpiece (1). The audio generator may generate a sound that is configured to be propagated through the earpiece (1) located within the user's ear and to the external ear canal of a user. The propagation of the audio along the fluid (e.g., air) through the earpiece (1) advantageously allows the user to hear an audio cue even during a treatment procedure. For example, a user wearing the earpiece (1) may be unable to hear an audio cue generated by an external device connected to the earpieces(s), such as audio from the user device (e.g., smartphone). The use of the earpiece (1) to propagate the sound (e.g., audio cue) generated by the audio generator permits the sound to travel directed towards the user's ear canal to be heard by the user. In some embodiments, the audio generator may be located outside the earpiece (1). For example, the audio generator may be fluidly connected to the resilient element (3) and/or other structure of the earpiece (1). In some embodiments, the audio generator can be positioned on or near the resilient member (3). The audio generator can be a speaker, a vibrator, or other suitable element that can produce sounds.

As discussed herein, the earpiece (1) may interact with the one or more audio generators for an audio treatment that uses sounds (e.g., to stimulate therapeutic neurological responses). The earpiece (1) may use an audio treatment parameter profiles that include information indicative of parameters for the audio treatment (e.g., different tones, volumes, and durations, for sounds at different times). The one or more audio generators may be configured to introduce various tone frequencies, such as tones known to have therapeutic effects. The tones may be within audible or inaudible ranges. In some instances, the audio generator may provide music known to have therapeutic effects.

The treatment system can provide an audio treatment parameter profile in isolation or in combination with any other treatment discussed herein. For example, in some embodiments, the earpiece (1) may superimpose a generator audio cue with the pressure therapy. The supplemental therapies can improve or harmonize with the foundation therapy. For example, a negative pressure therapy configured stretch a muscle may be followed by an audio cue that causes the stretched muscle to reflex. The reflex may trigger and stimulate receptors on the muscle to provide a therapeutic effect. A synergy can be produced in many instances where the combination of therapies can have therapeutic results that are superior to the sum of results of the individual therapies. Further details and features relating to audio systems and treatments are discussed in the PCT Patent Application No. PCT/US2017/064964, which is incorporated by reference.

In some embodiments, the ear pump (1) can have a removable support element (2), which can be interchanged for different sizes or shapes of ears. In some embodiments, the ear-pump (1) may include an earplug portion. The earplug can comprise at least a portion of the support element (2) (e.g. the elongate tubular wall (24) and/or the support element peripheral wall (4)) and can be removably coupled to at least another portion of the ear-pump (1) (e.g., the resilient element (3)). For example, the earplug may utilize a twist lock configuration and/or any other attachment mechanism configured to removably attach the earplug to a corresponding locking structure on the ear-pump (1).

The earplugs, in some instances, may be positioned and/or oriented such that a central longitudinal axis of the earplugs is generally collinear with a central longitudinal axis of the ear-pump (1). It will be understood that the earplugs can have any suitable form and/or configuration. For example, as shown in FIGS. 10-17, the earplugs can comprise the elongate tubular wall (24) having a generally cylindrical shape. In some embodiments, the elongate tubular wall (24) can extend between the support element peripheral wall (4) and the support element bottom (6), as discussed herein.

Different users can have ear canals that are different shapes and sizes. In some instances, a user may position an ear-pump in a suboptimal position when the shape and/or size does not conform with the user's ear canal. These factors may result in leaks. To compensate for this issue, the ear-pump (1), in some implementations, may comprise two or more sets of earplugs having various configurations, such as different lengths, different diameters, different cross-sectional areas, etc. A user may select a particular earplug based on the user's needs and attach the selected earplug to the ear-pump (1). The sets of earplugs can be interchangeable. For example, a user may select an earplug that best fits a user's ear. In some instance, the earplug may be pre-formed and customized to a user's particular anatomy to closely conform to the 3 dimensional shape of the user's external ear canal and/or the auricle. The earplug can be made by molding, thermal forming, or by other methods.

Figure 15:
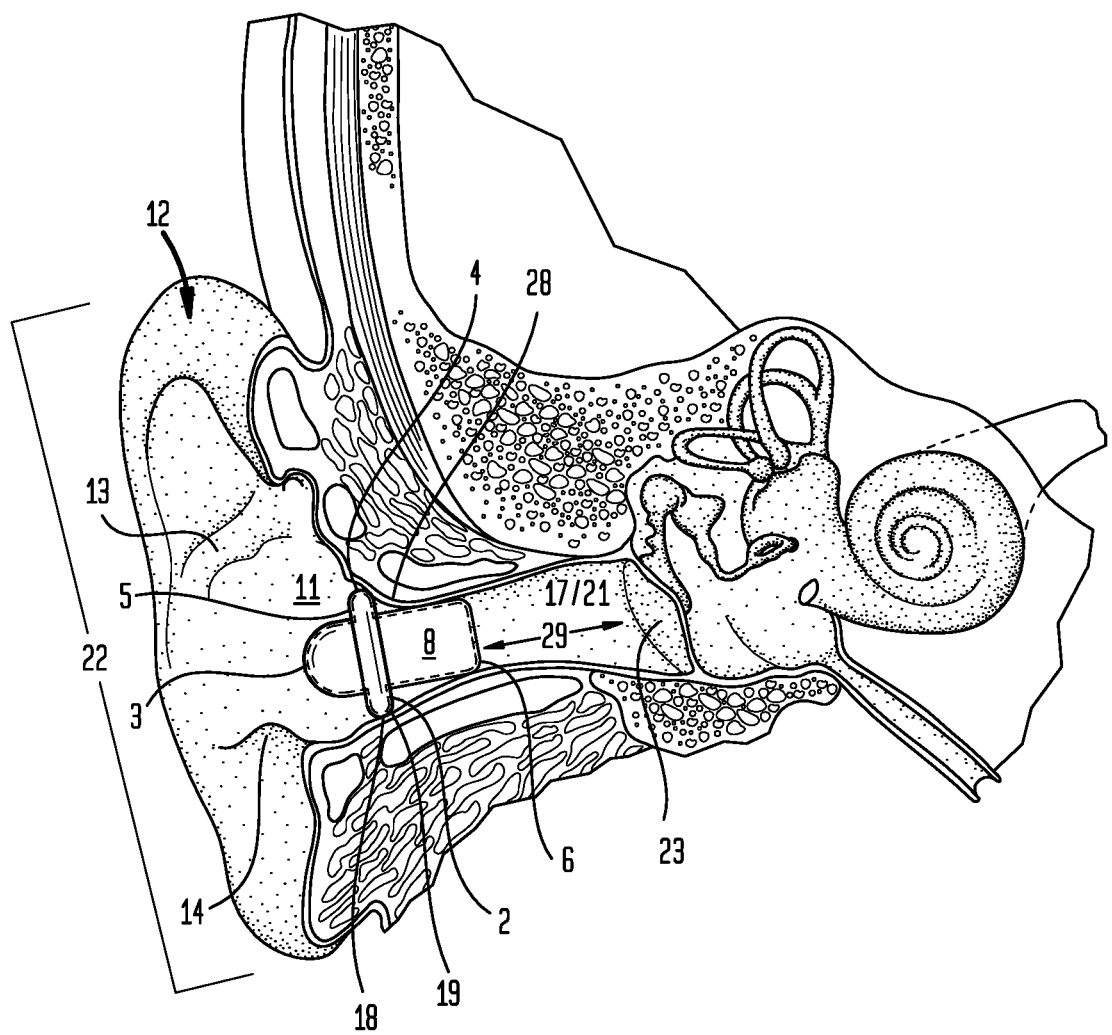
FIG. 15 is a cross-sectional view of the anatomy of the ear showing the particular embodiment of the ear pump releasably retained in the auricle of the ear.

The earplug may be configured to interact with any portion of the user's ear described herein (e.g. the external ear canal, tragus, the antitragus, the concha, and/or the concha bowl). The interaction of these various structures can advantageously facilitate engagement and/or retention of the ear-pump (1) with the user's ear. As shown in FIGS. 15-17, in some embodiments, the elongate tubular wall (24) may have a length shorter than an overall length of the user's external ear canal, such that the ear-pump (1) does not come into direct contact with the tympanic member (23). In some embodiments, the earplug and/or elongate tubular wall (24) may have a length configured to provide sufficient interaction with the external ear canal to attach and/or retain the earplug within the user's ear.

As illustrated, the exterior surface of the earplug and/or elongate tubular wall (24) can be flat and/or planar, and/or substantially flat and/or substantially planar. In some embodiments, the earplug may have any suitable surface texture, such as, for example, smooth and/or rough. In some embodiments, the earplug can be made of a compressible, deformable, and/or resilient material. However, any suitable material can be used.

In some embodiments, the earplug may be configured to be moldable to form-fit into a user's external ear canal. The moldable earplug can be adapted for retention or releasable retention of the ear-pump within the external ear canal. In some implementations, the earplug may be made of a material that can be heated to achieve the moldable condition. For example, when the earplug is heated, the earplug may allow for reconfiguration of at least a portion of the earplug (e.g., the elongate tubular wall (24)) when a user engages the earplug with the external ear canal. The material may be further configured to enter a fixed configuration when the material is cooled. In some embodiments, the earplug may be cooled after it engages the external ear canal. In this manner, the earplug may cool and enter a fixed condition once the earplug is shaped to more closely match the configuration of the external ear canal. In some embodiments, the earplug can be provided in combination as part of a moldable earpiece system provided as part of a kit which can be used by a user for production of an earpiece having greater conformity with the user's external ear canal for retention or releasable retention of the ear-pump (1) within the ear of a user.

As shown in the figures, various features of the ear-pump (1) can comprise the various indicated dimensions. It will be appreciated that these dimensions, as well as the dimensions indicated in the Figures are exemplary and non-limiting. Indeed, it will be understood, that the dimensions can be modified for any suitable embodiment, and that their relative proportions can differ in various embodiments.

As can be easily understood from the foregoing, the basic concepts of the present disclosure may be embodied in a variety of ways. The disclosure involves numerous and varied embodiments of ear pumps and methods for making and using such ear pumps. As such, the particular embodiments or elements disclosed by the description or shown in the figures or tables accompanying this application are not intended to be limiting, but rather are examples of the numerous and varied embodiments generically encompassed by the disclosure or equivalents encompassed with respect to any particular element thereof. In addition, the specific description of a single embodiment or element may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this disclosure is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "support" should be understood to encompass disclosure of the act of "supporting"—whether explicitly discussed or not—and, conversely, were there effectively disclosure of the act of "supporting", such a disclosure should be understood to encompass disclosure of a "support" and even a "means for supporting." Such alternative terms for each element or step are to be understood to be explicitly included in the description.

All numeric values herein are assumed to be modified by the term "about", whether or not explicitly indicated. Ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment. Moreover, the term "a" or "an" entity refers to one or more of that entity unless otherwise limited. As such, the terms "a" or "an", "one or more" and "at least one" can be used interchangeably herein, unless context clearly indicates otherwise.

Thus, the applicant(s) should be understood to claim at least: i) each of the ear pumps herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the disclosure pertains. This section may also incorporate or contain paraphrasing of certain United States patents, patent applications, publications, or subject matter useful in relating information, problems, or concerns about the state of technology to which the disclosure is drawn toward. It is not intended that any United States patent, patent application, publication, statement or other information cited or incorporated herein be interpreted, construed or deemed to be admitted as prior art.

The claims set forth in this specification, if any, are hereby incorporated by reference as part of this description of the disclosure, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the embodiments and are not to be construed as the broadest embodiment or a complete listing of embodiments that may be claimed. The applicant does not waive any right to develop further claims based upon the description set forth above as a part of any continuation, division, or continuation-in-part, or similar application.

In some embodiments, the methods, techniques, microprocessors, and/or controllers described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination thereof. The instructions can reside in RAM memory, flash memory, ROM memory, EPROM memory, EEPROM memory, registers, hard disk, a removable disk, a CD-ROM, or any other form of a non-transitory computer-readable storage medium. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

The microprocessors or controllers described herein can be coordinated by operating system software, such as iOS, Android, Chrome OS, Windows XP, Windows Vista, Windows 7, Windows 8, Windows 10, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

The microprocessors and/or controllers described herein may implement the techniques described herein using customized hard-wired logic, one or more ASICs or FPGAs, firmware and/or program logic which causes microprocessors and/or controllers to be a special-purpose machine. According to one embodiment, parts of the techniques disclosed herein are performed a controller in response to executing one or more sequences instructions contained in a memory. Such instructions may be read into the memory from another storage medium, such as storage device. Execution of the sequences of instructions contained in the memory causes the processor or controller to perform the process steps described herein. In alternative embodiments, hard-wired circuitry may be used in place of or in combination with software instructions.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the techniques described herein may be implemented in analog circuitry or mixed analog and digital circuitry.

Unless the context clearly requires otherwise, throughout the description and the claims, the words "comprise," "comprising," "include," "including," and the like are to be construed in an inclusive sense, as opposed to an exclusive or exhaustive sense; that is to say, in the sense of "including, but not limited to." The words "coupled" or connected," as generally used herein, refer to two or more elements that can be either directly connected, or connected by way of one or more intermediate elements. Additionally, the words "herein," "above," "below," and words of similar import, when used in this application, shall refer to this application as a whole and not to any particular portions of this application. Where the context permits, words in the Detailed Description using the singular or plural number can also include the plural or singular number, respectively. The words "or" in reference to a list of two or more items, is intended to cover all of the following interpretations of the word: any of the items in the list, all of the items in the list, and any combination of the items in the list. All numerical values provided herein are intended to include similar values within a range of measurement error.

Although this disclosure contains certain embodiments and examples, it will be understood by those skilled in the art that the scope extends beyond the specifically disclosed embodiments to other alternative embodiments and/or uses and obvious modifications and equivalents thereof. In addition, while several variations of the embodiments have been shown and described in detail, other modifications will be readily apparent to those of skill in the art based upon this disclosure. It is also contemplated that various combinations or sub-combinations of the specific features and aspects of the embodiments may be made and still fall within the scope of this disclosure. It should be understood that various features and aspects of the disclosed embodiments can be combined with, or substituted for, one another in order to form varying modes of the embodiments. Any methods disclosed herein need not be performed in the order recited. Thus, it is intended that the scope should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Any headings used herein are for the convenience of the reader only and are not meant to limit the scope.

Further, while the devices, systems, and methods described herein may be susceptible to various modifications and alternative forms, specific examples thereof have been shown in the drawings and are herein described in detail. It should be understood, however, that the disclosure is not to be limited to the particular forms or methods disclosed, but, to the contrary, this disclosure covers all modifications, equivalents, and alternatives falling within the spirit and scope of the various implementations described. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including ambient temperature and pressure.

The following is claimed:

1. An ear pump comprising:
   a resilient element capable of being resiliently deformed, the resilient element having a compressed state and an uncompressed state;
   a support element configured for insertion into an external ear canal, the support element comprising:
      a fluid flow pathway;
      an opening for fluid to flow between the fluid flow pathway and the external ear canal; and
      one or more vesicle cavities; and
   a valve having:
      a first state to permit fluid flow from the resilient element to the one or more vesicle cavities while impeding fluid flow from the resilient element to the fluid flow pathway; and
      a second state to permit fluid flow from the resilient element to the fluid flow pathway while impeding fluid flow from resilient element to the one or more vesicle cavities.

2. The ear pump of claim 1, wherein the valve has a third state to permit fluid flow between the resilient element and the fluid flow pathway and to also permit fluid flow between the resilient element and the one or more vesicle cavities.

3. The ear pump of claim 2, wherein the valve has a fourth state to impede fluid flow between the resilient element and the fluid flow pathway and to also impede fluid flow between the resilient element and the one or more vesicle cavities.

4. The ear pump of claim 1, wherein the valve comprises a rotation element, and wherein rotation of the rotation element changes the valve between the first state and the second state.

5. The ear pump of claim 1, wherein the valve comprises:
   a tubular conduit having a first tubular conduit aperture and a second tubular conduit aperture; and
   a tubular member having a first tubular member aperture and a second tubular member aperture;
   wherein the tubular member is rotatable relative to the tubular conduit;

wherein the tubular member is positioned to align the first tubular member aperture with the first tubular conduit aperture and to not align the second tubular member aperture with the second tubular conduit aperture when the valve is in the first state;

wherein the tubular member is positioned to align the second tubular member aperture with the second tubular conduit aperture and to not align the first tubular member aperture with the first tubular conduit aperture when the valve is in the second state.

6. The ear pump of claim 5, wherein the tubular member is positionable to align the first tubular member aperture with the first tubular conduit aperture and to also align the second tubular member aperture with the second tubular conduit aperture to permit fluid flow between member aperture and a second tubular member and both the fluid flow pathway and the one or more vesicle cavities.

7. The ear pump of claim 5, wherein the tubular member is positionable to not align the first tubular member aperture with the first tubular conduit aperture and to also not align the second tubular member aperture with the second tubular conduit aperture to impede fluid flow between the resilient element and both the fluid flow pathway and the one or more vesicle cavities.

8. The ear pump of claim 1, wherein the one or more vesicle cavities are expandable to facilitate sealing of the support element with the external ear canal.

9. The ear pump of claim 1, wherein when the valve is in the first state, compression of the resilient element to the compressed state causes fluid to flow into the one or more vesicle cavities to expand the one or more vesicle cavities and decompression of the resilient element to the uncompressed state causes fluid to flow out of the one or more vesicle cavities.

10. The ear pump of claim 1, wherein the ear pump is a manual ear pump.

11. The ear pump of claim 1, wherein the ear pump is configured to not extend beyond an auricle of the ear and the external ear canal.

12. The ear pump of claim 1, wherein the ear pump is contained within an auricle of the ear and the external ear canal.

13. The ear pump of claim 1, wherein the resilient element and the support element are made of the same material.

14. The ear pump of claim 1, wherein the resilient element and the support element are integrally formed as a single piece.

15. The ear pump of claim 1, wherein a wall separates the resilient element from the support element.

16. The ear pump of claim 15, wherein the wall comprises a first aperture that provides fluid communication through the wall to the one or more vesicle cavities, and wherein the wall comprises a second aperture that provides fluid communication through the wall to the fluid flow pathway.

17. The ear pump of claim 1, further comprising an actuator for pressing the resilient element and a controller for operating the actuator.

18. The ear pump of claim 1, further comprising an actuator for changing the valve between the first state and the second state and a controller for operating the actuator.

* * * * *

UNITED STATES PATENT AND TRADEMARK OFFICE
CERTIFICATE OF CORRECTION

PATENT NO. : 11,246,793 B2
APPLICATION NO. : 16/549222
DATED : February 15, 2022
INVENTOR(S) : David Mager George et al.

It is certified that error appears in the above-identified patent and that said Letters Patent is hereby corrected as shown below:

In the Specification

In Column 13, Line 36, delete "egres sing" and insert --egressing--.

In the Claims

In Column 31, Claim 6, Lines 15-16, delete "member aperture and a second tubular member" and insert --the resilient element--.

Signed and Sealed this
Twenty-fourth Day of May, 2022

Katherine Kelly Vidal
*Director of the United States Patent and Trademark Office*